US011040963B2

(12) United States Patent
Van Dongen et al.

(10) Patent No.: US 11,040,963 B2
(45) Date of Patent: Jun. 22, 2021

(54) PIPERAZINE DERIVATIVES FOR INFLUENZA VIRUS INHIBITIONS

(71) Applicant: JANSSEN VACCINES & PREVISION B.V., Leiden (NL)

(72) Inventors: Maria Van Dongen, Hilversum (NL); Jaroslaw Juraszek, Amsterdam (NL); Griet Wim Bert Schepens, Sint-Katelijne-Waver (BE); Charles Edward Lawson, Pipersville, PA (US); Brian Shook, Holliston, MA (US); Maria Tim Hugo Jonckers, Heist-op-den-Berg (BE); Abdellah Tahri, Anderlecht (BE); Bernard Pierre Jean-Marie Raboisson, Rosieres (BE); Nestor CHristophe Francis Robert Buyck, Hamme (BE)

(73) Assignee: JANSSEN VACCINES & PREVENTION B.V., Leiden (NL)

( * ) Notice: Subject to any disclaimer, the term of this patent is extended or adjusted under 35 U.S.C. 154(b) by 0 days.

(21) Appl. No.: 16/483,283

(22) PCT Filed: Feb. 1, 2018

(86) PCT No.: PCT/EP2018/052537
§ 371 (c)(1),
(2) Date: Aug. 2, 2019

(87) PCT Pub. No.: WO2018/141854
PCT Pub. Date: Aug. 9, 2018

(65) Prior Publication Data
US 2020/0010459 A1  Jan. 9, 2020

Related U.S. Application Data

(60) Provisional application No. 62/453,673, filed on Feb. 2, 2017.

(30) Foreign Application Priority Data

Feb. 16, 2017  (EP) .................................. 17156448

(51) Int. Cl.

| C07D 413/10 | (2006.01) |
|---|---|
| A61P 31/16 | (2006.01) |
| C07D 401/10 | (2006.01) |
| C07D 413/14 | (2006.01) |
| C07D 417/10 | (2006.01) |
| C07D 417/14 | (2006.01) |
| C07D 487/08 | (2006.01) |
| C07D 498/04 | (2006.01) |
| C07D 263/57 | (2006.01) |
| C07D 413/12 | (2006.01) |
| C07D 277/66 | (2006.01) |
| C07D 417/12 | (2006.01) |
| C07D 295/108 | (2006.01) |
| C07D 307/79 | (2006.01) |
| C07D 235/18 | (2006.01) |

(52) U.S. Cl.
CPC ............ *C07D 413/10* (2013.01); *A61P 31/16* (2018.01); *C07D 235/18* (2013.01); *C07D 263/57* (2013.01); *C07D 277/66* (2013.01); *C07D 295/108* (2013.01); *C07D 307/79* (2013.01); *C07D 401/10* (2013.01); *C07D 413/12* (2013.01); *C07D 413/14* (2013.01); *C07D 417/10* (2013.01); *C07D 417/12* (2013.01); *C07D 417/14* (2013.01); *C07D 487/08* (2013.01); *C07D 498/04* (2013.01)

(58) Field of Classification Search
CPC .. C07D 413/10; C07D 263/57; C07D 413/14; C07D 413/04; C07D 498/04; C07D 417/12; C07D 295/108; C07D 307/791
See application file for complete search history.

(56) References Cited

U.S. PATENT DOCUMENTS

| 5,656,642 A | 8/1997 | Fujioka et al. | |
|---|---|---|---|
| 2005/0054697 A1* | 3/2005 | Yager ...................... | A61P 43/00 514/365 |

FOREIGN PATENT DOCUMENTS

| WO | WO 9422826 | * 10/1994 |
|---|---|---|
| WO | 2008/028946 A2 | 3/2008 |
| WO | 2009/117444 A1 | 9/2009 |
| WO | 2011/015037 A1 | 2/2011 |
| WO | 2012/033736 A1 | 3/2012 |
| WO | 2012/144752 A1 | 10/2012 |

(Continued)

OTHER PUBLICATIONS

Carbo. Journal of Medicinal Chemistry, 2016, 59, 10113-10126. (Year: 2016).*
Brandenburg, et al., "Mechanisms of Hemagglutinin Targeted Influenza Virus Neutralization", PLOS ONE, vol. 8, Issue 12, pp. 1-14. (2012).

(Continued)

*Primary Examiner* — Noble E Jarrell
(74) *Attorney, Agent, or Firm* — Kramer Amado, P.C.

(57) ABSTRACT

The present invention provides piperazine derivatives exhibiting high affinity to the stem region (viral membrane proximal part) of influenza hemagglutinin as determined through competition binding and high virus neutralization activity while having low cytotoxicity. Furthermore, the present invention relates to pharmaceutical compositions comprising said piperazine derivatives, methods of preparing said piperazine derivatives, as well as said piperazine derivatives for use in medical prevention or treatment, especially for preventing or treating influenza.

20 Claims, No Drawings

(56) References Cited

FOREIGN PATENT DOCUMENTS

WO    2013/007770 A1    1/2013

OTHER PUBLICATIONS

Dou, et al., "Inhibition of noroviruses by piperazine derivatives", Bioorganic & Medicinal Chemistry Letters, 22, pp. 377-379. (2012).
Whitehead, et al., "Optimization of affinity, specificity and function of designed influenza inhibitors using deep sequencing", Nature Biotechnology, vol. 30, No. 6, pp. 543-551. (May 2012).
International Search Report dated Mar. 21, 2018 in connection with International Application No. PCT/EP2018/052537, filed Feb. 1, 2018.

* cited by examiner

PIPERAZINE DERIVATIVES FOR INFLUENZA VIRUS INHIBITIONS

TECHNICAL FIELD

The present invention relates to the field of influenza antivirals. More specifically, the present invention relates to the field of piperazine derivatives having low cytotoxicity, exhibiting high affinity to the stem region (viral membrane proximal part) of influenza hemagglutinin as determined through competition binding and having high virus neutralization activity. Furthermore, the present invention relates to pharmaceutical compositions comprising said piperazine derivatives, methods of preparing said piperazine derivatives, as well as said piperazine derivatives for use in medical prevention and/or treatment, especially for preventing and/or treating influenza.

INTRODUCTION

Influenza is a serious public health problem with a high incidence in the human population resulting in regular large-scale morbidity and mortality. It is a highly contagious airborne disease that causes an acute febrile illness. Systemic symptoms vary in severity from mild fatigue to respiratory failure and death. According to the WHO the average global burden of annual epidemics may be on the order of 1 billion cases, 3-5 million cases of severe illness and 300,000-500,000 deaths annually. Every year, influenza viruses circulate in humans, typically affecting 5-20% of the population in all age groups, with this FIGURE rising up to 30% during major epidemics. Rates of serious illness and death are highest among persons aged >65 years, children aged <2 years, and persons of any age who have medical conditions that place them at increased risk for complications from influenza, such as chronic heart, lung, kidney, liver blood or metabolic diseases, or weakened immune systems. Although deaths are infrequent among children, rates of hospitalization range from approximately 100 to 500 per 100,000 for children <5 years-old depending on the presence or absence of co-morbid conditions. Hospitalization rates among children aged <24 months are comparable to rates reported among persons aged >65 years.

In the US, annual influenza epidemics lead to approximately 30 million outpatient visits, resulting in medical costs of $10 billion annually. Lost earnings due to illness and loss of life represent a cost of over $15 billion annually and the total US economic burden of annual influenza epidemics amounts to over $85 billion.

Pathogens that cause influenza are negative sense, single-stranded RNA viruses, which belong to the family of Orthomyxoviridae. There are three types of influenza viruses: A, B and C. Influenza A viruses are the most common form, which can spread in mammals and birds. The subtypes of influenza A are named by the types of surface proteins hemagglutinin (H) and neuraminidase (N). There are 18 different hemagglutinin and 11 known neuraminidases. Current seasonal influenza viruses found in human are mainly H1N1 and H3N2 subtypes. Influenza B viruses are usually found only in humans. They are not divided into subtypes, but can be further broken down into different strains. Circulating influenza viruses are highly variable each year, and both influenza A and B cause seasonal epidemics all over the world. Influenza C viruses give much milder symptoms, which do not cause epidemics.

All three types of viruses have similar genome structures. The genome comprises 8 segments, encoding 9-11 proteins, depending on the type. Influenza A encodes 11 proteins, which includes the surface proteins hemagglutinin (HA) and Neuraminidase (NA), the polymerase complex (PA, PB1 and PB2), nucleoprotein (NP), membrane proteins (M1 and M2), and other proteins (NS1, NS2, NEP). Among the three influenza virus types, influenza A has the highest rate of mutation. Influenza B evolves slower than A but faster than C. The segmented genome allows gene exchanging between different viral strains, which generate new variants of influenza viruses.

Influenza virus can be transmitted among humans by direct contact with infected individuals or virus-contaminated material. One can also be infected by inhalation of suspended virus droplets in the air. Those droplets are generated by coughing, sneezing or talking of infected individuals. Seasonal influenza is characterized by a sudden onset of high fever, cough (usually dry), headache, muscle and joint pain, severe malaise (feeling unwell), sore throat and runny nose. Cough can be severe and can last two or more weeks. Most people recover from fever and other symptoms within a week without requiring medical attention. But influenza can cause severe illness or death especially in people at high risk as mentioned above. The time from infection to illness, known as the incubation period, is about two days.

The most effective way to prevent the disease and/or severe outcomes from the illness is vaccination. Safe and effective vaccines are available and have been used for more than 60 years. Among healthy adults, influenza vaccines can provide reasonable protection. However, vaccination comes with several limitations. First, influenza vaccine may be less effective in preventing illness among the elderly, and may only reduce severity of disease and incidence of complications and deaths. In addition, influenza vaccination is most effective when circulating viruses are well-matched with vaccine viruses, and the success of vaccination is largely dependent on the good prediction of the most prevalent virus type of the season. Rapid and continual evolution of influenza viral strains through antigenic drift, coupled with the short-lived nature of vaccine-induced immune responses to current influenza vaccines, means that vaccination with seasonally appropriate strains is required every year for prevention.

The current treatment of influenza uses either direct antiviral drugs, or medicines that release the influenza-induced symptoms. There are few classes of influenza antiviral drugs available on the market, mostly neuraminidase inhibitors and M2 channel inhibitors. Recently favipiravir (T-705) RNA polymerase inhibitor was approved in Japan for use against novel or re-emerging influenza viruses. Neuraminidase inhibitors oseltamivir or zanamivir are the primary antiviral agents recommended for the prevention and treatment of influenza. These are effective against both influenza type A and B viruses. Development of resistance to these antiviral drugs has been identified during treatment of seasonal influenza and in sporadic oseltamivir-resistant 2009H1N1 virus, yet the public health impact has been limited to date. M2 channel inhibitors, such as amantadine and rimantadine (amantadanes), are active against influenza A strains, but not influenza B strains. Adamantane resistance among circulating influenza A viruses increased rapidly worldwide beginning during 2003-2004. Therefore, amantadine and rimantadine are not recommended for antiviral treatment or chemoprophylaxis of currently circulating influenza A virus strains.

The discovery of novel influenza antivirals acting on the surface protein hemagglutinin as an alternative strategy to prevent and/or treat influenza infection is hampered by the large sequence variability of this protein. Hemagglutinin ligands described so far therefore only show activity against a limited number of closely related influenza strains. Nevertheless, antibodies capable of interacting with large variety of hemagglutinin proteins and capable of neutralizing a broad spectrum influenza A and/or B viruses have recently been described, such as CR9114 (as disclosed in WO2013/007770), and CR6261 (disclosed in WO2008/028946). The binding epitope of such antibodies in the stem region of hemagglutinin causes them to interfere with large structural rearrangements of the hemagglutinin protein at low pH, which are critical for the membrane fusion mechanism that the virus utilizes to release its genome into the cytoplasm, allowing the infection to progress (Brandenburg et al. (2013); PLoS One. 2013 Dec. 11; 8(12):e80034). As a result of their potency and breadth, such antibodies are now being developed for therapeutic treatment of severely ill patients and prophylactic applications for people belonging to high risk groups. The relative high costs of goods and their parenteral administration, however, are expected to limit the use of monoclonal antibodies in larger populations.

In 2009, the novel swine H1N1 strain caused an unexpected influenza pandemic as a result of reassortment of genes from human, pig, and bird's H1N1 viruses. This past pandemic, together with the ongoing circulation of highly pathogenic avian H5N1 strains and the recent emergence of the H7N9 virus, a new reassortant of avian origin isolated in China, and associated with severe respiratory disease with 40% of mortality, which could potentially adapt for human-to-human transmission, highlighted the vulnerability of the world population to novel influenza strains. Although vaccination remains the main prophylactic strategy for controlling influenza infection, to bridge the period before a new vaccine becomes available and to treat the severe influenza cases, as well as to counter the problem of viral resistance, a wider choice of anti-influenza drugs is required. Development of new influenza antivirals has therefore again become a high priority and an unmet medical need.

Novel influenza antiviral compounds were recently disclosed. WO 2012/144752 discloses phenyl-isoxazol derivative compounds, which are useful as a treatment material for virus infection, especially, infection of an influenza virus, or its pharmaceutically acceptable derivative, a preparation method thereof, and an illness treatment pharmaceutical composition including the compound as an active ingredient. WO 2012/033736 proposes piperazine amide analogues useful in compositions for the prevention and treatment of influenza virus. WO 2011/015037 discloses compounds which exhibit antiviral activity, particularly against influenza virus, and methods of making and using thereof. In one embodiment, the compounds are heterocyclic amides containing piperazine and isozazole rings which are optionally substituted with one or more substituents. The compounds are preferably used to treat or prevent Influenza A infections, such as H1N1, H2N2, H3N2, H5N1, H7N7, H1N2, H9N2, H7N2, H7N3, and H10N7.

However, novel antiviral agents offering an alternative mechanism of action, having low cytotoxicity, and high virus neutralization activity are still in demand. The current invention relates to such compounds that target the stem region of influenza hemagglutinin and which can be used for the prevention and/or the treatment of viral influenza infections.

SUMMARY OF THE INVENTION

The compounds of the present invention have been shown to have a competitive binding activity at least towards HA of the H1 subtype, such as the H1N1 influenza virus strains A/California/07/2009 and A/New Caledonia/20/1999, and towards HA of the H5 subtype, such as the H5N1 influenza strain A/Vietnam/1203/2004. At least some of the compounds of the invention also have been shown to have neutralizing activity against at least two different influenza A virus strains each comprising HA of a different HA subtype from phylogenetic group 1, such as against influenza viruses comprising HA of the H1 subtype, such as the H1N1 influenza virus strains A/California/07/2009 and A/New Caledonia/20/1999, and against influenza virus comprising HA of the H5 subtype, such as the H5N1 influenza strain A/Vietnam/1203/2004. Furthermore, at least some of the compounds of the invention have pharmacokinetic properties like metabolic stability and bioavailability that make them suitable of attaining an antiviral effect in vivo after oral administration.

The current invention provides viral fusion inhibition piperazine derivatives as described in claim 1.

In a first aspect, the present invention provides a compound having formula (I)

$$
\text{A}-\text{Ar}-\overset{\overset{\displaystyle O}{\|}}{\text{C}}-\text{N}\begin{array}{c}R_2\\ \\ R_3\end{array}\text{B}-\text{W}-Y_1-\overset{R_1}{\underset{X}{|}}-Y_2-Z_1\overset{Z_2}{\diagup}
$$

(I)

or a stereo-isomeric, a pharmaceutically acceptable salt, a solvate or a polymorph thereof, wherein:

B is —$CH_2$— or —$CH_2CH_2$—;

W is CH or N;

X is $CR_4$ or N;

$Y_1$ is —$(CH_2)_p$—, wherein p is 0, 1, 2 or 3 and $Y_2$ is —$(CH_2)_q$—, wherein q is 0, 1, 2 or 3;

$Z_1$ and $Z_2$ are CH or N, wherein at least $Z_1$ or $Z_2$ is CH;

$R_1$ is hydrogen, —$CH_2OH$, —$CH_2OCH_3$, —$C(O)CH_3$, —$C(O)OCH_3$, —$C(O)OCH_2CH_3$, —$C(O)NH_2$, —$C(O)NH(CH_2)_2OCH_3$, —$C(O)NH(CH_3)_m$, —$C(O)NH(CH_2)_nCH_3$ or —$C(O)NH(CH_2)_oNH_2$, wherein m is 1 or 2 and wherein n and o are 2 or 3, or a carbo- or heterocyclic radical selected from cyclohexyl, pyridyl, pyrrolyl, oxazolyl, oxadiazolyl, pyrazolyl, triazolyl, tetrazolyl, thiadiazolyl and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone, and $R_4$ is hydrogen, methyl, ethyl or propyl; or $R_1$, X and $R_4$ are taken together to form a carbo- or heterocycle;

$R_2$ is hydrogen, methyl, —$C(O)NH_2$, —$CH_2C(O)NH_2$ and $R_3$ is hydrogen; or wherein $R_2$ and $R_3$ are taken together to form 1,2-ethanediyl or 1,3-propanediyl;

Ar is a 5-membered aromatic or heteroaromatic ring, a 6-membered aromatic or heteroaromatic ring, optionally substituted with one or more halogen;

A is benzyl, benzothiazolyl, benzoxazolyl, benzisoxazolyl, benzofuranyl, isoquinolinyl, quinazolyl, benzimidazolyl, pyridooxazolyl or methoxyphenyl acetamide, optionally substituted with one or more substituents independently selected from halogen, —OH, —O—$CH_3$, —$CH_3$, —$CF_3$, —$OCF_3$, —$NH_2$, —$NCH_3$, —$N(CH_3)_2$, —$NC(O)CH_3$, —$NSO_2CH_3$, cyclopropoxy or methanesulfonyl nitrile.

Such compounds show efficient virus binding and neutralization activity towards a representative set of influenza viruses, while exhibiting no or acceptably low cytotoxicity.

Without limiting to any mechanism, it is assumed that the compounds described herein bind to the stem region, i.e. the viral membrane proximal part, of influenza hemagglutinin, to a binding site that is similar to or at least overlapping with the binding epitope of well-characterized hemagglutinin binding proteins such as e.g. CR9114 (WO2013/007770), CR6261 (WO2008/028946), and HB80.4 (Whitehead et al., Nat Biotechnol. 2012 May 27; 30(6):543-8). In particular embodiments, the compounds bind to the shallow groove at the interface of the hemagglutinin HA1 and HA2 chains in the vicinity of residues His18, His38, Val40, Leu292, Thr318 of the HA1 chain and Val18, Gly20, Trp21, Thr41, Ile45, Ile48, Thr49, Val52, Asn53, and Ile56 of the HA2 chain, and interfere with the conformational change that the hemagglutinin stem region needs to undergo to accommodate the fusion of the viral and host cell membranes.

The invention further relates to methods of producing said compounds, pharmaceutical compositions comprising said compounds, and said compounds for use as a medicine, especially for the prevention and/or the treatment of viral influenza infections.

DETAILED DESCRIPTION OF THE INVENTION

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the following terms have the following meanings:

"A", "an", and "the" as used herein refers to both singular and plural referents unless the context clearly dictates otherwise. By way of example, "a compartment" refers to one or more than one compartment.

"About" as used herein referring to a measurable value such as a parameter, an amount, a temporal duration, and the like, is meant to encompass variations of +/−20% or less, preferably +/−10% or less, more preferably +/−5% or less, even more preferably +/−1% or less, and still more preferably +/−0.1% or less of and from the specified value, in so far such variations are appropriate to perform in the disclosed invention. However, it is to be understood that the value to which the modifier "about" refers is itself also specifically disclosed.

"Comprise," "comprising," and "comprises" and "comprised of" as used herein are synonymous with "include", "including", "includes" or "contain", "containing", "contains" and are inclusive or open-ended terms that specifies the presence of what follows e.g. component and do not exclude or preclude the presence of additional, non-recited components, features, element, members, steps, known in the art or disclosed therein.

The term "neutralizing" or "neutralization" as used herein in relation to compounds of the invention refers to the ability of a compound to inhibit an influenza virus from replication, in vitro and/or in vivo within a subject, regardless of the mechanism by which neutralization is achieved. In some embodiments, the compounds of the invention neutralize influenza virus through the inhibition of the fusion of viral and cellular membranes following attachment of the virus to the target cell. The term "cross-neutralizing" or "cross-neutralization" as used herein in relation to the compounds of the invention refers to the ability to neutralize influenza virus strains of different subtypes of influenza A. Neutralizing activity can for instance be measured as described herein. Alternative assays measuring neutralizing activity are described in for instance WHO Manual on Animal Influenza Diagnosis and Surveillance, Geneva: World Health Organisation, 2005, version 2002.5. Typically, the compounds of the invention have a pEC50 of 6 or more, preferably 7 or more, more preferably 8 or more, as determined in an in vitro virus neutralization assay (VNA), e.g. as described in the Examples.

The recitation of numerical ranges by endpoints includes all numbers and fractions subsumed within that range, as well as the recited endpoints. All percentages are to be understood as percentage by weight and are abbreviated as "% wt.", unless otherwise defined or unless a different meaning is obvious to the person skilled in the art from its use and in the context wherein it is used.

Compounds

The compounds of the present invention have been shown to have a competitive binding activity at least towards influenza viruses comprising HA of the H1 subtype, such as the H1N1 influenza virus strains A/California/07/2009 and A/New Caledonia/20/1999, and towards influenza viruses comprising HA of the H5 subtype, such as the H5N1 influenza strain A/Vietnam/1203/2004. At least some of the compounds of the invention also have been shown to have neutralizing activity against at least two different influenza A virus strains each comprising HA of a different HA subtype from phylogenetic group 1, such as against influenza viruses comprising HA of the H1 subtype, such as the H1N1 influenza virus strains A/California/07/2009 and A/New Caledonia/20/1999, and against influenza virus comprising HA of the H5 subtype, such as the H5N1 influenza strain A/Vietnam/1203/2004. Furthermore, at least some of the compounds of the invention have pharmacokinetic properties like metabolic stability and bioavailability that make them suitable of attaining an antiviral effect in vivo after oral administration.

In a first aspect, the present invention provides a compound having formula (I)

(I)

[Chemical structure showing: A—Ar—C(=O)—N ring with $R_2$, $R_3$, B, W, $Y_1$, X, $Y_2$, $Z_1$, $Z_2$, $R_1$ substituents]

or a stereo-isomeric, a pharmaceutically acceptable salt, a solvate or a polymorph thereof, wherein:

B is —$CH_2$— or —$CH_2CH_2$—;
W is CH or N;
X is $CR_4$ or N;

$Y_1$ is —$(CH_2)_p$—, wherein p is 0, 1, 2 or 3 and $Y_2$ is —$(CH_2)_q$—, wherein q is 0, 1, 2 or 3;

$Z_1$ and $Z_2$ are CH or N, wherein at least $Z_1$ or $Z_2$ is CH;

$R_1$ is hydrogen, —$CH_2OH$, —$CH_2OCH_3$, —$C(O)CH_3$, —$C(O)OCH_3$, —$C(O)OCH_2CH_3$, —$C(O)NH_2$, —$C(O)NH(CH_2)_2OCH_3$, —$C(O)NH(CH_3)_m$, —$C(O)NH(CH_2)_nCH_3$ or —$C(O)NH(CH_2)_oNH_2$, wherein m is 1 or 2 and wherein n and o are 2 or 3, or a carbo- or heterocyclic radical selected from cyclohexyl, pyridyl, pyrrolyl, oxazolyl, oxadiazolyl, pyrazolyl, triazolyl, tetrazolyl, thiadiazolyl and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone, and $R_4$ is hydrogen, methyl, ethyl or propyl; or $R_1$, X and $R_4$ are taken together to form a carbo- or heterocycle;

$R_2$ is hydrogen, methyl, —$C(O)NH_2$, —$CH_2C(O)NH_2$ and $R_3$ is hydrogen; or wherein $R_2$ and $R_3$ are taken together to form 1,2-ethanediyl or 1,3-propanediyl;

Ar is a 5-membered aromatic or heteroaromatic ring, a 6-membered aromatic or heteroaromatic ring, optionally substituted with one or more halogen;

A is benzyl, benzothiazolyl, benzoxazolyl, benzisoxazolyl, benzofuranyl, isoquinolinyl, quinazolyl, benzimidazolyl, pyridooxazolyl or methoxyphenyl acetamide, optionally substituted with one or more substituents independently selected from halogen, —OH, —O—$CH_3$, —$CH_3$, —$CF_3$, —$OCF_3$, —$NH_2$, —$NCH_3$, —$N(CH_3)_2$, —$NC(O)CH_3$, —$NSO_2CH_3$, cyclopropoxy or methanesulfonyl nitrile.

In a preferred embodiment, W is N.

In a preferred embodiment, B is —$CH_2$— and $R_3$ is hydrogen.

In a preferred embodiment, $R_2$ is hydrogen, methyl, —$C(O)NH_2$, —$CH_2C(O)NH_2$ and $R_3$ is hydrogen.

In a preferred embodiment, X is $CR_4$. Preferably, $R_4$ is hydrogen or methyl, and more preferably $R_4$ is hydrogen.

In a preferred embodiment, p and/or q is 0. More preferably, p and q are 0.

In a preferred embodiment, $Z_1$ and $Z_2$ are CH.

In a preferred embodiment, $R_1$ is a carbo- or heterocyclic radical selected from cyclohexyl, pyridyl, pyrrolyl, oxazolyl, oxadiazolyl, pyrazolyl, triazolyl, tetrazolyl, thiadiazolyl and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone.

Preferably, $R_1$ is a heterocyclic radical selected from oxadiazolyl, triazolyl and tetrazolyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone. More preferably, $R_1$ is a heterocyclic radical selected from oxadiazolyl, triazolyl and tetrazolyl substituted with methyl, ethyl or methoxy.

In a preferred embodiment, A is benzoxazol-2-yl, optionally substituted with one or more substituents independently selected from halogen, —OH, —$OCH_3$, —$CH_3$, —$CF_3$, —$OCF_3$, —$NH_2$, —$NCH_3$, —$N(CH_3)_2$, —$NC(O)CH_3$, —$NSO_2CH_3$, cyclopropoxy or methanesulfonyl nitrile. In the framework of this application, halogen is a substituent selected from the group of fluoro, chloro, bromo and iodo. Preferably, halogen is fluoro or chloro.

Preferably, said benzoxazol-2-yl comprises a substituent in the 5-position, wherein said substituent is selected from —$OCH_3$, —$CF_3$, —$OCF_3$, —$NH_2$, —$NCH_3$, —$N(CH_3)_2$, —$NC(O)CH_3$ or cyclopropoxy. More preferably, said substituent is selected from —$OCF_3$, —$NC(O)CH_3$ or cyclopropoxy.

In a preferred embodiment, Ar is phenyl, furan-2-yl or pyridinediyl optionally substituted with one or more fluoro. In a more preferred embodiment, Ar selected from 1,3-phenyl, 1,5-(2-fluoro)-phenyl, 1,5-(3-fluoro)-phenyl, 2,5-furanyl, 2,4-pyridinediyl or 2,6-pyridinediyl. Most preferably, Ar is selected from 1,3-phenyl or 2,6-pyridinediyl.

The "pharmaceutically acceptable salts" as mentioned hereinbefore or hereinafter are meant to comprise the therapeutically active non-toxic acid addition salt forms which the compounds according to formula (I) are able to form. Said acid addition salts can be obtained by treating the base form of the compounds according to formula (I) with appropriate acids, for example inorganic acids, for example hydrohalic acid, in particular hydrochloric acid, hydrobromic acid, sulfuric acid, nitric acid and phosphoric acid; organic acids, for example acetic acid, hydroxyacetic acid, propanoic acid, lactic acid, pyruvic acid, oxalic acid, malonic acid, succinic acid, maleic acid, fumaric acid, malic acid, tartaric acid, citric acid, methanesulfonic acid, ethanesulfonic acid, benzenesulfonic acid, p-toluenesulfonic acid, cyclamic acid, salicyclic acid, p-aminosalicylic acid and pamoic acid.

The compounds of formula (I) containing acidic protons may be converted into their therapeutically active non-toxic metal or amine addition salt forms by treatment with appropriate organic and inorganic bases. The pharmaceutically acceptable salts as mentioned hereinbefore or hereinafter are meant to also comprise the therapeutically active non-toxic metal or amine addition salt forms (base addition salt forms) which the compounds of formula (I) are able to form. Appropriate base addition salt forms comprise, for example, the ammonium salts, the alkali and earth alkaline metal salts, e.g. the lithium, sodium, potassium, magnesium, calcium salts and the like, salts with organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, the benzathine, N-methyl-D-glucamine, 2-amino-2-(hydroxymethyl)-1,3-propanediol, hydrabamine salts, and salts with amino acids such as, for example, arginine, lysine and the like. Conversely, said acid or base addition salt forms can be converted into the free forms by treatment with an appropriate base or acid.

The term "pharmaceutically acceptable salt" also comprises the quaternary ammonium salts (quaternary amines) which the compounds of formula (I) are able to form by reaction between a basic nitrogen of a compound of formula (I) and an appropriate quaternizing agent, such as, for example, an optionally substituted C1-6 alkyl halide, aryl C1-6 alkyl halide, C1-6 alkyl carbonyl halide, aryl carbonyl halide, Het-C1-6 alkyl halide or Het-carbonyl halide, e.g. methyl iodide or benzyl iodide. Preferably, "Het" represents a monocyclic heterocycle selected from furanyl or thienyl; or a bicyclic heterocycle selected from benzofuranyl or benzothienyl; each monocyclic and bicyclic heterocycle may optionally be substituted with 1, 2 or 3 substituents, each substituent independently selected from the group of halogen, alkyl and aryl. Preferably, the quaternizing agent is C1-6 alkyl halide. Other reactants with good leaving groups may also be used, such as C1-6 alkyl trifluoromethane sulfonates, C1-6 alkyl methane sulfonates, and C1-6 alkyl p-toluene sulfonates. A quaternary amine has a positively charged nitrogen. Pharmaceutically acceptable counter ions include chloro, bromo, iodo, trifluoro acetate, acetate, triflate, sulfate, sulfonate. Preferably, the counter ion is iodo. The counter ion of choice can be introduced using ion exchange resins.

In this context, alkyl is a straight or branched saturated hydrocarbon radical having from 1 to 6 carbon atoms; or is a cyclic saturated hydrocarbon radical having from 3 to 6 carbon atoms; or is a cyclic saturated hydrocarbon radical having from 3 to 6 carbon atoms attached to a straight or branched saturated hydrocarbon radical having from 1 to 6 carbon atoms; wherein each carbon atom can be optionally substituted with cyano, hydroxy, C1-6 alkyloxy or oxo. Preferably alkyl is a straight or branched saturated hydrocarbon radical having from 1 to 6 carbon atoms; or is a cyclic saturated hydrocarbon radical having from 3 to 6 carbon atoms; wherein each carbon atom can be optionally substituted with hydroxyl or C1-6 alkyloxy. Preferably, alkyl is methyl, ethyl or cyclohexyl methyl, more preferably methyl or ethyl. An interesting embodiment of alkyl in all definitions used hereinbefore or hereinafter is C1-6 alkyl which represents a straight or branched saturated hydrocarbon radical having from 1 to 6 carbon atoms such as for example methyl, ethyl, propyl, 2-methyl-ethyl, pentyl, hexyl and the like. A preferred subgroup of C1-6 alkyl is C1-4 alkyl which represents a straight or branched saturated hydrocarbon radical having from 1 to 4 carbon atoms such as for example methyl, ethyl, propyl, 2-methyl-ethyl and the like.

The term "solvate" comprises the hydrates and solvent addition forms which the compounds of formula (I) are able to form, as well as the salts thereof. Examples of such forms are e.g. hydrates, alcoholates and the like.

The term "polymorph" refers to the ability of the compound of the invention to exist in more than one form or crystal structure.

In the context of this application, a compound according to the invention is inherently intended to comprise all stereochemically isomeric forms thereof. The term "stereochemically isomeric forms" as used hereinbefore or hereinafter defines all the possible stereoisomeric forms which the compounds of formula (I), and their N-oxides, pharmaceutically acceptable salts, solvates or physiologically functional derivatives may possess. Unless otherwise mentioned or indicated, the chemical designation of compounds denotes the mixture of all possible stereochemically isomeric forms. In particular, stereogenic centers may have the R- or S-configuration; substituents on bivalent cyclic (partially) saturated radicals may have either the cis- or trans-configuration. Compounds encompassing double bonds can have an E (entgegen)- or Z (zusammen)-stereochemistry at said double bond. The terms cis, trans, R, S, E and Z are well known to a person skilled in the art. Stereochemically isomeric forms of the compounds of formula (I) are obviously intended to be embraced within the scope of this invention. Of special interest are those compounds of formula (I) which are stereochemically pure.

Following CAS-nomenclature conventions, when two stereogenic centres of known absolute configuration are present in a molecule, an R or S descriptor is assigned (based on Cahn-Ingold-Prelog sequence rule) to the lowest-numbered chiral centre, the reference centre. The configuration of the second stereogenic centre is indicated using relative descriptors [R*,R*] or [R*,S*], where Rx is always specified as the reference centre and [R*,R*] indicates centres with the same chirality and [R*,S*] indicates centres of unlike chirality. For example, if the lowest-numbered chiral centre in the molecule has an S configuration and the second centre is R, the stereo descriptor would be specified as S-[R*,S*]. If "α" and "β" are used: the position of the highest priority substituent on the asymmetric carbon atom in the ring system having the lowest ring number, is arbitrarily always in the "α" position of the mean plane determined by the ring system. The position of the highest priority substituent on the other asymmetric carbon atom in the ring system relative to the position of the highest priority substituent on the reference atom is denominated "α", if it is on the same side of the mean plane determined by the ring system, or "β", if it is on the other side of the mean plane determined by the ring system.

When a specific stereoisomeric form is indicated, this means that said form is substantially free, i.e. associated with less than 50%, preferably less than 20%, more preferably less than 10%, even more preferably less than 5%, further preferably less than 2% and most preferably less than 1% of the other isomer(s). Thus, when a compound of formula (I) is for instance specified as (R,S), this means that the compound is substantially free of the (S,R) isomer. Compounds of formula (I) and some of the intermediate compounds invariably have at least two stereogenic centres in their structure which may lead to at least 4 stereochemically different structures.

The compounds of formula (I) may be synthesized in the form of mixtures, in particular racemic mixtures, of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The tautomeric forms of the compounds of formula (I) are meant to comprise those compounds of formula (I) wherein e.g. an enol group is converted into a keto group (keto-enol tautomerism). Tautomeric forms of the compounds of formula (I) or of intermediates of the present invention are intended to be embraced by the ambit of this invention.

The N-oxide forms of the present compounds are meant to comprise the compounds of formula (I) wherein one or several tertiary nitrogen atoms are oxidized to the so-called N-oxide. The compounds of formula (I) may be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. t-butyl hydro-peroxide. Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

In the framework of this application, a compound according to the invention is inherently intended to comprise all isotopic combinations of its chemical elements. In the framework of this application, a chemical element, in particular when mentioned in relation to a compound according to formula (I), comprises all isotopes and isotopic mixtures of this element, either naturally occurring or synthetically produced, either with natural abundance or in an isotopically enriched form. In particular, when hydrogen is mentioned, it is understood to refer to $^1H$, $^2H$, $^3H$ and mixtures thereof; when carbon is mentioned, it is understood to refer to $^{11}C$, $^{12}C$, $^{13}C$, $^{14}C$ and mixtures thereof; when nitrogen is mentioned, it is understood to refer to $^{13}N$, $^{14}N$, $^{15}N$ and mixtures thereof; when oxygen is mentioned, it is understood to refer to $^{14}O$, $^{15}O$, $^{16}O$, $^{17}O$, $^{18}O$ and mixtures thereof; and when fluoro is mentioned, it is understood to refer to $^{18}F$, $^{19}F$ and mixtures thereof. A compound according to the invention therefore inherently comprises a compound with one or more isotopes of one or more element, and mixtures thereof, including a radioactive compound, also called radio labelled compound, wherein one or more nonradioactive atoms has been replaced by one of its radioactive isotopes. By the term "radio labelled compound" is meant any compound according to formula (Ia) or (Ib), a pharmaceutically acceptable salt thereof or an N-oxide form thereof or a solvate thereof, which contains at least one radioactive atom. For example, a compound can be labelled with positron or with gamma emitting radioactive isotopes. For radioligand-binding techniques (membrane receptor assay), the $^3H$-atom or the $^{125}I$-atom is the atom of choice to be replaced. For imaging, the most commonly used positron emitting (PET) radioactive isotopes are $^{11}C$, $^{18}F$, $^{15}O$ and $^{13}N$, all of which are accelerator produced and have half-lives of 20, 100, 2 and 10 minutes respectively. Since the half-lives of these radioactive isotopes are so short, it is only feasible to use them at institutions which have an accelerator on site for their production, thus limiting their use. The most widely used of these are $^{18}F$, $^{99m}Tc$, $^{201}Tl$ and $^{123}I$. The handling of these radioactive isotopes, their production, isolation and incorporation in a molecule are known to the skilled person. In particular, the radioactive atom is selected from the group of hydrogen, carbon, nitrogen, sulfur, oxygen and halogen. Preferably, the radioactive atom is selected from the group of hydrogen, carbon and halogen. In particular, the radioactive isotope is selected from the group of $^3H$, $^{11}C$, $^{18}F$, $^{122}I$, $^{123}I$, $^{125}I$, $^{131}I$, $^{75}Br$, $^{76}Br$, $^{77}Br$ and $^{82}Br$. Preferably, the radioactive isotope is selected from the group of $^3H$, $^{11}C$ and $^{18}F$.

Particularly preferred embodiments according to the present invention are the compounds selected from:

(1)
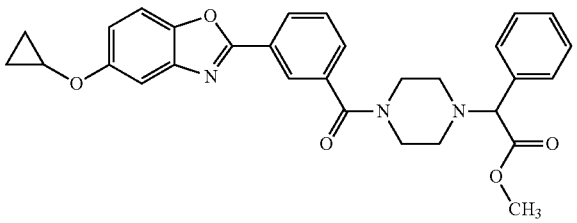 [SMILES: COC(=O)C(c1ccccc1)N1CCN(C(=O)c2cccc(-c3nc4cc(OC5CC5)ccc4o3)c2)CC1]

(2)
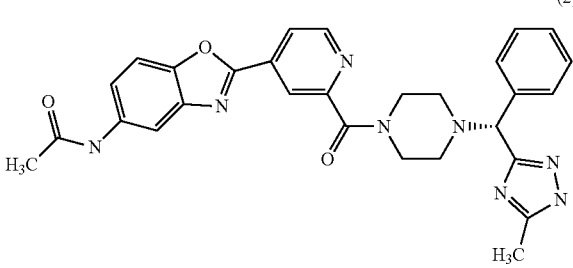

(3)
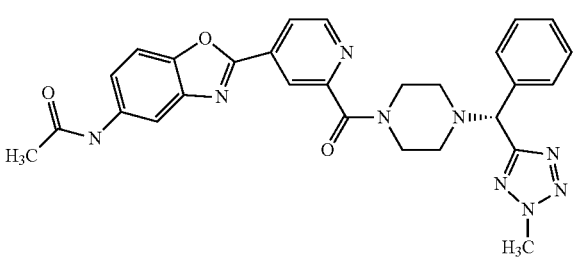

(4)
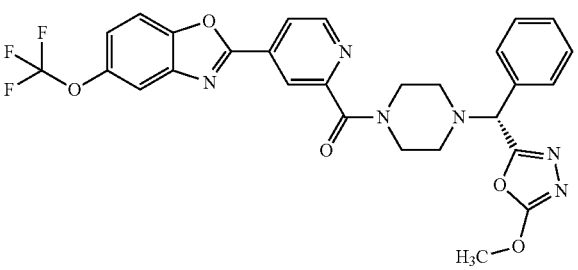

(5)
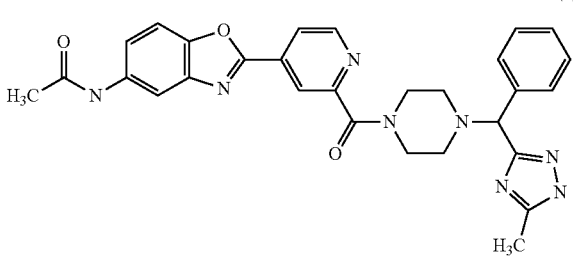

-continued (6)

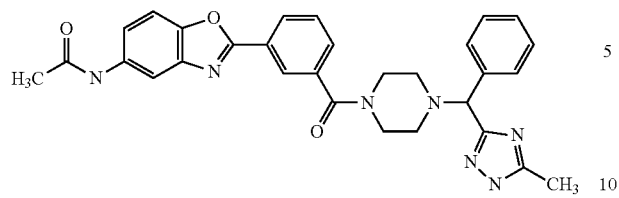

-continued

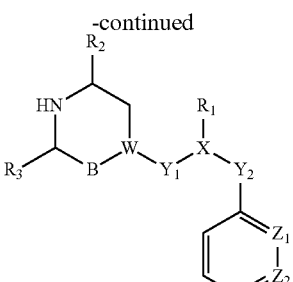

Ib (12)

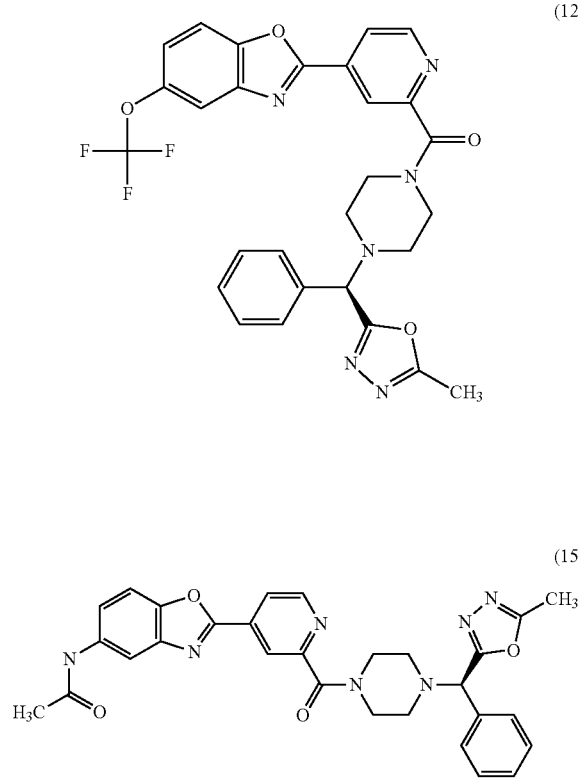

(15)

Other preferred embodiments of the compounds covered by the current invention are listed in Tables 1 and 2.

Preparation of Compounds

In a second aspect, the present invention relates to a method of preparing a compound according to the first aspect of the invention, comprising the step of reacting an intermediate of the formula Ia with an intermediate of the formula Ib in the presence of a suitable base and a suitable solvent, wherein all variables A, B, $R_1$, $R_2$, $R_3$, $R_4$, Ar, W, X, $Y_1$, $Y_2$, $Z_1$ and $Z_2$ are as defined in claim 1 and wherein L represents a suitable leaving group.

The reaction is schematically depicted as Rx 1.

Rx 1

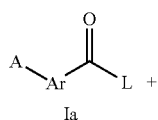

Suitable solvents are, for example, water, lower alcohols, e.g. ethanol and the like, hydrocarbons, e.g. toluene, ketones, e.g. 2-butanone, halogenated hydrocarbons, e.g. dichloromethane, and mixtures of such solvents.

Suitable bases are alkali and earth alkaline metal hydroxides, e.g. lithium hydroxide, sodium hydroxide, potassium hydroxide, magnesium hydroxide and the like; alkali and earth alkaline metal carbonates, e.g. lithium carbonate, sodium carbonate, potassium carbonate, magnesium carbonate and the like; organic bases, e.g. primary, secondary and tertiary aliphatic and aromatic amines such as methylamine, ethylamine, propylamine, isopropylamine, the four butylamine isomers, dimethylamine, diethylamine, diethanolamine, dipropylamine, diisopropylamine, di-n-butylamine, pyrrolidine, piperidine, morpholine, trimethylamine, triethylamine, tripropylamine, quinuclidine, pyridine, quinoline and isoquinoline, benzathine, N-methyl-D-glucamine, 2-amino-2-(hydroxymethyl)-1,3-propanediol, and the like.

Suitable leaving groups L are dinitrogen, dialkyl ether, perfluoroalkyl sulfonate (such as triflate), tosylate, mesylate, iodide, bromide, chloride, fluoride, water, alcohol, nitrate, phosphate, thiolate, amine, ammonia, carboxylate, phenoxide, hydroxide and alkoxide.

In a preferred embodiment, the present invention provides a method according to the second aspect of the invention, comprising the step of isolating an enantiomerically pure form of compound I.

It is considered within the knowledge of the skilled man to explore the appropriate temperatures, dilutions, and reaction times in order to optimize the above reactions in order to obtain a desired compound.

Pharmaceutical Compositions

In a third aspect, the present invention relates to a pharmaceutical composition comprising as active ingredient a compound according to the first aspect of the invention.

The compounds of the present invention may be administered as crystalline or amorphous products. They may be obtained for example as solid plugs, powders, or films by methods such as precipitation, crystallization, freeze drying, spray drying, or evaporative drying. They may be administered alone or in combination with one or more other compounds of the invention or in combination with one or more other drugs. Generally, they will be administered as a formulation in association with one or more pharmaceutically acceptable excipients. The term "excipient" is used herein to describe any ingredient other than the compound(s) of the invention. The choice of excipient depends largely on factors such as the particular mode of administration, the effect of the excipient on solubility and stability, and the nature of the dosage form.

In a fourth aspect, the present invention relates to a method of preparing a pharmaceutical composition according to the third aspect of the invention comprising the step of intimately mixing a pharmaceutically acceptable carrier with a therapeutically effective amount of a compound according to the first aspect of the invention.

The compounds of the present invention or any subgroup thereof may be formulated into various pharmaceutical forms for administration purposes. As appropriate compositions there may be cited all compositions usually employed for systemically administering drugs. To prepare the pharmaceutical compositions of this invention, an effective amount of the particular compound, optionally in addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, for example, for oral, rectal, or percutaneous administration. For example, in preparing the compositions in oral dosage form, any of the usual pharmaceutical media may be employed such as, for example, water, glycols, oils, alcohols and the like in the case of oral liquid preparations such as suspensions, syrups, elixirs, emulsions, and solutions; or solid carriers such as starches, sugars, kaolin, diluents, lubricants, binders, disintegrating agents and the like in the case of powders, pills, capsules, and tablets. Because of their ease in administration, tablets and capsules represent the most advantageous oral dosage unit forms, in which case solid pharmaceutical carriers are obviously employed. Also included are solid form preparations that can be converted, shortly before use, to liquid forms. In the compositions suitable for percutaneous administration, the carrier optionally comprises a penetration enhancing agent and/or a suitable wetting agent, optionally combined with suitable additives of any nature in minor proportions, which additives do not introduce a significant deleterious effect on the skin. Said additives may facilitate the administration to the skin and/or may be helpful for preparing the desired compositions. These compositions may be administered in various ways, e.g., as a transdermal patch, as a spot-on, as an ointment. The compounds of the present invention may also be administered via inhalation or insufflation by means of methods and formulations employed in the art for administration via this way. Thus, in general the compounds of the present invention may be administered to the lungs in the form of a solution, a suspension or a dry powder.

It is especially advantageous to formulate the aforementioned pharmaceutical compositions in unit dosage form for ease of administration and uniformity of dosage. Unit dosage form as used herein refers to physically discrete units suitable as unitary dosages, each unit containing a predetermined quantity of active ingredient calculated to produce the desired therapeutic effect in association with the required pharmaceutical carrier. Examples of such unit dosage forms are tablets (including scored or coated tablets), capsules, pills, powder packets, wafers, suppositories, injectable solutions or suspensions and the like, and segregated multiples thereof.

In general, it is contemplated that an effective daily amount would be from 0.01 mg/kg to 100 mg/kg body weight, more preferably from 0.1 mg/kg to 20 mg/kg body weight. It may be appropriate to administer the required dose as two, three, four or more sub-doses at appropriate intervals throughout the day. Said sub-doses may be formulated as unit dosage forms, for example, containing 1 to 1000 mg, and in particular 5 to 200 mg of active ingredient per unit dosage form.

The exact dosage and frequency of administration depends on the particular compound of formula (I) used, the particular condition being treated, the severity of the condition being treated, the age, weight and general physical condition of the particular patient as well as other medication the individual may be taking, as is well known to those skilled in the art. Furthermore, it is evident that the effective amount may be lowered or increased depending on the response of the treated subject and/or depending on the evaluation of the physician prescribing the compounds of the instant invention. The effective amount ranges mentioned above are therefore only guidelines and are not intended to limit the scope or use of the invention to any extent.

Medical Use

In a fifth aspect, the present invention relates to a compound according to the first aspect of the invention for use as a medicine. Furthermore, the present invention relates to a composition according to the third aspect of the invention for use as a medicine.

In a sixth aspect, the present invention relates to a compound according to the first aspect of the invention for use in preventing and/or treating influenza. Furthermore, the present invention relates to a composition according to the third aspect of the invention for use in preventing and/or treating influenza.

In a preferred embodiment, the present invention relates to a compound according to the first aspect of the invention for use in preventing and/or treating influenza related to infection by an influenza A virus strain, comprising hemagglutinin of a subtype from phylogenetic group 1. More preferably, the invention relates to a compound, wherein the compound binds to the stem region of hemagglutinin. Even more preferably, said compound inhibits the conformational change of the hemagglutinin stem region at low pH.

EXAMPLES

The following examples are intended to further clarify the present invention, and are nowhere intended to limit the scope of the present invention.

Preparation of Compounds of Formula (I)

Synthesis of Compound 1

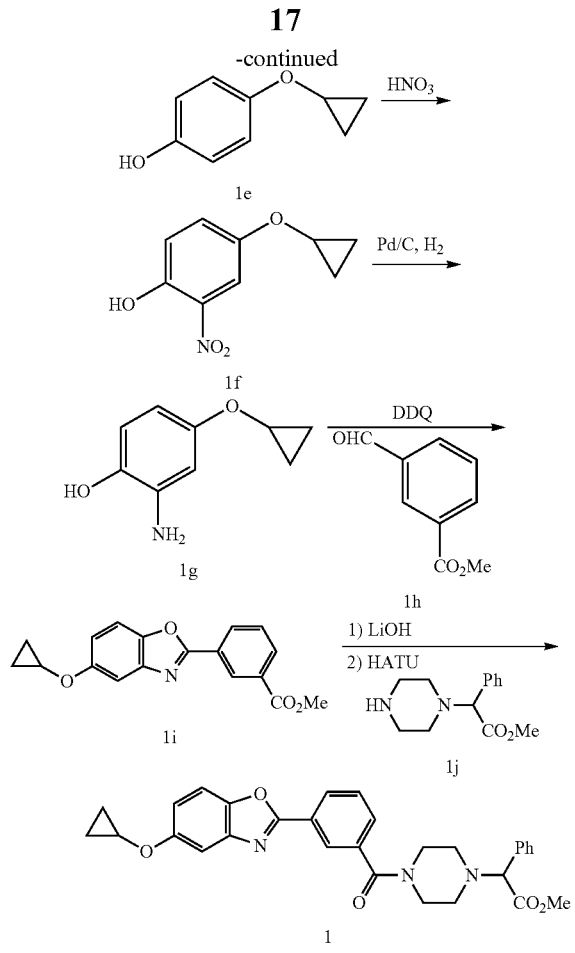

1-(Benzyloxy)-4-(2-bromoethoxy)benzene (1b). Potassium carbonate (17.3 g, 125 mmol, 2.5 eq.) was added to a mixture of 4-benzyloxyphenol 1a (10 g, 50 mmol, 1 eq.) in MeCN (50 ml) and dibromoethane (26 ml, 300 mmol, 6 eq.). The resulting heterogeneous mixture was stirred overnight at 100° C. After cooling down to room temperature, ethyl acetate was added and the mixture was filtered over a pad of Celite. The cake was washed with ethyl acetate and the filtrate was concentrated to dryness. The crude mixture was purified by automated silica gel chromatography (from 5% to 15% EtOAc in heptanes) to afford product 1b as a bright white solid (12.1 g, 79% yield). $^1$HNMR: (300 MHz, CHLOROFORM-d) 7.25-7.42 (m, 5H) 6.81-6.97 (m, 4H) 5.02 (s, 2H) 4.24 (t, 2H) 3.61 (t, 2H).

1-(Benzyloxy)-4-(vinyloxy)benzene (1c). Potassium tert-butoxide (5.3 g, 47.2 mmol, 1.2 eq.) was added portion wise to a solution of 1b (12.1 g, 39.4 mmol, 1 eq.) in THF (150 ml) at room temperature. A creamy coloured precipitate formed and the resulting reaction mixture was stirred overnight at room temperature. The reaction was quenched with brine and extracted three times with EtOAc. The organic layers were dried over sodium sulfate, filtered and concentrated to dryness to afford 1c as a clear oil that slowly crystallized (9 g, quantitative yield). The material was pure enough to be used in the next step without any further purification.

1-(Benzyloxy)-4-cyclopropoxybenzene (1d). Diethylzinc (1 N in hexanes, 50.4 ml, 50.4 mmol, 1.26 eq.) was slowly (over 20 min) added via a dropping funnel to a cooled (−10° C.) solution of is (9 g, 39.8 mmol, 1 eq.) and chlor-oiodomethane (9 ml, 119.3 mmol, 3 eq.) in dichloroethane (135 ml). The reaction was exothermic and a precipitate formed. After completion of the addition the reaction was stirred overnight at room temperature. The reaction was quenched with a saturated aqueous solution of ammonium chloride and the aqueous layer was extracted three times with DCM. The organic layers were dried over $Na_2SO_4$, filtered and concentrated to dryness. The crude oil was filtered through a plug of silica gel (eluting with 10% EtOAc in heptanes) to ensure full elimination of zinc salts. Compound 1d was isolated as a clear oil that crystallized upon standing as a white solid (7 g, 73% yield). $^1$HNMR: (300 MHz, CHLOROFORM-d) 7.22-7.45 (m, 5H) 6.86-7.02 (m, 4H) 5.02 (s, 2H) 3.63-3.72 (m, 1H) 0.71-0.82 (m, 4H).

4-Cyclopropoxyphenol (1e). Pd/C (10% w/w, 0.7 g) was added in one portion to a solution of 1d (7 g, 29.13 mmol, 1 eq.) in a 1/1 mixture of AcOEt/AcOH (80 ml). The heterogeneous mixture was transferred to a Parr vessel and the hydrogen pressure was adjusted to 5 bars and the reaction mixture was stirred for 20 h at room temperature. The black mixture was filtered through a pad of Celite and the filtrate was concentrated to dryness to afford 1e as a dark solid (4.32 g, quantitative yield). $^1$HNMR: (300 MHz, CHLOROFORM-d) 6.92 (d, 2H), 6.76 (d, 2H), 4.78 (bs, 1H), 3.63-3.72 (m, 1H), 0.65-0.78 (m, 4H).

4-Cyclopropoxy-2-nitrophenol (1f). N-bromosuccinimide and silver nitrate were mixed in acetonitrile at 70° C. then the resulting white turbid solution was added over 15 min to a stirred solution of 1e in acetonitrile at 80° C. The conversion of the starting material was followed by TLC (5% EtOAc in heptanes) and after 1 h stirring at 80° C. the mixture was concentrated to dryness. The resulting dark crude mixture was purified by automated silica gel chromatography (from 1% to 5% AcOEt in heptanes) to afford product if as a yellow solid (1.35 g, 25% yield). $^1$HNMR: (300 MHz, CHLOROFORM-d) 10.36 (s, 1H), 7.78 (s, 1H), 7.24 (d, 1H) 7.15 (d, 1H), 4.78 (bs, 1H), 3.65-3.79 (m, 1H), 0.71-0.92 (m, 4H).

2-Amino-4-cyclopropoxyphenol (1g). Pd/C (135 mg, 10% w/w) was added in one portion to a solution of if (1.35 g, 6.9 mmol) in methanol (25 ml). A balloon of hydrogen was adapted to the flask and the resulting heterogeneous mixture was stirred overnight at room temperature. The reaction mixture was filtered through a pad of Celite and the filtrate was concentrated to afford a dark brown sticky solid. Purification by silica gel chromatography using a gradient of eluent from 10% to 20% MeOH in DCM afforded the corresponding amino-phenol 1g as a brown solid (0.8 g, 70% yield). $^1$HNMR: (300 MHz, $CD_3OD$) 6.59 (d, 1H), 6.48 (d, 1H), 6.24-6.32 (m, 1H), 3.59-3.68 (m, 1H), 0.57-0.73 (m, 4H).

Methyl 3-(5-cyclopropoxybenzo[d]oxazol-2-yl)benzoate (1i). Compound 1 g (460 mg, 2.765 mmol, 1 eq.) and methyl 3-formylbenzoate 1h (454 mg, 2.765 mmol, 1 eq.) were mixed in methanol (10 ml) and the homogeneous mixture was stirred at 80° C. for 2 h until full conversion towards the imine was observed. After concentration to dryness the corresponding imine was dissolved in DCM (15 ml) and DDQ (753.2 mg, 3.32 mmol, 1.2 eq.) was added in one portion. The corresponding mixture was stirred overnight at room temperature then filtered over a pad of Celite followed by washing with DCM. The filtrate was concentrated to dryness. The crude product was purified by automated silica gel chromatography to afford the corresponding benzoxazole 1i as a clear pink solid (450 mg, 53% yield). $^1$HNMR: (300 MHz, CHLOROFORM, d) 8.90 (s, 1H), 8.45 (d, 1H), 8.22 (d, 1H), 7.59-7.70 (m, 1H), 7.55 (s, 1H), 7.48 (d, 1H), 7.02 (dd, 1H,) 3.95 (s, 3H), 3.75-3.83 (m, 1H), 0.80-0.85 (m, 4H).

Methyl 2-(4-(3-(5-cyclopropoxybenzo[d]oxazol-2-yl)benzoyl)piperazin-1-yl)-2-phenylacetate. Lithium hydroxide monohydrate (73 mg, 1.75 mmol, 1.2 eq.) was added to a mixture of 1i (450 mg, 1.45 mmol, 1 eq.) in THF/water (10 ml/5 ml) and the reaction was stirred overnight at room temperature. Few drops of a 1N aqueous solution of HCl was added until acidic pH and the mixture was concentrated to dryness. The solid was taken up in DMF (15 ml) and piperazine 1j (373.4 mg, 1.595 mmol, 1.1 eq.), HATU (625 mg, 1.595 mmol, 1.1 eq.) and DIPEA (0.8 ml, 4.35 mmol, 3 eq.) were successively added. The resulting yellow mixture was stirred overnight at room temperature. DMF was removed in vacuo, the resulting mixture was taken up in EtOAc and brine. The aqueous layer was extracted with EtOAc, the organic layers were washed successively with brine and water, dried over Na$_2$SO$_4$, filtered and concentrated to dryness to afford a mixture of compounds. After purification by two automated silica gel chromatographies (1% to 5% MeOH in DCM, then 10% to 50% AcOEt in heptanes), compound 1 was isolated as a white solid (120 mg, 16% yield over 2 steps with a purity of 97% by HPLC). $^1$HNMR: (300 MHz, CHLOROFORM, d) 8.20-8.37 (m, 1H), 7.31-7.70 (m, 5H), 7.02 (d, 1H,) 4.11-4.21 (m, 1H), 3.40-3.98 (m, 7H), 2.37-2.78 (m, 5H), 0.75-0.92 (m, 4H).

Synthesis of Compound 2

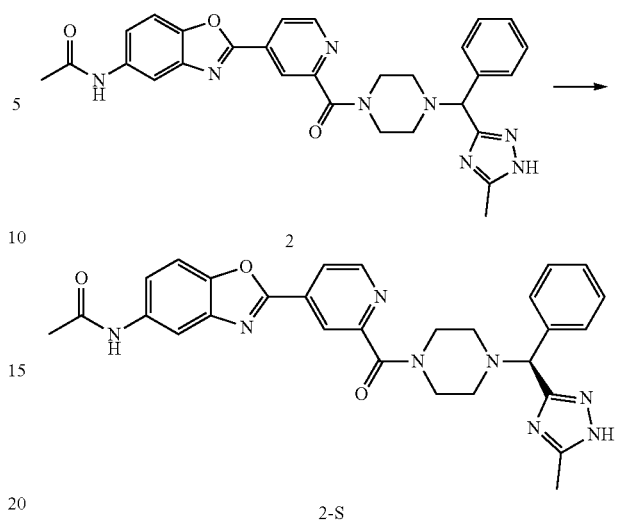

A separation of 2 was performed via Prep SFC (Stationary phase: Chiralpak Diacel AD 20×250 mm, Mobile phase: CO2, iPrOH+0.4 iPrNH$_2$). Compound 2-S (51 mg) was obtained as a white solid. LCMS: RT: 1.35, M+H=537.

Synthesis of Compound 3

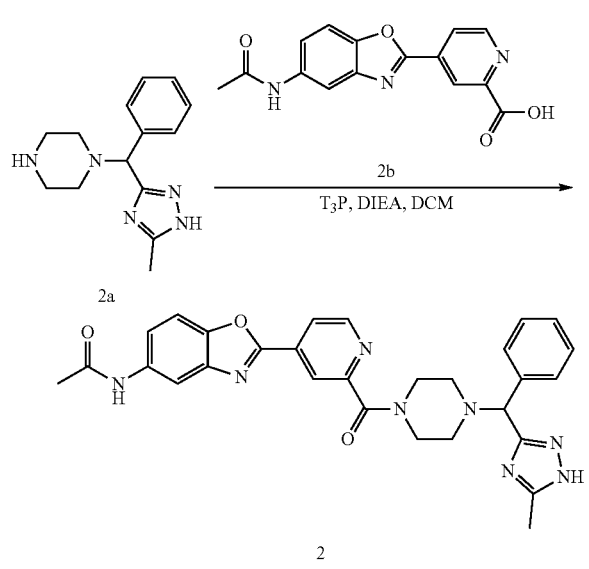

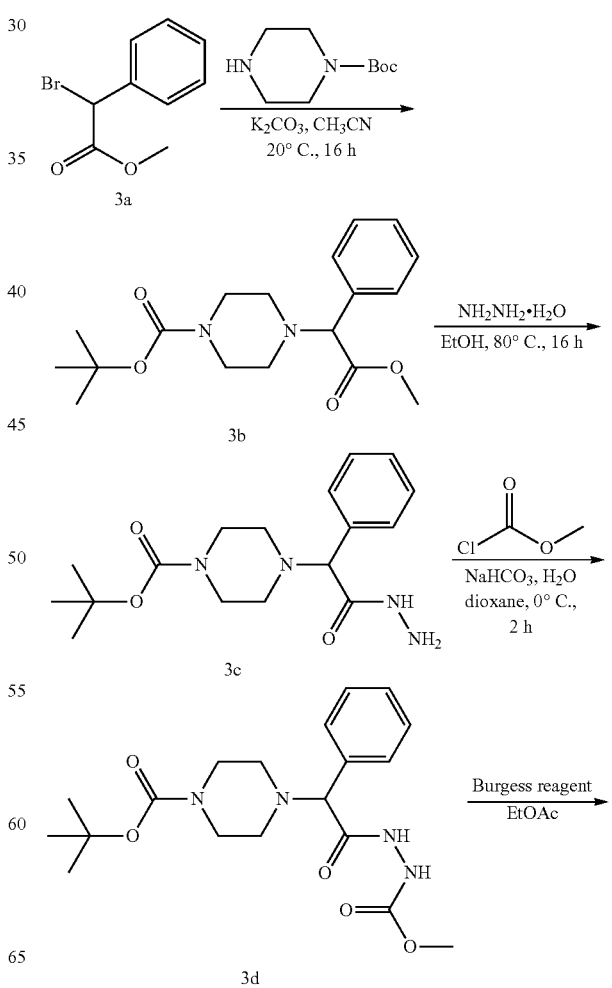

A solution of compound 2a (0.22 g, 0.59 mmol) in DCM (10.00 mL) was added compound 2b (0.25 g, 0.84 mmol), 2,4,6-Tripropyl-1,3,5,2,4,6-trioxatriphosphorinane-2,4,6-trioxide (0.64 g, 1.01 mmol, 50% purity) and DIEA (0.65 g, 5.03 mmol). The solution was stirred at 50° C. for 4 hrs. The reaction mixture was diluted with DCM, washed with water (20 mL×2), and concentrated in vacuo. The crude product was purified by prep HPLC (NH$_3$ as an additive). The compound 2 was lyophilized to give (142.8 mg, 0.27 mmol, 24.0% yield) was obtained as a white solid. LCMS: RT: 2.662, Area %: 92.221, MH+: 537.2; 1HNMR: (400 MHz, CHLOROFORM-d) 8.71 (d, J=5.02 Hz, 1H) 8.25 (s, 1H) 7.97-8.06 (m, 2H) 7.94 (s, 1H) 7.43-7.53 (m, 4H) 7.28-7.38 (m, 3H) 4.68 (s, 1H) 3.88 (br. s., 1H) 3.61 (br. s., 1H) 2.47-2.70 (m, 4H) 2.42 (s, 4H) 2.20 (s, 1H).

-continued

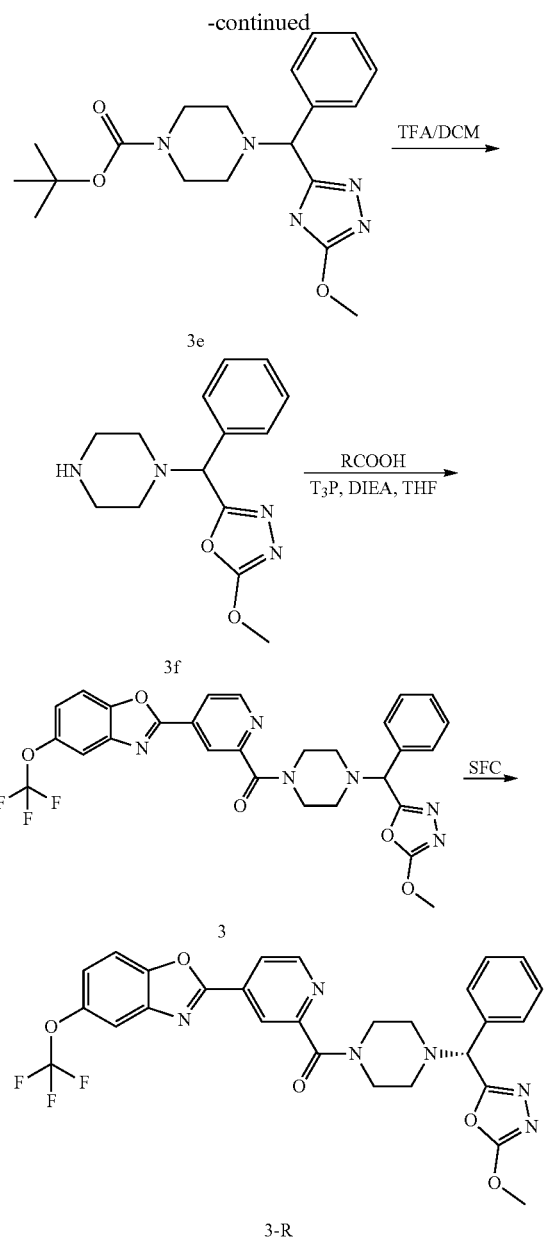

To a solution of methyl 2-bromo-2-phenyl-acetate 3a (20.00 g, 87.31 mmol, 13.70 mL, 1.00 eq) and tert-butyl piperazine-1-carboxylate (16.26 g, 87.31 mmol, 1.00 eq) in DMF (200.00 mL) was added K$_2$CO$_3$ (14.48 g, 104.77 mmol, 1.20 eq). The mixture was stirred at 16° C. for 16 h. TLC (PE:EtOAc=10:1) showed methyl 2-bromo-2-phenyl-acetate disappeared and a new spot (Rf=0.3) was detected. The reaction mixture was poured into H$_2$O (400 mL) and extracted with EtOAc (3×200 mL). The combined organic layers were washed with brine (200 mL), dried over Na$_2$SO$_4$, filtered and concentrated to give a residue. The residue was purified by silica column (PE:EtOAc=50:1 to 20:1) to give desired product as colorless oil. tert-butyl 4-(2-methoxy-2-oxo-1-phenyl-ethyl)piperazine-1-carboxylate 3b (28.00 g, 83.73 mmol, 95.90% yield) was obtained as colorless oil. $^1$HNMR: (CDCl$_3$ 400 MHz) 7.44-7.38 (m, 2H), 7.38-7.29 (m, 3H), 4.02 (s, 1H), 3.69 (s, 3H), 3.44 (t, J=4.8 Hz, 4H), 2.40 (br. s., 4H), 1.43 (s, 9H).

The mixture of tert-butyl 4-(2-methoxy-2-oxo-1-phenyl-ethyl)piperazine-1-carboxylate 3b (28.00 g, 83.73 mmol, 1.00 eq) and NH$_2$NH$_2$.H$_2$O (24.66 g, 418.65 mmol, 23.94 mL, 5.00 eq) was stirred 80° C. for 16 h. LCMS showed no start material remained and the desired product Ms was detected. The mixture was concentrated to give the desired product 3c as white solid. Crude tert-butyl 4-(2-hydrazino-2-oxo-1-phenyl-ethyl)piperazine-1-carboxylate (28.00 g, crude) was used in next step directly. $^1$HNMR: (CD$_3$OD, 400 MHz) 7.47 (dd, J=1.6, 7.8 Hz, 2H), 7.38-7.27 (m, 3H), 3.78 (s, 1H), 3.44 (br. s., 4H), 2.35 (td, J=5.1, 9.8 Hz, 4H), 1.44 (s, 9H).

To a solution of tert-butyl 4-(2-hydrazino-2-oxo-1-phenyl-ethyl)piperazine-1-carboxylate 3c (12.00 g, 35.88 mmol, 1.00 eq) in dioxane (50.00 mL) and water (50.00 mL) was added Na$_2$CO$_3$ (19.02 g, 179.42 mmol, 5.00 eq) and then methyl carbonochloridate (27.13 g, 287.07 mmol, 22.24 mL, 8.00 eq) dropwise at 0° C. The mixture was stirred at 0° C. for 3 h. LCMS (EW4102-17-P1A) showed the start material disappeared and the desired product Ms was detected. The mixture was extracted with EtOAc (200 mL×3). The organic layer was washed with brine (300 mL), dried over Na$_2$SO$_4$, filtered and concentrated to give the desired product as white solid, tert-butyl 4-[2-(2-methoxycarbonylhydrazino)-2-oxo-1-phenyl-ethyl]piperazine-1-carboxylate 3d (14.00 g, 35.67 mmol, 99% yield). $^1$HNMR: (CD$_3$OD 400 MHz) 7.50-7.45 (m, 2H), 7.38-7.30 (m, 3H), 3.88 (s, 1H), 3.66 (s, 3H), 3.45 (br. s, 4H), 2.57-2.49 (m, 2H), 2.41-2.31 (m, 2H), 1.44 (s, 9H).

To a solution of tert-butyl 4-[2-(2-methoxycarbonylhydrazino)-2-oxo-1-phenyl-ethyl]piperazine-1-carboxylate 3d (14.00 g, 35.67 mmol, 1.00 eq) in EtOAc (100.00 mL) was added Burgess Reagent (34.01 g, 142.69 mmol, 4.00 eq). The mixture was stirred at 100° C. for 16 h. TLC (PE:EtOAc=1:1) showed that a trace the starting material remained and the desired product spot (Rf=0.43) was detected. The mixture was concentrated to give a residue. The residue was purified by silica column (PE:EtOAc=10:1 to 6:1) to give the desired product as yellow oil. tert-butyl 4-[(5-methoxy-1,3,4-oxadiazol-2-yl)-phenyl-methyl]piperazine-1-carboxylate 3e (6.00 g, 14.26 mmol, 40% yield, 89% purity). $^1$HNMR: (CD$_3$OD 400 MHz) 7.47 (d, J=6.8 Hz, 2H), 7.42-7.33 (m, 3H), 4.75 (s, 1H), 4.15 (s, 3H), 3.43 (br. s, 4H), 2.51-2.34 (m, 4H), 1.44 (s, 9H).

To a solution of tert-butyl 4-[(5-methoxy-1,3,4-oxadiazol-2-yl)-phenyl-methyl]piperazine-1-carboxylate 3e (6.00 g, 16.02 mmol, 1.00 eq) in DCM (20.00 mL) was added TFA (12.32 g, 108.05 mmol, 8.00 mL, 6.74 eq). The mixture was stirred at 16° C. for 2 h. LCMS showed the starting material disappeared and the desired product Ms was detected. The mixture was concentrated. The residue was dissolved in DCM (10 mL) and basified by sat.NaHCO$_3$ solution to pH ~9. The mixture was extracted with DCM (10 mL×3). The DCM layer was washed with brine (15 mL), dried over Na$_2$SO$_4$, filtered and concentrated to give the desired product as yellow oil, which was used in next step directly. 2-methoxy-5-[phenyl(piperazin-1-yl)methyl]-1,3,4-oxadiazole 3f (1.20 g, 4.33 mmol, 27.03% yield, 99% purity). $^1$HNMR: (CD$_3$OD 400 MHz) 7.47 (d, J=1.4 Hz, 2H), 7.43-7.40 (m, 3H), 4.70 (s, 1H), 3.37 (s, 3H), 3.24-3.21 (m, 4H), 2.82-2.69 (m, 4H).

To a solution of 2-methoxy-5-[phenyl(piperazin-1-yl)methyl]-1,3,4-oxadiazole 3f (1.01 g, 3.70 mmol, 1.20 eq), 4-[5-(trifluoromethoxy)-1,3-benzoxazol-2-yl]pyridine-2-carboxylic acid (1.00 g, 3.08 mmol, 1.00 eq) in THF (20.00 mL) was added DIEA (796.12 mg, 6.16 mmol, 1.08 mL, 2.00 eq) and T$_3$P (3.92 g, 6.16 mmol, 3.66 mL, 50% purity, 2.00 eq). The mixture was stirred at 20° C. for 16 h. LCMS showed the two reactants were disappeared and the desired product was detected. The reaction mixture was quenched with water (20 mL) and extracted with EtOAc (20 mL×3). The combined organic layers were washed with brine (20 mL), dried over Na$_2$SO$_4$, filtered and concentrated under reduced pressure to give a residue. The residue was purified by silica column (PE:EtOAc=3:1 to 1:1) to give the desired 3 product as yellow solid. [4-[(5-methoxy-1,3,4-oxadiazol-2-yl)-phenyl-methyl]piperazin-1-yl]-[4-[5-(trifluoromethoxy)-1,3-benzoxazol-2-yl]-2-pyridyl]methanone (1.00 g, 1.69 mmol, 55% yield, 98% purity).

[4-[(5-methoxy-1,3,4-oxadiazol-2-yl)-phenyl-methyl] piperazin-1-yl]-[4-[5-(trifluoromethoxy)-1,3-benzoxazol-2-yl]-2-pyridyl]methanone (1.00 g, 1.72 mmol, 1.00 eq) was separated by SFC (AD-3S_3_5_40_3ML Column: Chiralpak AD-3 100×4.6 mm I.D., 3 um Mobile phase: methanol (0.05% DEA) in CO2 from 5% to 40% Flow rate: 3 mL/min Wavelength: 220 nm) to give the two desired products. Peak one with shorter runtime in SFC was [4-[(R)-(5-methoxy-1,3,4-oxadiazol-2-yl)-phenyl-methyl]piperazin-1-yl]-[4-[5-(trifluoromethoxy)-1,3-benzoxazol-2-yl]-2-pyridyl]methanone 3-R (337.57 mg, 564.06 umol, 33% yield, 97% purity) as white solid. Peak two with longer runtime in SFC was [4-[(S)-(5-methoxy-1,3,4-oxadiazol-2-yl)-phenyl-methyl] piperazin-1-yl]-[4-[5-(trifluoromethoxy)-1,3-benzoxazol-2-yl]-2-pyridyl]methanone (373.32 mg, 617.36 umol, 36% yield, 96% purity) as light yellow solid. The SFC method was from the small run. HPLC was the spectrum of the mixture aimed to SFC separation. $^1$HNMR: (CDCl$_3$ 400 MHz) 2.44-2.73 (m, 4H) 3.40 (s, 3H) 3.69 (t, J=4.77 Hz, 2H) 3.90 (t, J=4.96 Hz, 2H) 4.44 (s, 1H) 7.31-7.42 (m, 4H) 7.44-7.51 (m, 2H) 7.65 (d, J=8.91 Hz, 1H) 7.72 (d, J=1.00 Hz, 1H) 8.13 (dd, J=5.02, 1.63 Hz, 1H) 8.44 (s, 1H) 8.77 (d, J=5.14 Hz, 1H).

Synthesis of Compound 6

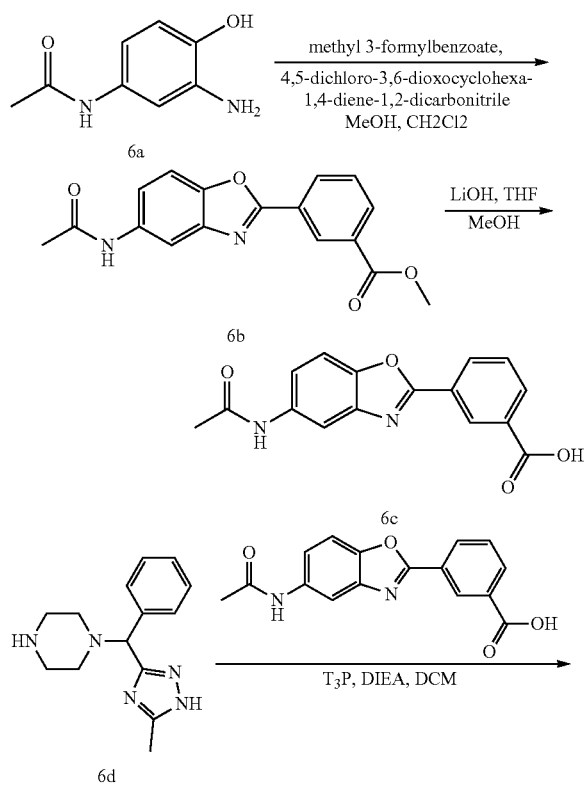

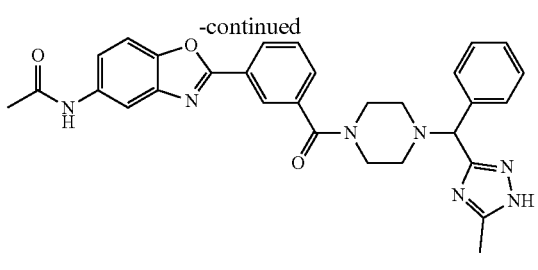

To a solution of compound 6a (2.00 g, 12.04 mmol) in MeOH (20 mL) was added methyl 3-formylbenzoate (2.00 g, 12.18 mmol) then stirred at 60° C. for 2 hrs. The mixture was then concentrated in vacuo. The mixture was dissolved in DCM (20 mL) followed by addition of DDQ (4.00 g, 17.62 mmol) and the mixture was stirred at 30° C. for 16 hrs. A precipitate was filtered off and the mixture was concentrated in vacuo. The brown oil was purified by column chromatography (silica gel, petroleum ether/EtOAc=10:1 to 1:1. UV) to give compound 6b (3.00 g, 9.67 mmol) confirmed by LCMS as a brown solid. LCMS: RT: 0.689, M+H: 311.1.

A mixture of compound 6b (200 mg, 0.65 mmol, 1.00 eq) and 4M aqueous LiOH (1.00 mL, 4.00 mmol) in MeOH (2.00 mL) and H$_2$O (2.00 mL) was stirred at 30° C. for 2.0 hours. The mixture was acidified with 4N aqueous HCl to pH 2-3. The mixture was concentrated in vacuo and the residue was purified by prep-HPLC to give compound 6c (110.0 mg, 0.37 mmol) as a brown solid. LCMS: RT: 0.621, M+H: 297.0.

A solution of compound 6c (100.0 mg, 0.301 mmol) in DCM (10 mL) was added compound 6d (150 mg, 0.404 mmol), T$_3$P (250 mg, 0.393 mmol, 50% purity) and DIEA (230 mg, 1.78 mmol). The solution was stirred at 50° C. for 0.5 hrs. The mixture was cooled to room temperature and diluted with DCM (30 mL). The reaction mixture was washed with water (20 mL×2), concentrated. The organic layer was dried over Na$_2$SO$_4$, filtered and concentrated in vacuo. The crude material was purified via prep-HPLC to give compound 6 (19.0 mg, 0.035 mmol) as a brown solid. $^1$HNMR: (400 MHz, CHLOROFORM-d) 2.19 (s, 3H) 2.40 (s, 3H) 2.44-2.69 (m, 4H) 3.48 (br. s., 2H) 3.69-3.96 (m, 2H) 4.68 (s, 1H) 7.31 (s, 2H) 7.43-7.55 (m, 6H) 7.86 (s, 1H) 8.03 (s, 1H) 8.16 (s, 1H) 8.19 (br. s., 1H); LCMS: RT: 2.800, M+H: 536.2.

Synthesis of Compound 133

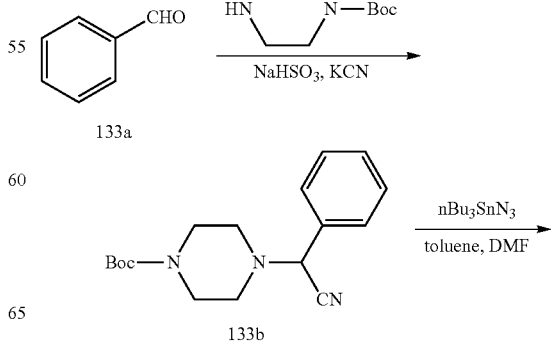

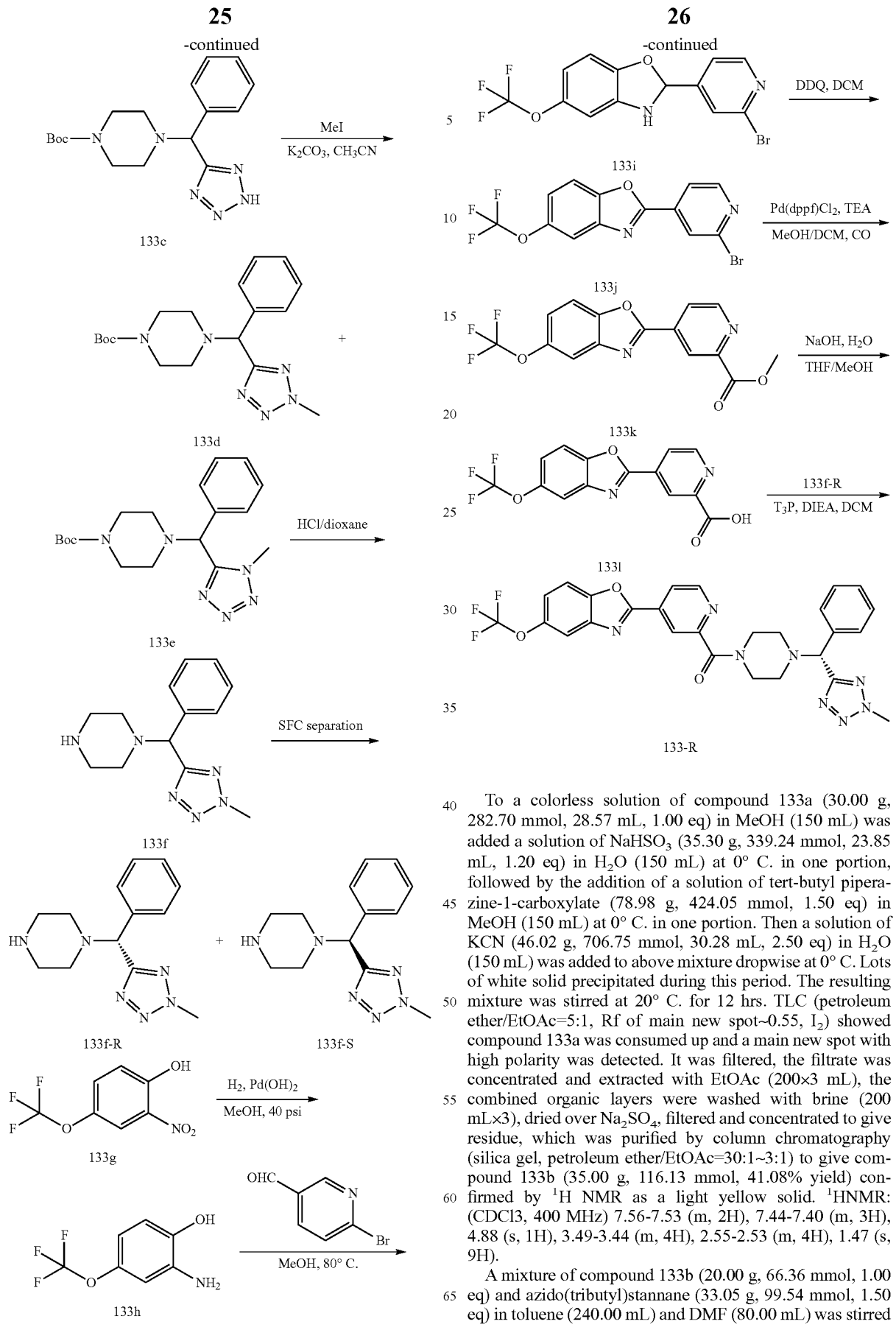

To a colorless solution of compound 133a (30.00 g, 282.70 mmol, 28.57 mL, 1.00 eq) in MeOH (150 mL) was added a solution of NaHSO$_3$ (35.30 g, 339.24 mmol, 23.85 mL, 1.20 eq) in H$_2$O (150 mL) at 0° C. in one portion, followed by the addition of a solution of tert-butyl piperazine-1-carboxylate (78.98 g, 424.05 mmol, 1.50 eq) in MeOH (150 mL) at 0° C. in one portion. Then a solution of KCN (46.02 g, 706.75 mmol, 30.28 mL, 2.50 eq) in H$_2$O (150 mL) was added to above mixture dropwise at 0° C. Lots of white solid precipitated during this period. The resulting mixture was stirred at 20° C. for 12 hrs. TLC (petroleum ether/EtOAc=5:1, Rf of main new spot~0.55, I$_2$) showed compound 133a was consumed up and a main new spot with high polarity was detected. It was filtered, the filtrate was concentrated and extracted with EtOAc (200×3 mL), the combined organic layers were washed with brine (200 mL×3), dried over Na$_2$SO$_4$, filtered and concentrated to give residue, which was purified by column chromatography (silica gel, petroleum ether/EtOAc=30:1~3:1) to give compound 133b (35.00 g, 116.13 mmol, 41.08% yield) confirmed by $^1$H NMR as a light yellow solid. $^1$HNMR: (CDCl3, 400 MHz) 7.56-7.53 (m, 2H), 7.44-7.40 (m, 3H), 4.88 (s, 1H), 3.49-3.44 (m, 4H), 2.55-2.53 (m, 4H), 1.47 (s, 9H).

A mixture of compound 133b (20.00 g, 66.36 mmol, 1.00 eq) and azido(tributyl)stannane (33.05 g, 99.54 mmol, 1.50 eq) in toluene (240.00 mL) and DMF (80.00 mL) was stirred at 120° C. for 36 hours. TLC (petroleum ether/EtOAc=1:1, Rf~0.25, I$_2$) showed compound 133b was consumed up and a main new spot with high polarity was detected. The mixture was washed with saturated aq. K$_2$CO$_3$ (200 mL×3) and the combined aqueous phases were acidified with 4.0 M aq.HCl to pH~4.0 and then extracted with EtOAc (200 mL×3). The combined organic layers were dried over Na$_2$SO$_4$, filtered and concentrated to give crude compound 133c (21.00 g, 60.97 mmol, 91.88% yield) as light yellow gum, which was used in next step without further purification.

A mixture of compound 133c (21.00 g, 60.97 mmol, 1.00 eq), CH$_3$I (17.31 g, 121.94 mmol, 7.59 mL, 2.00 eq) and K$_2$CO$_3$ (25.28 g, 182.91 mmol, 3.00 eq) in CH$_3$CN (200.00 mL) was stirred at 25° C. for 12 hrs. LC-MS showed compound 133c was consumed up and desired product was detected. TLC (petroleum ether/EtOAc=2:1, Rf of main new spot~0.6&0.54, I$_2$) showed compound 133c was consumed up and a main new spot with light polarity was detected. It was filtered via celite pad and the filtrate was concentrated to give residue, which was purified by column chromatography (silica gel, petroleum ether/EtOAc=10:1~1:1) to give the crude product. And it was further purified by prep. HPLC (Column: Phenomenex Gemini C18 250×50 mm×10 um; mobile phase: [water (0.05% ammonia hydroxide v/v)-ACN]; B %: 40%-65%,32,38% min) to give two isomers. H NMR and NOE showed peak 1 (retention time=1.400 in LC-MS) was compound 133e (6.00 g, 16.74 mmol, 27.45% yield) as a white solid. H NMR and NOE showed peak 2 (retention time=1.463 in LC-MS) was compound 133d (3.10 g, 8.65 mmol, 14.18% yield) as light yellow gum. $^1$HNMR: (DMSO-d6, 400 MHz) 7.47-7.45 (m, 2H), 7.36-7.28 (m, 3H), 5.01 (s, 1H), 4.34 (s, 3H), 3.29 (s, 4H), 2.37-2.35 (m, 2H), 2.24-2.21 (m, 2H), 1.35 (s, 9H).

A mixture of compound 133d (2.60 g, 7.25 mmol, 1.00 eq) and HCl/dioxane (4 M, 208.74 mL, 115.11 eq) in dioxane (10.00 mL) was stirred at 20° C. for 24 hours. TLC (petroleum ether/EtOAc=2:1, Rf of compound 133d~0.6, I$_2$) showed compound 133d was consumed up and a main new spot with high polarity was detected. It was concentrated to give residue, which was dissolved in H$_2$O (40 mL) and washed with CH$_2$Cl$_2$ (20 mL×2) and EtOAc (20 mL×2). The afforded aqueous phase was basified to pH~10 with saturated aq. Na$_2$CO$_3$ and extracted with EtOAc (50 mL×6). The combined organic layers were dried over Na$_2$SO$_4$, filtered and concentrated to give compound 133f (1.70 g, 6.52 mmol, 89.96% yield, 99.104% purity) confirmed by LC-MS as light yellow gum. LCMS: Column C18 2.1×50 mm, 5 um; Rf=0.985; M+H=259.

Compound 133f (2.00 g, 7.74 mmol, 1.00 eq) was separated by prep. SFC (column: AD(250 mm×30 mm, 10 um); mobile phase: [Base-MeOH];B %: %-%, 3.5 minutes, 300 minutes, workup: concentrated) to give the two corresponding isomers. Compound 133f-R (650.00 mg, 2.49 mmol, 32.12% yield, 98.8% purity) confirmed by LC-MS and SFC was obtained as light yellow gum.

To a solution of compound 133g (6.0 g, 26.89 mmol, 1.00 eq)) in MeOH (80.00 mL) was added Pd(OH)$_2$/C (500.00 mg, 50.00 mmol, 10% purity, 1.86 eq) under N$_2$. The suspension was degassed under vacuum and purged with H$_2$ several times. The mixture was stirred under H$_2$ (40 psi) at 16° C. for 16 hours. TLC (Petroleum ether/Ethyl acetate=10:1) showed the starting material was consumed completely and a new spot (Rf=0.4) was detected. The reaction mixture was filtered and the filter was concentrated to give compound 133h (5.18 g, 26.69 mmol, 99.25% yield, 99.5% purity) as brown solid, which was used in next step directly. $^1$HNMR: (CD$_3$OD, 400 MHz) 6.66 (d, J=8.5 Hz, 1H), 6.62-6.59 (m, 1H), 6.40 (ddd, J=0.8, 2.7, 8.6 Hz, 1H).

The mixture of compound 133h (5.18 g, 26.82 mmol, 1.00 eq) and 6-bromopyridine-3-carbaldehyde (4.99 g, 26.82 mmol, 1.00 eq) in MeOH (100.00 mL) was stirred at 80° C. for 16 h. TLC (PE:EtOAc=5:1) showed trace starting material remained and a new spot (Rf=0.6) was formed. The mixture was concentrated to give the desired product (9.68 g, crude) as red oil, which was used in next step directly.

To a solution of compound 133i (9.68 g, 26.81 mmol, 1.00 eq) in DCM (150.00 mL) was added DDQ (7.30 g, 32.17 mmol, 1.20 eq). The mixture was stirred at 16° C. for 1 h. TLC (PE:EtOAc=10:1) showed the starting material disappeared and a new spot (Rf=0.7) was detected. The mixture was quenched with Na$_2$CO$_3$ solution (400 mL) and extracted with DCM (100 mL×3). The DCM layer was washed with brine (200 mL), dried over Na$_2$SO$_4$, filtered and concentrated. The residue was purified by silica column (PE:EtOAc=30:1) to give compound 133j (6.50 g, 18.10 mmol, 67.52% yield) as orange oil. $^1$HNMR: (400 MHz, CDCl$_3$) 8.59 (dd, J=0.6, 5.1 Hz, 1H), 8.29 (dd, J=0.7, 1.3 Hz, 1H), 8.04 (dd, J=1.4, 5.1 Hz, 1H), 7.71 (d, J=1.0 Hz, 1H), 7.64 (d, J=8.8 Hz, 1H), 7.34 (tdd, J=0.7, 1.6, 8.9 Hz, 1H).

To a solution of compound 133j (9.00 g, 25.06 mmol, 1.00 eq) in MeOH (10.00 mL) and DCM (10.00 mL) was added TEA (10.14 g, 100.25 mmol, 13.90 mL, 4.00 eq) and Pd(dppf)Cl$_2$ (3.67 g, 5.01 mmol, 0.20 eq) in autoclave. The mixture was stirred at 120° C. for 16 h in CO atmosphere (2 MPa). TLC (PE:EtOAc=2:1) showed the starting material disappeared and a new spot (Rf=0.2) was detected. After filtrated, the filtrate was concentrated. The residue was purified by silica column (PE:EtOAc=5:1 to 2:1) to give compound 133k (6.00 g, 14.55 mmol, 58.04% yield, 82% purity) as an orange solid.

To a mixed solution of compound 133k (6.00 g, 17.74 mmol, 1.00 eq) in THF (50.00 mL), MeOH (50.00 mL) and Water (50.00 mL) was added NaOH (3.55 g, 88.70 mmol, 5.00 eq). The mixture was stirred at 16° C. for 2 h. TLC (PE:EtOAc=1:1) showed the starting material disappeared and a new spot with larger polarity was formed. The mixture was concentrated. The residue was acidified by 1N HCl to pH~3 and then extracted with EtOAc (50 mL×3). The EtOAc layer was washed with brine (30 mL), dried over Na$_2$SO$_4$, filtered and concentrated to give compound 133l (4.20 g, 12.95 mmol, 73.02% yield) as a white solid, which was used in next step directly. $^1$HNMR: (400 MHz, CD$_3$OD) 8.93 (d, J=5.0 Hz, 1H), 8.89 (s, 1H), 8.39 (d, J=5.0 Hz, 1H), 7.87 (d, J=8.9 Hz, 1H), 7.80 (s, 1H), 7.47 (d, J=8.9 Hz, 1H).

A mixture of compound 133f-R (300.00 mg, 1.16 mmol, 1.00 eq), compound 133l (414.17 mg, 1.28 mmol, 1.10 eq), EDCI (333.95 mg, 1.74 mmol, 1.50 eq), HOBt (235.38 mg, 1.74 mmol, 1.50 eq) and DIPEA (225.14 mg, 1.74 mmol, 304.24 µL, 1.50 eq) in DMF (10.00 mL) was stirred at 15° C. for 12 hrs. LC-MS showed the main peak was the desired product. TLC (EtOAc=100%, Rf~0.53, UV) detected a man spot. This reaction was combined with EW4103-42 for final workup and purification. It was diluted with EtOAc (30 mL) and washed with brine (30 mL×3). The organic layer was dried over Na$_2$SO$_4$, filtered and concentrated to give residue, which was purified by column chromatography (silica gel, petroleum ether/EtOAc=8:1~0:1) to give 133-R (709.88 mg, 1.25 mmol, 107.79% yield, 99.434% purity). $^1$HNMR: (400 MHz, CDCl$_3$) 8.77-8.75 (m, 1H), 8.41 (s, 1H), 8.11-8.10 (m, 1H), 7.71 (s, 1H), 7.64 (d, J=8.8 Hz, 1H), 7.53 (d, J=7.2 Hz, 1H), 7.37-7.35 (m, 2H), 7.33-7.30 (m, 4H), 5.00 (s, 1H), 4.35 (s, 3H), 3.92-3.86 (m, 2H); 3.67 (s, 2H), 2.69-2.66 (m, 1H), 2.61-2.56 (m, 2H), 2.43-2.42 (m,1H).

Synthesis of Compound 134

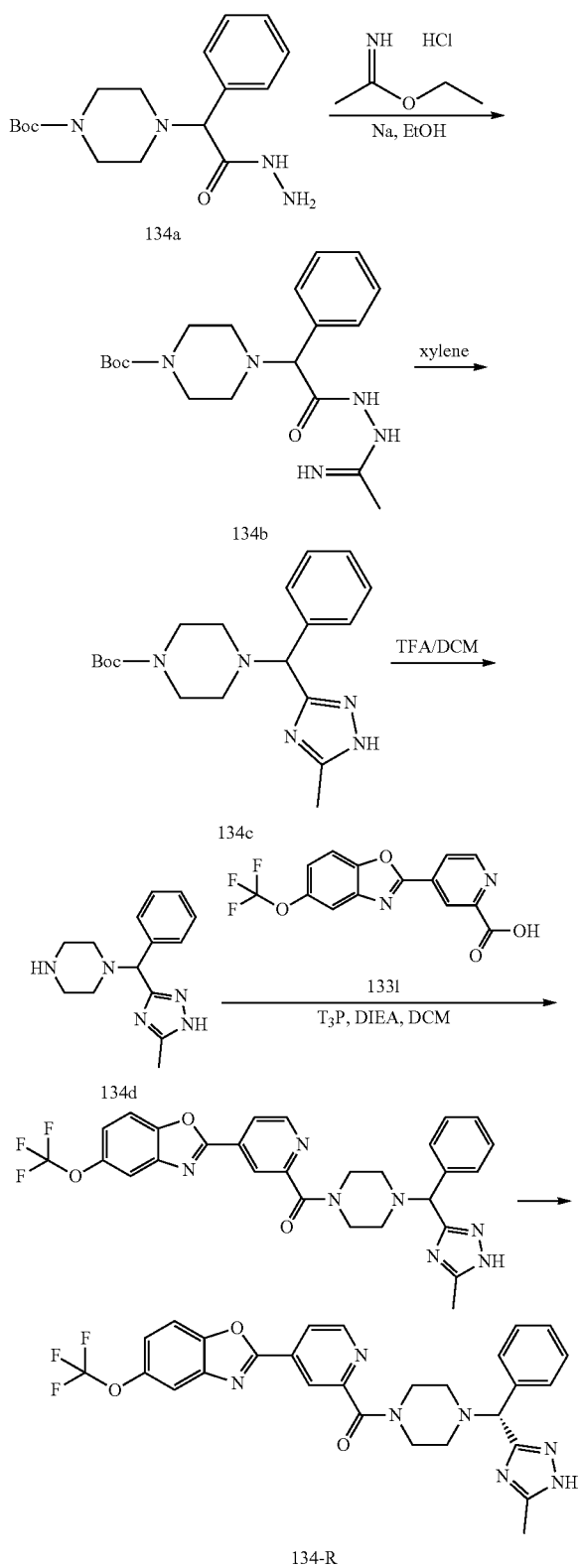

To a solution of Na (516.58 mg, 22.47 mmol, 532.56 μL, 1.80 eq) in EtOH (100.00 mL) was added compound CH$_3$C(NH)(OEt).HCl (2.78 g, 22.47 mmol, 1.80 eq, HCl). The solution was stirred at 25° C. for 1 hr, then the reaction mixture was filtered and the filtrate was added compound 134a (4.17 g, 12.48 mmol, 1.00 eq). The reaction was stirred at 25° C. for 3 hrs. TLC (PE:EA=2:1) showed compound 134a (R$_f$=0.01) was consumed and a new spot with light polarity formed (R$_f$=0.4). LCMS showed desired product was detected (R$_t$=0.619, purity=70.303%). The reaction mixture was concentrated. The crude product was used directly in next step. Compound 134b (5.00 g, crude) was obtained as a light pink solid. $^1$HNMR: (DMSO-d$_6$, 400 MHz) 9.11-8.73 (m, 2H), 7.50-7.37 (m, 2H), 7.36-7.21 (m, 3H), 3.43-3.36 (m, 6H), 2.40-2.22 (m, 4H), 2.10 (s, 2H), 1.37 (s, 9H).

A solution of compound 134b (5.00 g, 13.32 mmol, 1.00 eq) in O-XYLENE (80.00 mL) was stirred at 120° C. for 12 hrs. TLC (PE:EA=1:1) showed compound 134b was consumed and three new spots formed. LCMS showed desired product was detected (R$_t$=0.674, purity=87.913%). The reaction mixture was concentrated. The desired product was isolated by silica column (PE:EA=8:1-1:1). Compound 134c (2.00 g, 5.60 mmol, 42.01% yield) was obtained as light yellow solid.) $^1$H NMR: (DMSO-d$_6$, 400 MHz) 7.55-7.39 (m, 2H), 7.38-7.17 (m, 3H), 3.33-3.24 (m, 3H), 2.53-2.46 (m, 8H), 2.30 (s, 1H), 1.46-1.27 (m, 9H).

A solution of compound 134c (4.00 g, 11.19 mmol, 1.00 eq) in DCM (24.00 mL) was added TFA (12.32 g, 108.05 mmol, 8.00 mL, 9.66 eq). The solution was stirred at 16° C. for 5 hrs. TLC (DCM:MeOH=10:1) showed compound 134c was consumed (R$_f$=0.4) and a new spot with large polarity formed (R$_f$=0.1). LCMS showed desired product was detected (R$_t$=1.233, purity=79.089%). The reaction mixture was concentrated, diluted with H$_2$O (50 mL), washed with EtOAc (50 mL×3), basified by saturated Na$_2$CO$_3$ to pH=11, extracted with DCM and propan-2-ol (volume ratio=3:1, 200 mL×5), concentrated. The crude product was used directly in next step. Compound 134d (2.00 g, 7.77 mmol, 69.46% yield) was obtained as a light yellow solid.

A solution of compound 134d (1.27 g, 4.95 mmol, 1.10 eq) in DCM (10.00 mL) was added compound 133l (1.46 g, 4.50 mmol, 1.00 eq), T$_3$P (5.73 g, 9.00 mmol, 5.35 mL, 50% purity, 2.00 eq) and DIEA (1.16 g, 9.00 mmol, 1.57 mL, 2.00 eq). The solution was stirred at 16° C. for 5 hrs. TLC (DCM:MeOH=10:1) showed most of compound 133l was consumed (R$_f$=0.01) and two new spot with light polarity formed (R$_{f1}$=0.3, R$_{f2}$=0.35). LCMS showed desired product was detected (R$_t$=0.764, purity=80.962%). The reaction mixture was washed with brine (100 mL×3), concentrated. The crude product was purified by silica column (DCM:MeOH=1:0~30:1). Compound 134 (1.20 g, 2.13 mmol, 47.32% yield) was obtained as a yellow solid. HPLC showed the purity of product was 91.702%. (1.20 g, 2.13 mmol, 1.00 eq) was separated by prep. SFC prep-HPLC (column: AD (250 mm×50 mm, 10 μm); mobile phase: [Base-IPA]; B %: 50%-50%, 4.1 MIN; 250 min) to give the desired chiral purity enantiomer. was purified by prep TLC (DCM:MeOH:EA=10:1:11). Compound 134-R was obtained as a white solid. HPLC showed the purity was 99.286%. $^1$H NMR: (CDCl$_3$, 400 MHz) 11.63 (s, 1H), 8.74-8.73 (d, J=4 Hz, 1H), 8.38 (s, 1H), 8.09-8.08 (dd, J=4, 4 Hz, 1H), 7.68 (s, 1H), 7.62-7.60 (d, J=8 Hz, 1H), 7.48-7.47 (d, J=4 Hz, 2H), 7.35-7.27 (m, 3H), 7.24 (m, 1H), 4.68 (s, 1H), 4.00-3.76 (m, 2H), 3.74-3.53 (m, 2H), 2.68-2.50 (m, 3H), 2.48-2.34 (m, 4H).

Virus Binding and Neutralization Activity of Compounds of Formula (I)

Competition binding studies were designed to test compounds for competition with well characterized HA binding proteins with known epitopes on HA, such as CR9114, CR6261, or HB80.4. The epitopes were located at the stem of the HA (viral membrane proximal part of HA), or, for control purposes, at the head of HA (viral membrane distal part of HA). If a compound showed competition, it was interpreted to bind to a similar or at least overlapping epitope at the surface of HA. Competition with both HA head- and stem-binders was interpreted as unspecific binding.

Hereto an AlphaLISA (Perkin Elmer) competition assay was established which relied on full length and trimeric HA proteins (Protein Sciences) bound by HA-specific binders. The interaction between HA and the binding protein was detected after incubation at room temperature with two beads, a streptavidin donor bead recognizing biotinylated HA and an acceptor bead containing a recognition motif for the binding protein. Close proximity of the excited donor bead and acceptor bead was measured as a luminescence signal (Biotek Synergy Neo Plate Reader or Perkin Elmer EnVision plate reader). Compounds were tested for their ability to compete in a range from 1 nM to 50 μM and the resulting sigmoidal inhibition curves were fitted with a standard four parameter logistic nonlinear regression model in SPSS. Competition binding was tested for HA derived from multiple influenza strains in repeats to assess the breadth of binding. Averages of calculated pIC50 values are shown in Table 1.

Compounds were analysed in a virus neutralization assay (VNA) for their ability to prevent influenza virus infection of mammalian cells. For this purpose, Madin-Darby Canine Kidney Epithelial (MDCK) cells were seeded in 96-well flat bottom plates (25,000 cells/well). Compounds were serially diluted, centrifuged (1000 g for 15 min) to remove potential aggregates, inoculated with virus and incubated for 4-6 h at 37° C. under a 5% $CO_2$ atmosphere in complete Dulbecco's Modified Eagle's medium (DMEM), supplemented with 2 mM L-glutamine and 3 μg/mL trypsin-EDTA. The mixture (~1-5 TCID50/well) was then added to confluent MDCK monolayers. Cells were cultured for 96 h before cytopathic effect (CPE) was measured through an ATPlite (PerkinElmer) luminescence assay (Biotek Synergy Neo Plate Reader). The pEC50 of compounds was determined with SPSS software. Multiple influenza strains were tested in repeats to assess the breadth of neutralization. Averages of calculated pEC50 values are shown in Table 1.

TABLE 1

Competition binding (AlphaLISA - pIC50) and virus neutralization (VNA - pEC50) values of compounds of formula (I).

| | Competition binding (AlphaLISA), pIC50 | | | Virus neutralization assay (VNA), pEC50 | | | |
|---|---|---|---|---|---|---|---|
| | H1 A/California/ 07/09 | H1 A/New Caledonia/ 20/99 | H5 A/Vietnam/ 1203/04 | H1N1 A/California/ 07/09 | H1N1 A/New Caledonia/ 20/99 | H1N1 A/PR/ 8/34-MA | H5N1 A/Vietnam/ 1203/04 |
| 1 | 8.9 | 9.2 | 7.2 | 8.6 | 8.6 | | 6.7 |
| 2 | 8.1 | 8.3 | 6.8 | 8.0 | 8.6 | | 6.0 |
| 3 | 8.2 | 8.4 | 7.0 | 6.9 | 7.3 | | 5.2 |
| 4 | 7.9 | 8.1 | 7.0 | 7.0 | 7.1 | | 5.9 |
| 5 | 7.6 | 7.8 | 6.3 | 7.8 | 8.2 | | 5.9 |
| 6 | 7.7 | 8.0 | 6.3 | 7.7 | 8.2 | | 4.9 |
| 7 | 8.2 | 8.5 | 6.8 | 7.6 | 7.6 | | 5.8 |
| 8 | 8.2 | 8.4 | 6.7 | 7.4 | 7.5 | | 5.9 |
| 9 | 8.2 | 8.4 | 6.6 | 7.2 | 7.4 | | 5.8 |
| 10 | 7.6 | 7.8 | 6.1 | 7.1 | 7.3 | | 5.6 |
| 11 | 8.1 | 8.2 | 6.5 | 7.1 | 7.3 | | 5.9 |
| 12 | 8.2 | 8.1 | 6.8 | 7.4 | 7.4 | | 5.9 |
| 13 | 8.1 | 8.2 | 6.3 | 7.1 | 7.3 | | 5.5 |
| 14 | 7.7 | 8.0 | 6.9 | 6.9 | 7.2 | | 6.0 |
| 15 | 8.5 | 8.2 | 6.8 | 6.8 | 7.4 | | 5.1 |
| 16 | 7.8 | 7.8 | 6.4 | 7.1 | 7.1 | | 5.5 |
| 17 | 7.8 | 7.5 | 6.2 | 6.9 | 6.7 | | 5.4 |
| 18 | 7.4 | 7.7 | 6.4 | 6.7 | 7.1 | | 4.7 |
| 19 | 7.7 | 7.8 | 6.7 | 6.6 | 7.0 | 6.9 | 5.8 |
| 20 | 7.9 | 7.7 | 6.3 | 7.1 | 7.0 | | 5.1 |
| 21 | 7.8 | 7.7 | 6.1 | 7.0 | 7.1 | | 5.2 |
| 22 | 7.8 | 7.9 | 6.7 | 6.8 | 6.9 | 6.9 | 5.8 |
| 23 | 7.7 | 8.0 | 6.4 | 6.8 | 6.9 | | 4.7 |
| 24 | 7.2 | 7.4 | 5.5 | 6.8 | 6.9 | | 4.9 |
| 25 | 7.8 | 7.6 | 6.1 | 7.2 | 7.1 | | 5.4 |
| 26 | 7.6 | 7.7 | 6.3 | 6.8 | 6.8 | | 5.1 |
| 27 | 7.5 | 7.3 | 5.9 | 6.5 | 6.5 | | 4.4 |
| 28 | 7.8 | 7.7 | 6.3 | 6.7 | 6.8 | | 5.4 |
| 29 | 7.6 | 7.8 | 6.6 | 6.6 | 6.8 | 6.9 | 5.4 |
| 30 | 7.6 | 7.6 | 6.2 | 6.6 | 6.8 | | 5.1 |
| 31 | 7.5 | 7.6 | 5.9 | 6.5 | 6.8 | | 5.1 |
| 32 | 7.2 | 7.1 | 5.4 | 6.5 | 6.8 | | 4.6 |
| 33 | 7.3 | 7.5 | 6.4 | 6.3 | 6.8 | | 5.1 |
| 34 | 7.5 | 7.2 | 5.9 | 6.9 | 6.6 | | 4.9 |
| 35 | 7.8 | 7.8 | 6.2 | 6.7 | 6.8 | | 5.2 |
| 36 | 7.6 | 7.6 | 6.0 | 6.8 | 6.9 | | 5.1 |
| 37 | 7.2 | 7.3 | 5.8 | 6.6 | 6.6 | | 4.5 |
| 38 | 7.3 | 7.3 | 5.7 | 6.5 | 6.7 | | 5.1 |
| 39 | 7.6 | 7.5 | 5.8 | 6.5 | 6.7 | | 5.0 |
| 40 | 7.5 | 7.3 | 5.9 | 6.8 | 6.6 | | 5.0 |
| 41 | 7.8 | 7.5 | 6.2 | 6.9 | 6.7 | | 5.4 |
| 42 | 7.4 | 7.4 | 6.0 | 6.5 | 6.6 | | 4.8 |
| 43 | 7.5 | 7.6 | 5.9 | 6.4 | 6.6 | | 5.0 |

TABLE 1-continued

Competition binding (AlphaLISA - pIC50) and virus neutralization (VNA - pEC50) values of compounds of formula (I).

| | Competition binding (AlphaLISA), pIC50 | | | Virus neutralization assay (VNA), pEC50 | | | |
|---|---|---|---|---|---|---|---|
| | H1 A/California/ 07/09 | H1 A/New Caledonia/ 20/99 | H5 A/Vietnam/ 1203/04 | H1N1 A/California/ 07/09 | H1N1 A/New Caledonia/ 20/99 | H1N1 A/PR/ 8/34-MA | H5N1 A/Vietnam/ 1203/04 |
| 44 | 7.3 | 7.3 | 5.8 | 6.4 | 6.5 | | 4.9 |
| 45 | 7.2 | 7.0 | 5.1 | 6.6 | 6.5 | | 4.3 |
| 46 | 7.5 | 7.5 | 6.1 | 6.7 | 6.8 | | 4.8 |
| 47 | 7.1 | 7.1 | 5.0 | 6.4 | 6.5 | | 4.8 |
| 48 | 6.6 | 6.7 | 4.9 | 6.2 | 6.5 | | <4.3 |
| 49 | 6.6 | 6.7 | 5.4 | 6.3 | 6.5 | | 4.5 |
| 50 | 7.2 | 7.2 | 5.4 | 6.1 | 6.5 | | 4.5 |
| 51 | 7.8 | 7.9 | 6.2 | 6.6 | 6.6 | | 4.8 |
| 52 | 6.7 | 6.7 | 4.7 | 6.2 | 6.4 | | <4.3 |
| 53 | 5.3 | 5.4 | 4.7 | 6.0 | 6.4 | | <4.3 |
| 54 | 7.0 | 7.3 | 6.4 | 5.9 | 6.4 | | 5.2 |
| 55 | 7.2 | 7.3 | 6.2 | 5.7 | 6.4 | | 5.0 |
| 56 | 6.4 | 6.8 | 5.5 | 5.3 | 6.4 | | <4.3 |
| 57 | 7.3 | 7.1 | 5.6 | 6.6 | 6.3 | | 4.7 |
| 58 | 7.4 | 7.5 | 6.0 | 6.4 | 6.4 | | 5.3 |
| 59 | 7.2 | 7.2 | 5.7 | 6.4 | 6.3 | | 4.7 |
| 60 | 7.2 | 7.4 | 5.8 | 6.2 | 6.3 | | 4.9 |
| 61 | 7.1 | 7.2 | 6.3 | 6.2 | 6.3 | | 5.7 |
| 62 | 7.0 | 7.0 | 5.5 | 6.2 | 6.2 | | 4.7 |
| 63 | 6.8 | 6.8 | 4.8 | 6.2 | 6.3 | | <4.3 |
| 64 | 7.1 | 7.1 | 5.7 | 6.0 | 6.3 | | 4.6 |
| 65 | 7.0 | 7.3 | 6.2 | 6.0 | 6.3 | 6.2 | 4.6 |
| 66 | 7.0 | 7.2 | 6.1 | 6.0 | 6.3 | | 4.9 |
| 67 | 7.3 | 7.3 | 5.5 | 6.1 | 6.2 | | 4.5 |
| 68 | 6.7 | 7.0 | 5.9 | 5.7 | 6.3 | | 4.7 |
| 69 | 7.2 | 7.1 | 5.6 | 6.4 | 6.2 | | 4.5 |
| 70 | 6.8 | 6.8 | 5.4 | 6.3 | 6.2 | | <4.3 |
| 71 | 7.0 | 7.0 | 6.0 | 6.1 | 6.2 | | 5.1 |
| 72 | 6.7 | 6.9 | 5.8 | 6.1 | 6.2 | | 4.4 |
| 73 | 7.8 | 7.6 | 5.9 | 6.1 | 6.1 | | <4.3 |
| 74 | 6.7 | 7.1 | 5.7 | 6.0 | 6.2 | | 5.2 |
| 75 | 6.7 | 6.8 | 5.4 | 6.0 | 6.2 | | 5.1 |
| 76 | 6.7 | 6.8 | 5.0 | 5.9 | 6.2 | | 4.5 |
| 77 | 6.6 | 6.7 | 5.0 | 5.9 | 6.2 | | <4.3 |
| 78 | 6.2 | 6.5 | 4.6 | 5.9 | 6.2 | | 4.3 |
| 79 | 6.7 | 7.1 | 5.9 | 5.8 | 6.2 | | 4.9 |
| 80 | 6.5 | 6.6 | 6.0 | 5.8 | 6.2 | | <4.3 |
| 81 | 6.7 | 6.9 | 5.9 | 5.7 | 6.2 | | 5.0 |
| 82 | 6.7 | 6.9 | 6.0 | 5.7 | 6.2 | | 4.9 |
| 83 | 6.4 | 6.7 | 5.6 | 5.7 | 6.2 | 6.0 | 4.8 |
| 84 | 6.5 | 6.7 | 5.8 | 5.6 | 6.2 | | 4.5 |
| 85 | 6.2 | 6.5 | 5.5 | 5.6 | 6.2 | 6.3 | 4.9 |
| 86 | 7.1 | 6.9 | 5.5 | 6.2 | 6.1 | | 4.5 |
| 87 | 7.2 | 7.4 | 5.6 | 6.4 | 6.3 | | 4.4 |
| 88 | 6.7 | 6.9 | 6.3 | 6.0 | 6.1 | | 4.9 |
| 89 | 7.1 | 7.1 | 5.9 | 5.9 | 6.1 | | 4.8 |
| 90 | 6.5 | 6.8 | 6.0 | 5.8 | 6.1 | | <4.3 |
| 91 | 6.3 | 6.5 | 5.6 | 5.8 | 6.1 | | <4.3 |
| 92 | 6.9 | 7.1 | 5.5 | 5.5 | 6.1 | | 5.0 |
| 93 | 7.1 | 7.2 | 6.2 | 5.4 | 6.1 | | 5.1 |
| 94 | 7.1 | 7.3 | 6.2 | 6.5 | 6.0 | | 5.1 |
| 95 | 6.9 | 6.8 | 5.3 | 6.1 | 6.0 | | 4.5 |
| 96 | 6.7 | 6.5 | 4.8 | 6.1 | 6.0 | | 4.3 |
| 97 | 7.0 | 7.1 | 6.2 | 6.0 | 6.0 | | 5.4 |
| 98 | 6.6 | 6.9 | 5.6 | 5.9 | 6.0 | | 4.9 |
| 99 | 6.6 | 6.8 | 5.9 | 5.8 | 6.0 | | <4.3 |
| 100 | 6.3 | 6.5 | 4.6 | 5.7 | 6.0 | | 4.6 |
| 101 | 6.2 | 6.1 | 4.4 | 5.7 | 6.0 | | <4.3 |
| 102 | 6.7 | 6.6 | 4.9 | 5.7 | 6.0 | | <4.3 |
| 103 | 6.7 | 6.9 | 6.0 | 5.6 | 6.0 | | 4.8 |
| 104 | 6.6 | 6.7 | 5.7 | 5.6 | 6.0 | | 5.0 |
| 105 | 6.9 | 7.0 | 5.7 | 5.5 | 6.0 | 5.7 | 4.9 |
| 106 | 6.4 | 6.7 | 5.7 | 5.5 | 6.0 | | <4.3 |
| 107 | 6.4 | 6.6 | 4.7 | 5.5 | 6.0 | | <4.3 |
| 108 | 5.8 | 6.3 | 4.6 | 5.3 | 6.0 | | <4.3 |
| 109 | 7.1 | 6.8 | 5.4 | 6.3 | 5.9 | | 4.6 |
| 110 | 6.4 | 6.1 | 4.3 | 5.9 | 5.9 | | <4.3 |
| 111 | 6.5 | | 4.6 | 5.8 | 5.9 | | <4.3 |
| 112 | 6.3 | 6.4 | 5.2 | 5.8 | 5.9 | | <5.3 |
| 113 | 6.3 | 6.2 | 4.6 | 5.9 | 5.8 | | <4.3 |
| 114 | 7.0 | 6.9 | 6.4 | 5.7 | 5.9 | 5.6 | 4.5 |

TABLE 1-continued

Competition binding (AlphaLISA - pIC50) and virus neutralization
(VNA - pEC50) values of compounds of formula (I).

| | Competition binding (AlphaLISA), pIC50 | | | Virus neutralization assay (VNA), pEC50 | | | |
|---|---|---|---|---|---|---|---|
| | H1 A/California/ 07/09 | H1 A/New Caledonia/ 20/99 | H5 A/Vietnam/ 1203/04 | H1N1 A/California/ 07/09 | H1N1 A/New Caledonia/ 20/99 | H1N1 A/PR/ 8/34-MA | H5N1 A/Vietnam/ 1203/04 |
| 115 | 6.6 | 6.5 | 5.1 | 5.7 | 5.9 | | <4.3 |
| 116 | 6.3 | 6.4 | 5.3 | 5.8 | 5.8 | | <4.3 |
| 117 | 6.9 | 7.0 | 5.2 | 5.6 | 5.9 | | 4.5 |
| 118 | 6.6 | 6.5 | 4.6 | 5.1 | 5.9 | | 4.5 |
| 119 | 6.8 | 6.8 | 5.7 | 6.0 | 5.8 | | 4.6 |
| 120 | 6.6 | 6.6 | 5.6 | 5.9 | 5.8 | 6.0 | <4.3 |
| 121 | 6.7 | 6.9 | 5.8 | 5.5 | 5.8 | | 4.4 |
| 122 | 6.4 | 6.7 | 5.6 | 5.4 | 5.8 | | 4.9 |
| 123 | 6.2 | 6.3 | 4.9 | 5.3 | 5.8 | 5.6 | 4.3 |
| 124 | 7.2 | 7.1 | 6.2 | 6.3 | 5.7 | | 5.4 |
| 125 | 6.8 | 6.8 | 4.9 | 5.8 | 5.7 | | 4.3 |
| 126 | 5.8 | 5.8 | 4.8 | 5.8 | 5.7 | | <4.3 |
| 127 | 7.1 | 6.6 | 5.1 | 5.6 | 5.7 | | 4.7 |
| 128 | 6.6 | 6.8 | 5.5 | 5.5 | 5.7 | | 5.0 |
| 129 | 6.2 | 6.3 | 4.5 | 5.4 | 5.7 | | <4.3 |
| 130 | 6.0 | 6.2 | 5.0 | 4.8 | 5.7 | 4.9 | 4.4 |
| 131 | 5.5 | 5.4 | 4.4 | 5.8 | 5.6 | | <4.3 |
| 132 | 6.1 | 6.2 | 4.8 | 4.4 | 5.6 | | <4.3 |
| 133 | 7.8 | 8.0 | 6.6 | 7.2 | 7.6 | | 6.2 |
| 134 | 7.4 | 7.8 | 6.8 | 6.2 | 6.6 | | 5.4 |

Cytotoxic Activity of Compounds of Formula (I)

To determine the level of cytotoxicity the VNA was also performed in the absence of virus. Cytopathic effect (CPE) was measured through an ATPlite (PerkinElmer) luminescence assay (Biotek Synergy Neo Plate Reader). The pCC50 of compounds was calculated with SPSS software. Averages of calculated pCC50 values are shown in Table 2.

TABLE 2

Molecular structure of preferred compounds of formula (I) with cytotoxicity levels (pCC50).

| Example | Structure | Cytotoxicity (pCC50) MDCK |
|---|---|---|
| 1 | 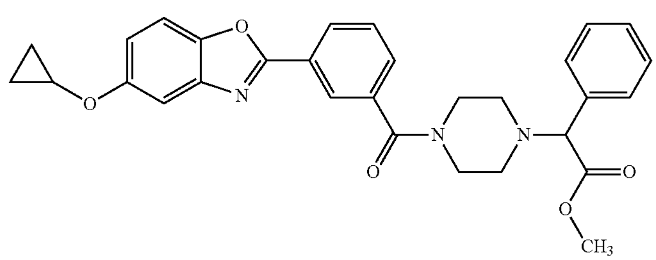 | <4.3 |
| 2 | 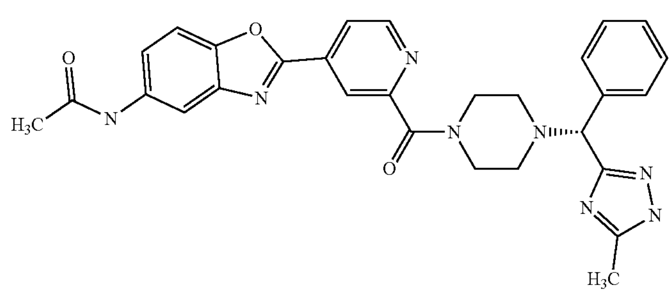 [SMILES: CC(=O)Nc1ccc2oc(-c3ccnc(C(=O)N4CCN([C@H](c5ccccc5)c5n[nH]c(C)n5)CC4)c3)nc2c1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 3 | 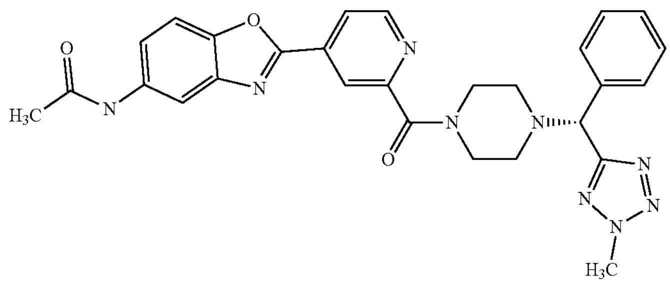 [SMILES: CC(=O)Nc1ccc2oc(-c3ccnc(C(=O)N4CCN([C@H](c5ccccc5)c5nnn(C)n5)CC4)c3)nc2c1] | <4.3 |
| 4 | 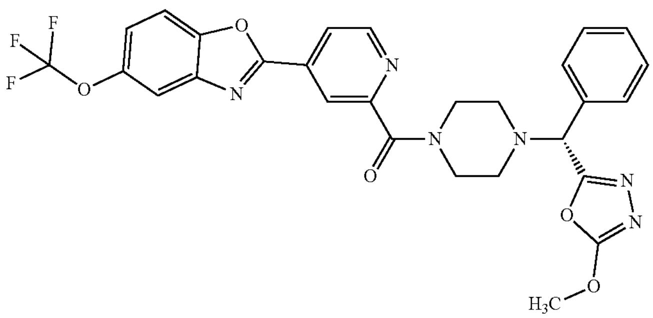 [SMILES: COc1nnc([C@@H](c2ccccc2)N2CCN(C(=O)c3cc(-c4nc5cc(OC(F)(F)F)ccc5o4)ccn3)CC2)o1] | <4.3 |
| 5 | 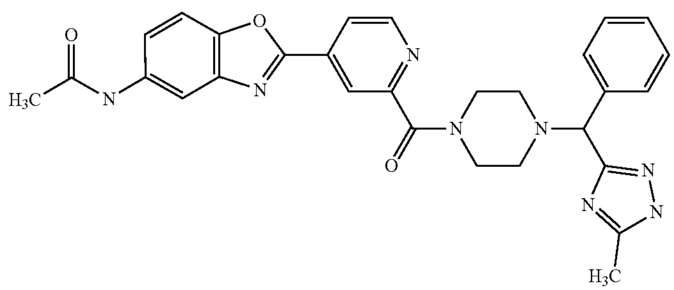 [SMILES: CC(=O)Nc1ccc2oc(-c3ccnc(C(=O)N4CCN(C(c5ccccc5)c5n[nH]c(C)n5)CC4)c3)nc2c1] | <4.3 |
| 6 | 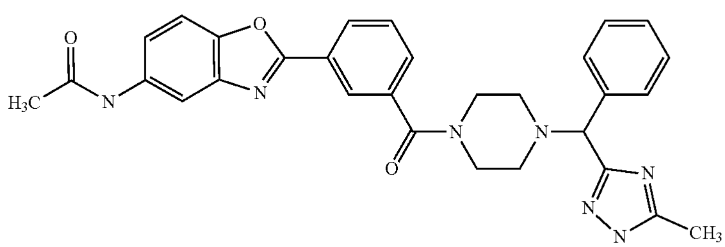 [SMILES: CC(=O)Nc1ccc2oc(-c3cccc(C(=O)N4CCN(C(c5ccccc5)c5n[nH]c(C)n5)CC4)c3)nc2c1] | <4.3 |
| 7 | 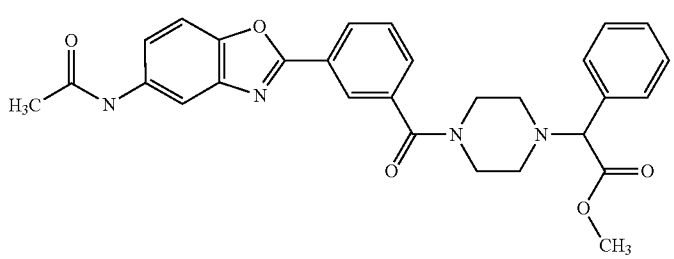 [SMILES: COC(=O)C(c1ccccc1)N1CCN(C(=O)c2cccc(-c3nc4cc(NC(C)=O)ccc4o3)c2)CC1] | 4.5 |

TABLE 2-continued

Molecular structure of preferred compounds of formula (I) with cytotoxicity levels (pCC50).

| Example | Structure | Cytotoxicity (pCC50) MDCK |
|---|---|---|
| 8 | 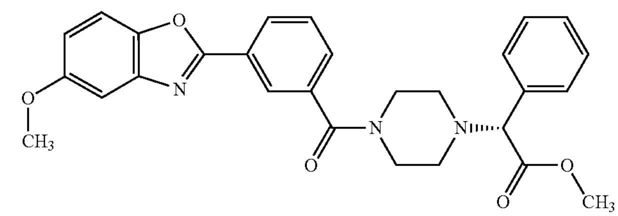 [SMILES: COC(=O)[C@@H](c1ccccc1)N1CCN(C(=O)c2cccc(-c3nc4cc(OC)ccc4o3)c2)CC1] | <4.3 |
| 9 [a] | 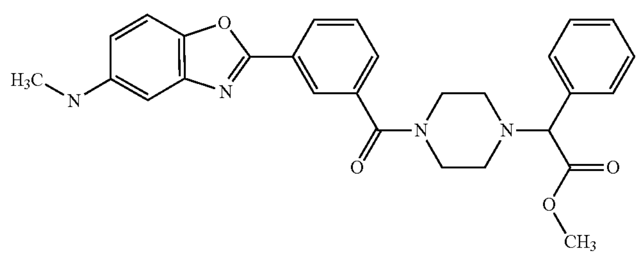 [SMILES: CNc1ccc2oc(-c3cccc(C(=O)N4CCN(C(C(=O)OC)c5ccccc5)CC4)c3)nc2c1] | 5.0 |
| 10 | 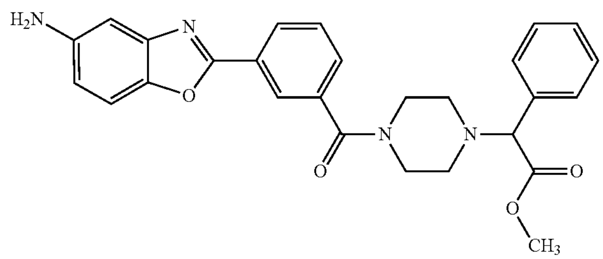 [SMILES: COC(=O)C(c1ccccc1)N1CCN(C(=O)c2cccc(-c3nc4cc(N)ccc4o3)c2)CC1] | 4.6 |
| 11 [a] | 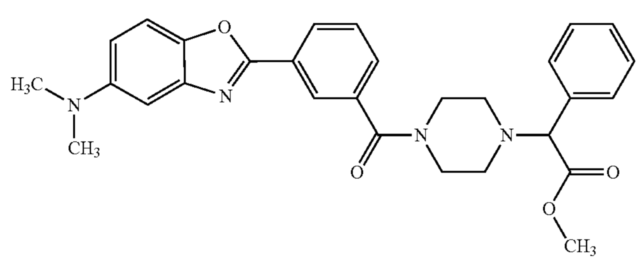 [SMILES: COC(=O)C(c1ccccc1)N1CCN(C(=O)c2cccc(-c3nc4cc(N(C)C)ccc4o3)c2)CC1] | 5.4 |
| 12 | 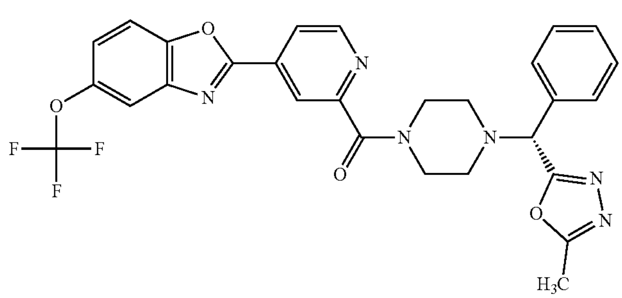 [SMILES: Cc1nnc([C@@H](c2ccccc2)N2CCN(C(=O)c3cc(-c4nc5cc(OC(F)(F)F)ccc5o4)ccn3)CC2)o1] | 4.8 |

TABLE 2-continued

Molecular structure of preferred compounds of formula (I) with cytotoxicity levels (pCC50).

| Example | Structure | Cytotoxicity (pCC50) MDCK |
|---|---|---|
| 13 | 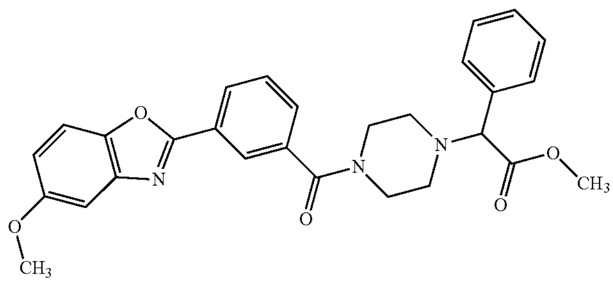 [SMILES: COC(=O)C(c1ccccc1)N1CCN(C(=O)c2cccc(-c3nc4cc(OC)ccc4o3)c2)CC1] | 4.3 |
| 14 | 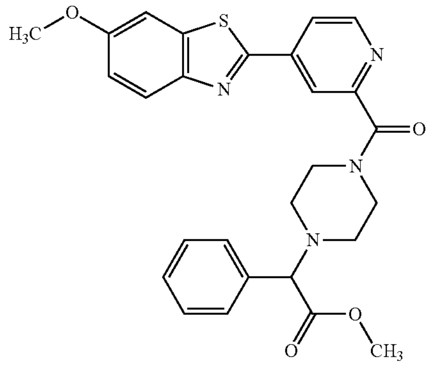 [SMILES: COC(=O)C(c1ccccc1)N1CCN(C(=O)c2cc(-c3nc4ccc(OC)cc4s3)ccn2)CC1] | 4.8 |
| 15 | 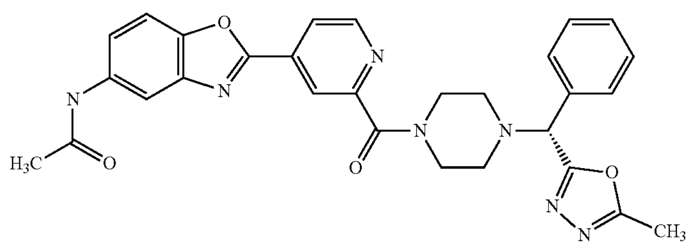 [SMILES: CC(=O)Nc1ccc2oc(-c3ccnc(C(=O)N4CCN([C@H](c5ccccc5)c5nnc(C)o5)CC4)c3)nc2c1] | <4.3 |
| 16 | 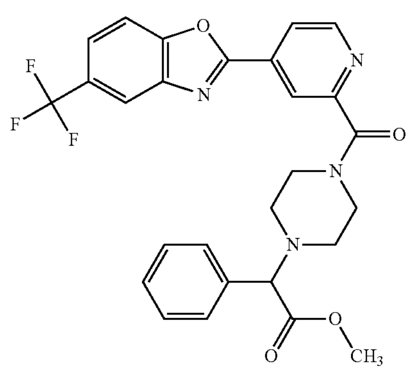 [SMILES: COC(=O)C(c1ccccc1)N1CCN(C(=O)c2cc(-c3nc4cc(C(F)(F)F)ccc4o3)ccn2)CC1] | |
| 17 | 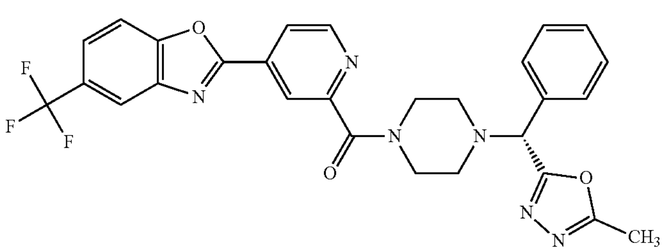 [SMILES: Cc1nnc([C@@H](c2ccccc2)N2CCN(C(=O)c3cc(-c4nc5cc(C(F)(F)F)ccc5o4)ccn3)CC2)o1] | 5.1 |

TABLE 2-continued

Molecular structure of preferred compounds of formula (I) with cytotoxicity levels (pCC50).

| Example | Structure | Cytotoxicity (pCC50) MDCK |
|---|---|---|
| 18 | 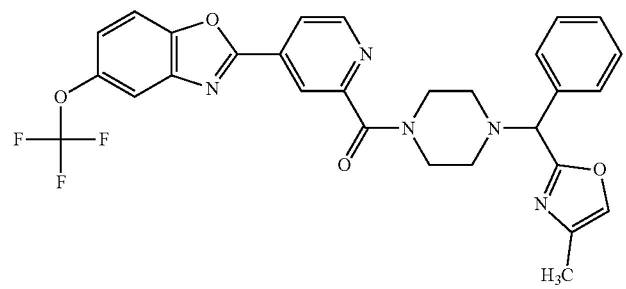 [SMILES: Cc1coc(C(c2ccccc2)N2CCN(C(=O)c3cc(-c4nc5cc(OC(F)(F)F)ccc5o4)ccn3)CC2)n1] | <4.3 |
| 19 | 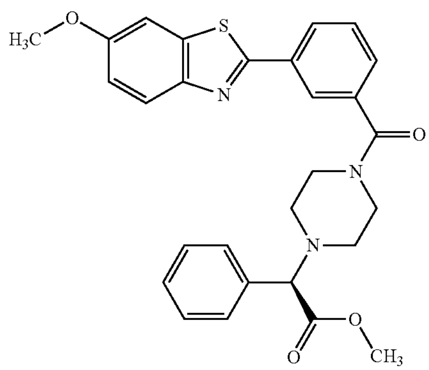 | <4.3 |
| 20 | 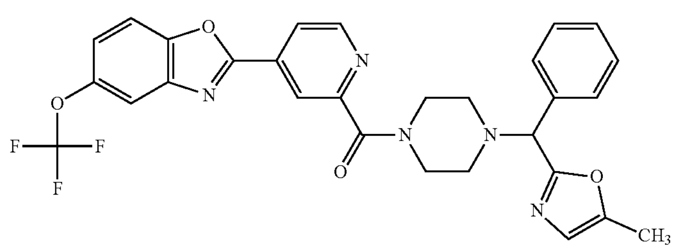 [SMILES: Cc1cnc(C(c2ccccc2)N2CCN(C(=O)c3cc(-c4nc5cc(OC(F)(F)F)ccc5o4)ccn3)CC2)o1] | 4.6 |
| 21 | 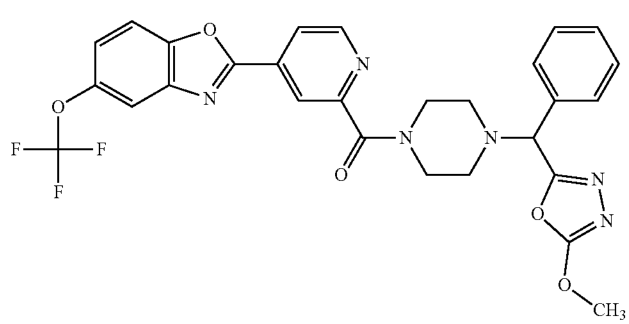 [SMILES: COc1nnc(C(c2ccccc2)N2CCN(C(=O)c3cc(-c4nc5cc(OC(F)(F)F)ccc5o4)ccn3)CC2)o1] | 4.9 |

TABLE 2-continued

Molecular structure of preferred compounds of formula (I) with cytotoxicity levels (pCC50).

| Example | Structure | Cytotoxicity (pCC50) MDCK |
|---|---|---|
| 22 | 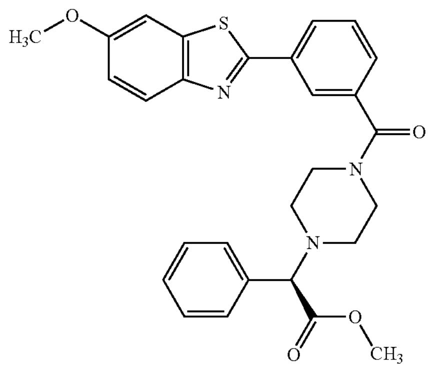 | <4.3 |
| 23 | 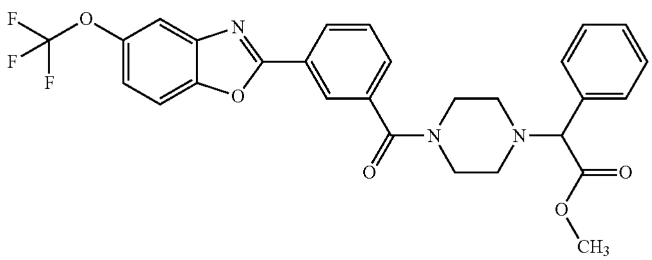 [SMILES: COC(=O)C(c1ccccc1)N1CCN(C(=O)c2cccc(-c3nc4cc(OC(F)(F)F)ccc4o3)c2)CC1] | <4.3 |
| 24 | 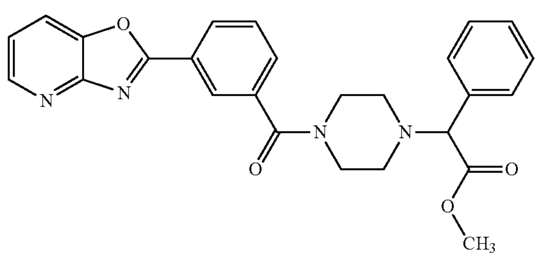 [SMILES: COC(=O)C(c1ccccc1)N1CCN(C(=O)c2cccc(-c3nc4ncccc4o3)c2)CC1] | <4.3 |
| 25 | 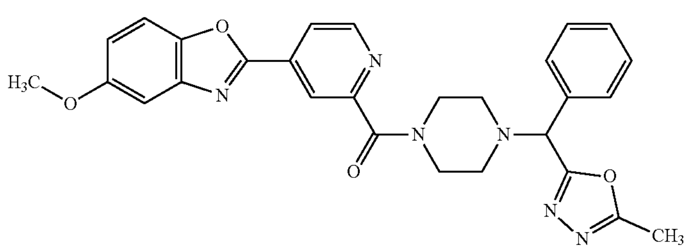 | 4.6 |
| 26 [a] | 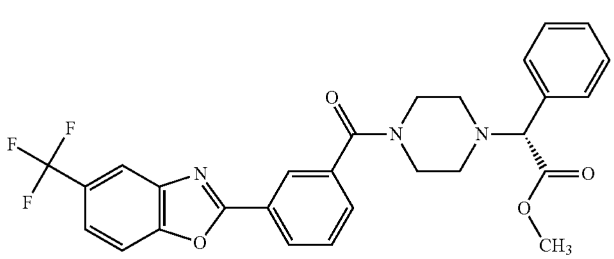 [SMILES: COC(=O)[C@@H](c1ccccc1)N1CCN(C(=O)c2cccc(-c3nc4cc(C(F)(F)F)ccc4o3)c2)CC1] | <4.3 |

TABLE 2-continued

Molecular structure of preferred compounds of formula (I) with cytotoxicity levels (pCC50).

| Example | Structure | Cytotoxicity (pCC50) MDCK |
|---------|-----------|---------------------------|
| 27 | 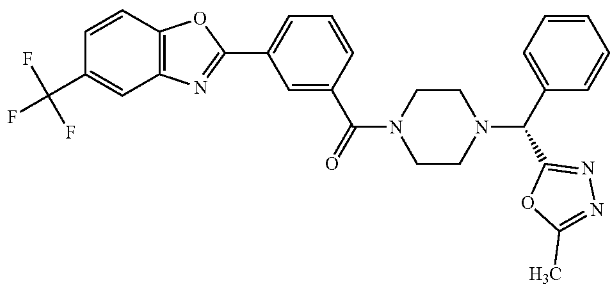 [SMILES: Cc1nnc([C@@H](c2ccccc2)N2CCN(C(=O)c3cccc(-c4nc5cc(C(F)(F)F)ccc5o4)c3)CC2)o1] | <4.3 |
| 28 | 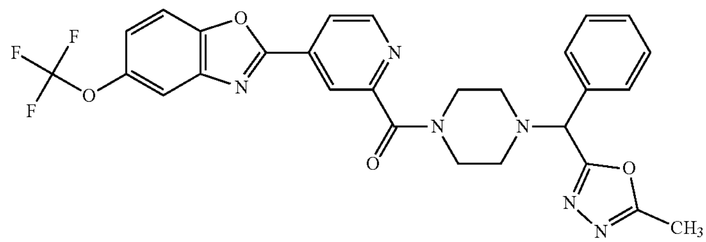 [SMILES: Cc1nnc(C(c2ccccc2)N2CCN(C(=O)c3cc(-c4nc5cc(OC(F)(F)F)ccc5o4)ccn3)CC2)o1] | 4.8 |
| 29 | 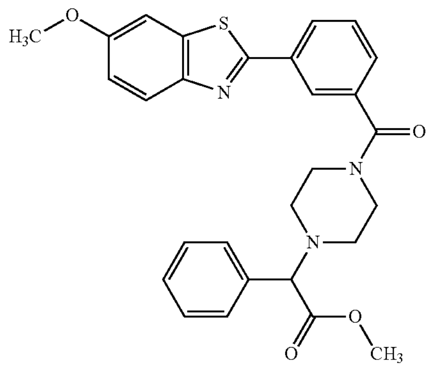 | 4.4 |
| 30 | 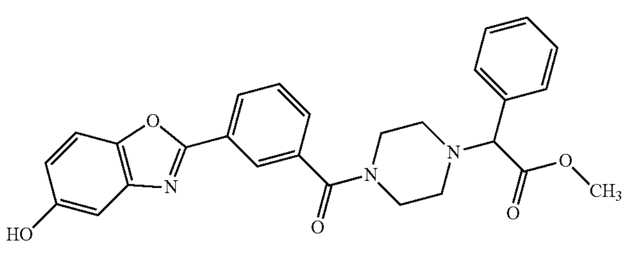 [SMILES: COC(=O)C(c1ccccc1)N1CCN(C(=O)c2cccc(-c3nc4cc(O)ccc4o3)c2)CC1] | 4.6 |
| 31 | 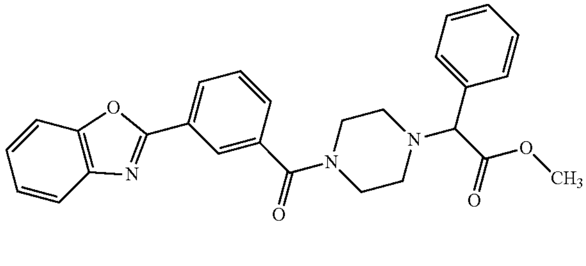 [SMILES: COC(=O)C(c1ccccc1)N1CCN(C(=O)c2cccc(-c3nc4ccccc4o3)c2)CC1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 32 | 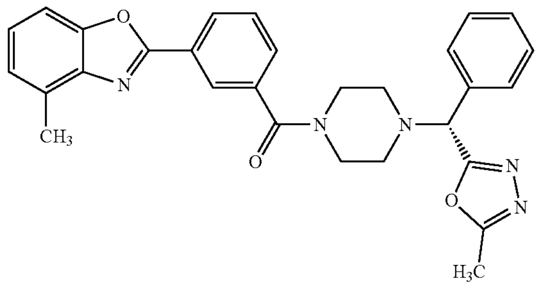 [SMILES: Cc1nnc([C@@H](c2ccccc2)N2CCN(C(=O)c3cccc(-c4nc5c(C)cccc5o4)c3)CC2)o1] | 4.8 |
| 33 [a] | 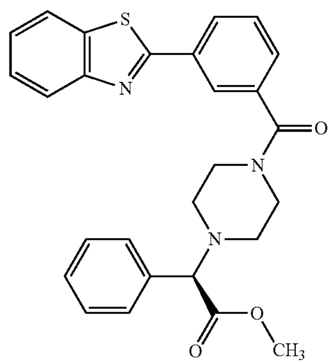 [SMILES: COC(=O)[C@@H](c1ccccc1)N1CCN(C(=O)c2cccc(-c3nc4ccccc4s3)c2)CC1] | 4.4 |
| 34 | 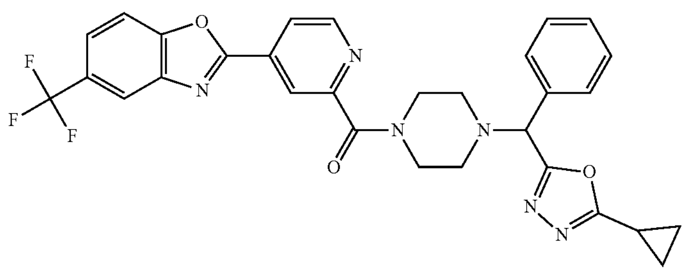 [SMILES: O=C(c1cc(-c2nc3cc(C(F)(F)F)ccc3o2)ccn1)N1CCN(C(c2ccccc2)c2nnc(C3CC3)o2)CC1] | 4.4 |
| 35 [b] | 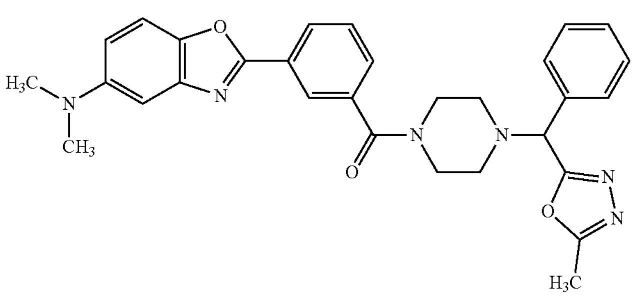 [SMILES: Cc1nnc(C(c2ccccc2)N2CCN(C(=O)c3cccc(-c4nc5cc(N(C)C)ccc5o4)c3)CC2)o1] | 4.6 |

TABLE 2-continued

Molecular structure of preferred compounds of formula (I) with cytotoxicity levels (pCC50).

| Example | Structure | Cytotoxicity (pCC50) MDCK |
|---|---|---|
| 36 | 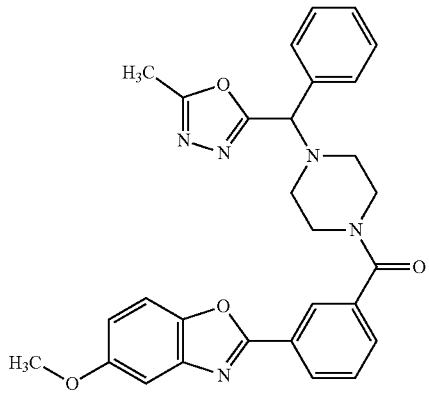 [SMILES: COc1ccc2oc(-c3cccc(C(=O)N4CCN(C(c5ccccc5)c5nnc(C)o5)CC4)c3)nc2c1] | 4.7 |
| 37 | 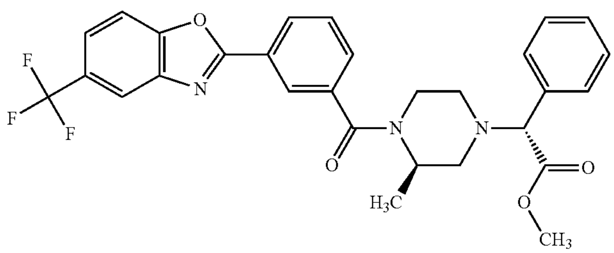 [SMILES: COC(=O)[C@@H](c1ccccc1)N1CCN(C(=O)c2cccc(-c3nc4cc(C(F)(F)F)ccc4o3)c2)[C@H](C)C1] | <4.3 |
| 38 | 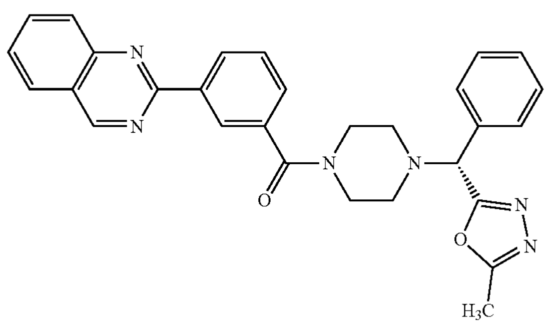 | <4.3 |
| 39 [b] | 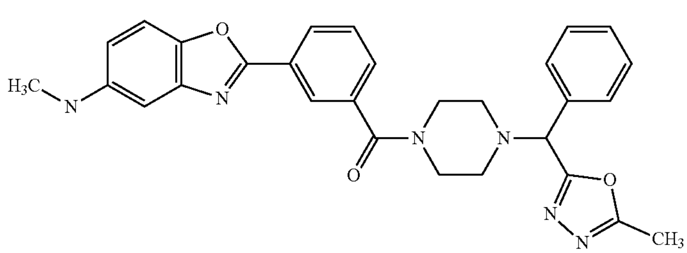 | 4.8 |
| 40 | 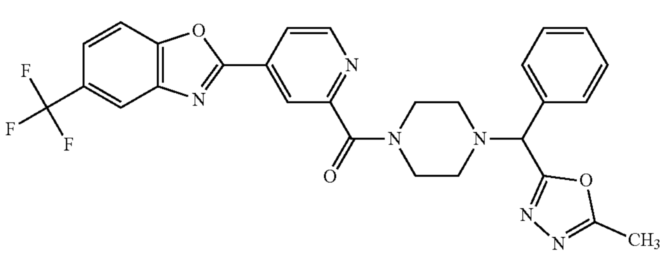 | 4.9 |

TABLE 2-continued

Molecular structure of preferred compounds of formula (I) with cytotoxicity levels (pCC50).

| Example | Structure | Cytotoxicity (pCC50) MDCK |
|---|---|---|
| 41 | 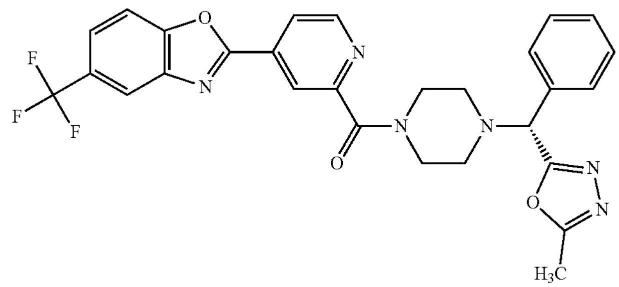 [SMILES: Cc1nnc([C@@H](c2ccccc2)N2CCN(C(=O)c3cc(-c4nc5cc(C(F)(F)F)ccc5o4)ccn3)CC2)o1] | 5.1 |
| 42 | 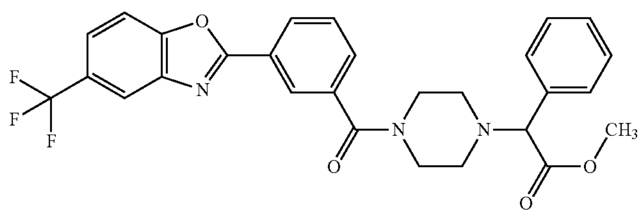 [SMILES: COC(=O)C(c1ccccc1)N1CCN(C(=O)c2cccc(-c3nc4cc(C(F)(F)F)ccc4o3)c2)CC1] | <4.3 |
| 43 | 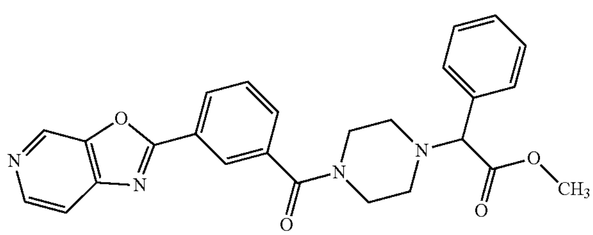 [SMILES: COC(=O)C(c1ccccc1)N1CCN(C(=O)c2cccc(-c3nc4ccncc4o3)c2)CC1] | <4.3 |
| 44 [b] | 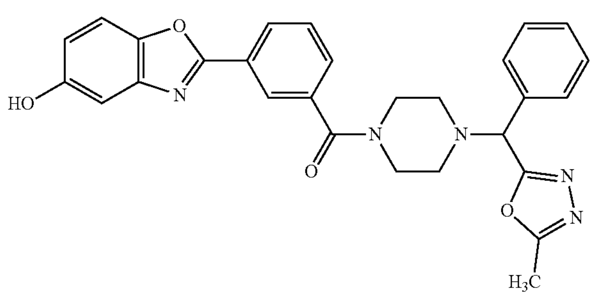 [SMILES: Cc1nnc(C(c2ccccc2)N2CCN(C(=O)c3cccc(-c4nc5cc(O)ccc5o4)c3)CC2)o1] | 4.4 |
| 45 | 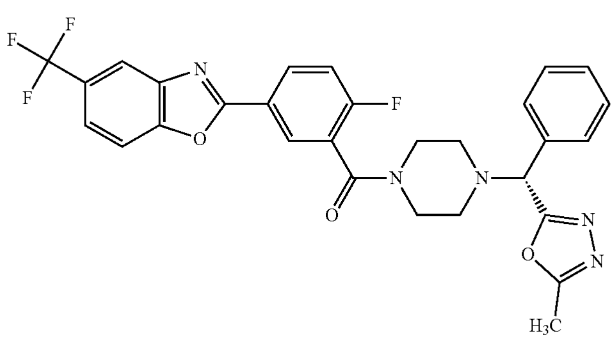 [SMILES: Cc1nnc([C@@H](c2ccccc2)N2CCN(C(=O)c3cc(-c4nc5cc(C(F)(F)F)ccc5o4)ccc3F)CC2)o1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 46 | 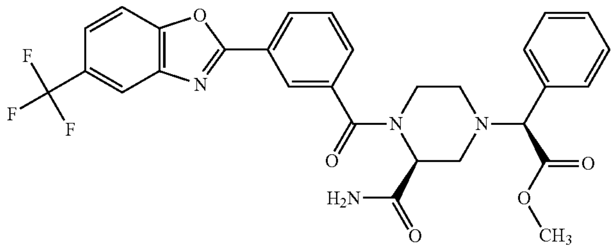 [SMILES: COC(=O)[C@H](c1ccccc1)N1CCN(C(=O)c2cccc(-c3nc4cc(C(F)(F)F)ccc4o3)c2)[C@H](C(N)=O)C1] | 4.4 |
| 47 [b] | 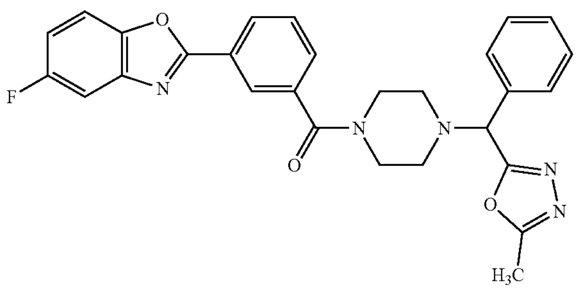 [SMILES: Cc1nnc(C(c2ccccc2)N2CCN(C(=O)c3cccc(-c4nc5cc(F)ccc5o4)c3)CC2)o1] | 4.5 |
| 48 | 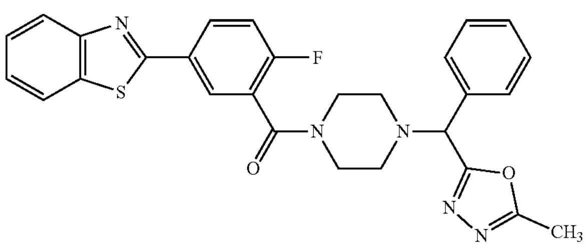 [SMILES: Cc1nnc(C(c2ccccc2)N2CCN(C(=O)c3cc(-c4nc5ccccc5s4)ccc3F)CC2)o1] | |
| 49 | 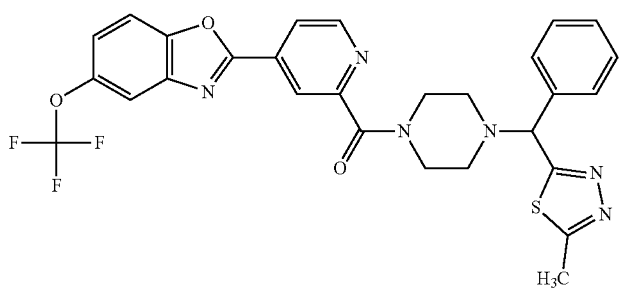 [SMILES: Cc1nnc(C(c2ccccc2)N2CCN(C(=O)c3cc(-c4nc5cc(OC(F)(F)F)ccc5o4)ccn3)CC2)s1] | 4.8 |
| 50 | 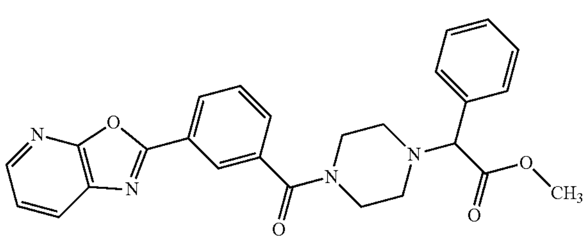 [SMILES: COC(=O)C(c1ccccc1)N1CCN(C(=O)c2cccc(-c3nc4cccnc4o3)c2)CC1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 51 [b] | 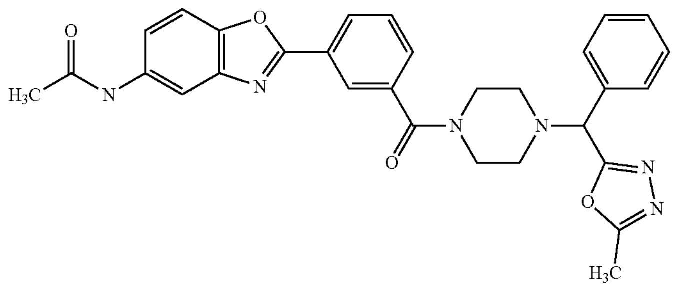 [SMILES: CC(=O)Nc1ccc2oc(-c3cccc(C(=O)N4CCN(C(c5ccccc5)c5nnc(C)o5)CC4)c3)nc2c1] | 4.3 |
| 52 | 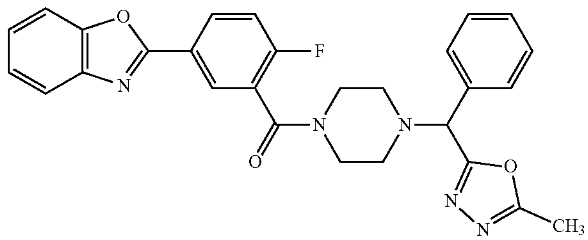 [SMILES: Cc1nnc(C(c2ccccc2)N2CCN(C(=O)c3cc(-c4nc5ccccc5o4)ccc3F)CC2)o1] | |
| 53 [a] | 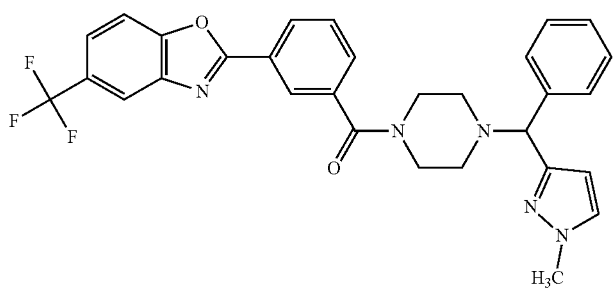 [SMILES: Cn1ccc(C(c2ccccc2)N2CCN(C(=O)c3cccc(-c4nc5cc(C(F)(F)F)ccc5o4)c3)CC2)n1] | <4.3 |
| 54 | 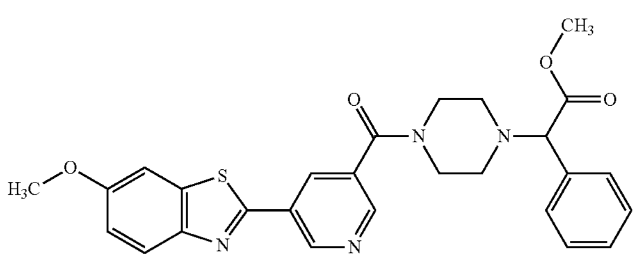 [SMILES: COC(=O)C(c1ccccc1)N1CCN(C(=O)c2cncc(-c3nc4ccc(OC)cc4s3)c2)CC1] | 4.3 |
| 55 | 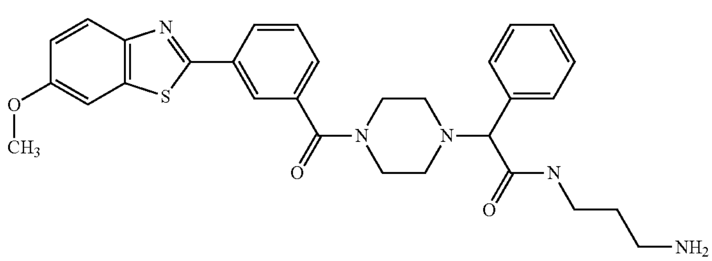 [SMILES: COc1ccc2nc(-c3cccc(C(=O)N4CCN(C(C(=O)NCCCN)c5ccccc5)CC4)c3)sc2c1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 56 | 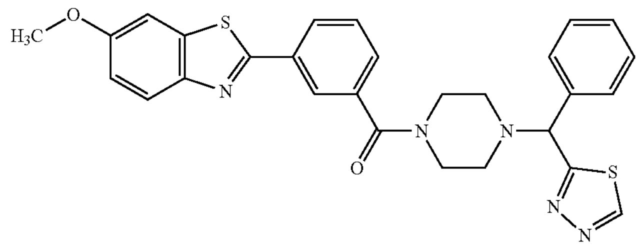 [SMILES: COc1ccc2nc(-c3cccc(C(=O)N4CCN(C(c5ccccc5)c5nncs5)CC4)c3)sc2c1] | <4.3 |
| 57 | 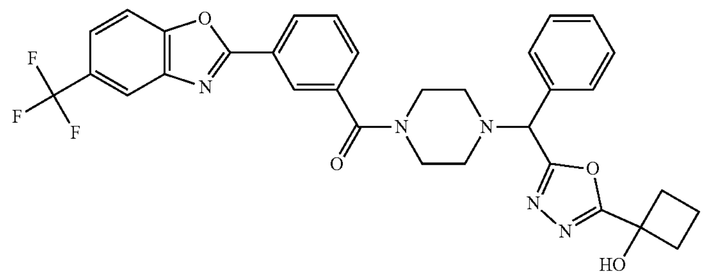 [SMILES: O=C(c1cccc(-c2nc3cc(C(F)(F)F)ccc3o2)c1)N1CCN(C(c2ccccc2)c2nnc(C3(O)CCC3)o2)CC1] | 4.4 |
| 58 | 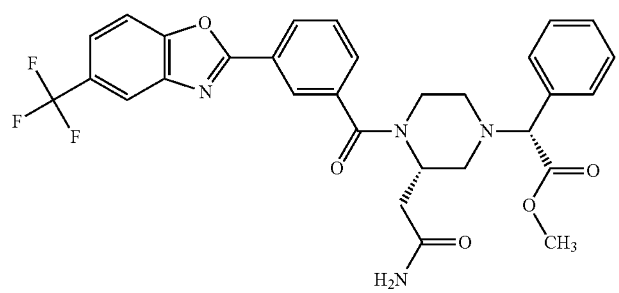 [SMILES: COC(=O)[C@@H](c1ccccc1)N1CCN(C(=O)c2cccc(-c3nc4cc(C(F)(F)F)ccc4o3)c2)[C@@H](CC(N)=O)C1] | 4.4 |
| 59 | 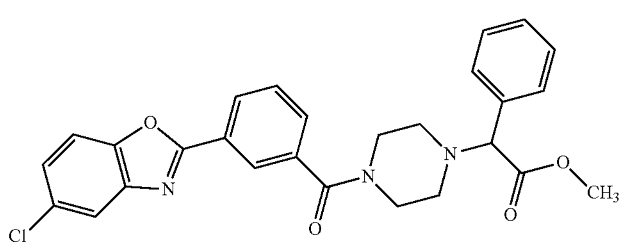 [SMILES: COC(=O)C(c1ccccc1)N1CCN(C(=O)c2cccc(-c3nc4cc(Cl)ccc4o3)c2)CC1] | <4.3 |
| 60 | 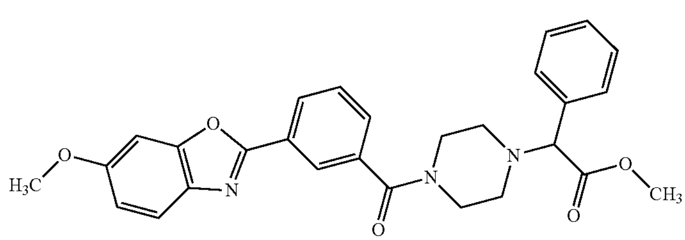 | 4.6 |

TABLE 2-continued

Molecular structure of preferred compounds of formula (I) with cytotoxicity levels (pCC50).

| Example | Structure | Cytotoxicity (pCC50) MDCK |
|---|---|---|
| 61 | 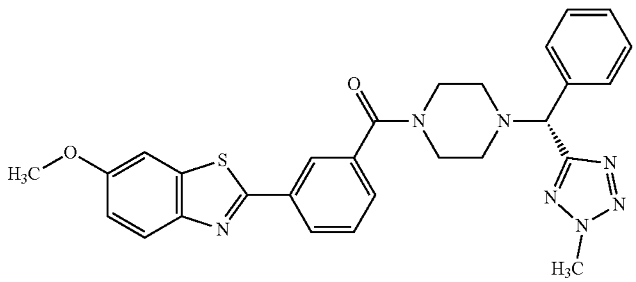 [SMILES: COc1ccc2nc(-c3cccc(C(=O)N4CCN([C@H](c5ccccc5)c5nnn(C)n5)CC4)c3)sc2c1] | 4.4 |
| 62 | 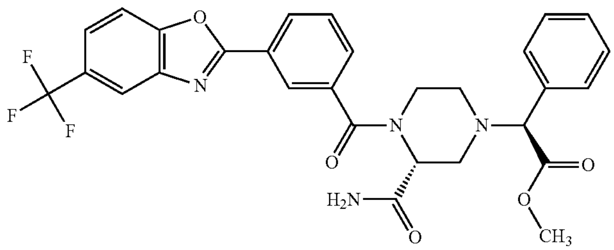 [SMILES: COC(=O)[C@H](c1ccccc1)N1CCN(C(=O)c2cccc(-c3nc4cc(C(F)(F)F)ccc4o3)c2)[C@@H](C(N)=O)C1] | 4.4 |
| 63 | 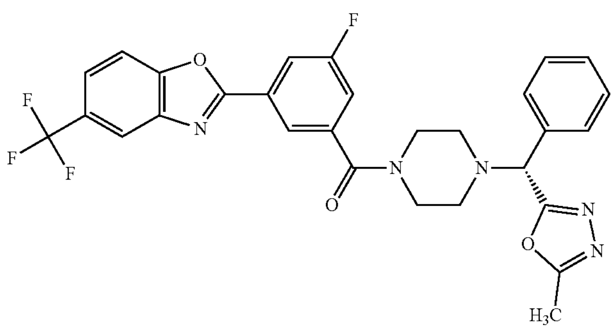 [SMILES: Cc1nnc([C@@H](c2ccccc2)N2CCN(C(=O)c3cc(F)cc(-c4nc5cc(C(F)(F)F)ccc5o4)c3)CC2)o1] | <4.3 |
| 64 | 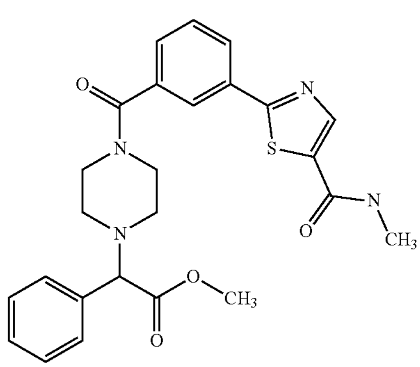 [SMILES: CNC(=O)c1cnc(-c2cccc(C(=O)N3CCN(C(C(=O)OC)c4ccccc4)CC3)c2)s1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 65 | 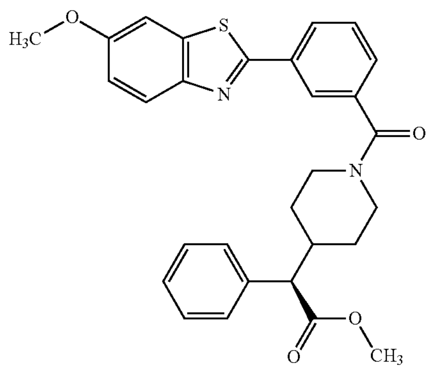 | 4.4 |
| 66 | 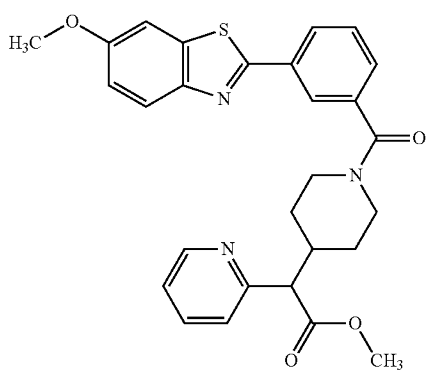 | 4.7 |
| 67 | 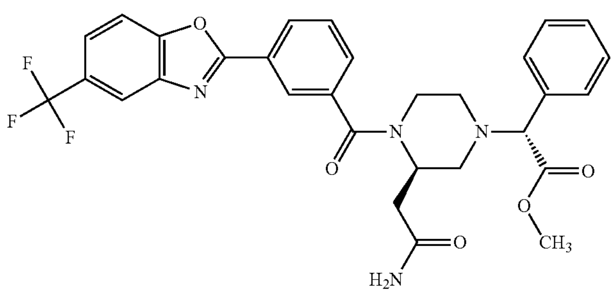 [SMILES: COC(=O)[C@@H](c1ccccc1)N1CCN(C(=O)c2cccc(-c3nc4cc(C(F)(F)F)ccc4o3)c2)[C@H](CC(N)=O)C1] | 4.4 |
| 68 | 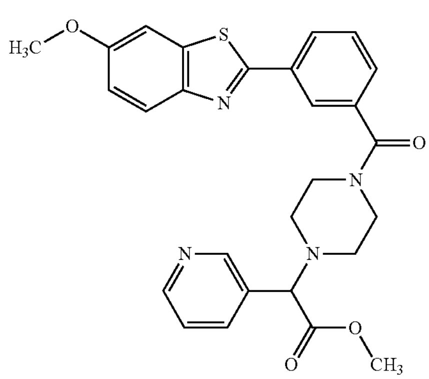 | 5.0 |

TABLE 2-continued

Molecular structure of preferred compounds of formula (I) with cytotoxicity levels (pCC50).

| Example | Structure | Cytotoxicity (pCC50) MDCK |
|---|---|---|
| 69 | 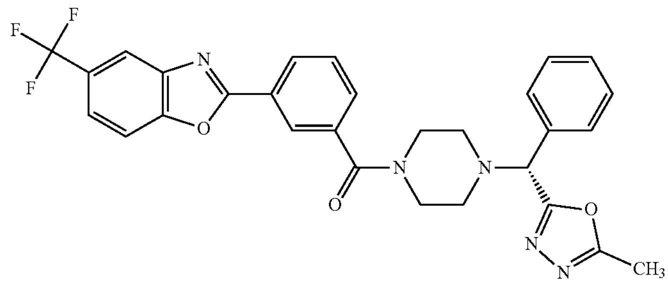 [SMILES: Cc1nnc([C@@H](c2ccccc2)N2CCN(C(=O)c3cccc(-c4nc5cc(C(F)(F)F)ccc5o4)c3)CC2)o1] | 5.0 |
| 70 | 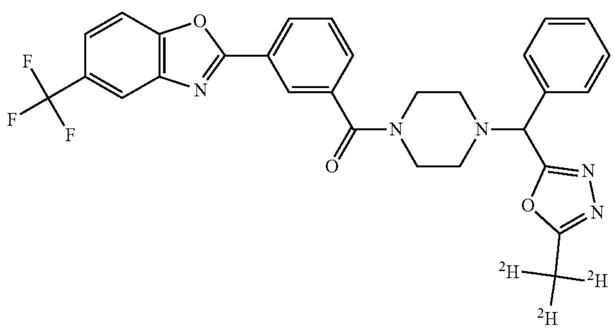 [SMILES: [2H]C([2H])([2H])c1nnc(C(c2ccccc2)N2CCN(C(=O)c3cccc(-c4nc5cc(C(F)(F)F)ccc5o4)c3)CC2)o1] | <4.3 |
| 71 | 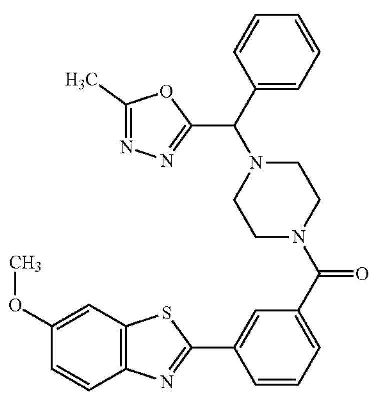 [SMILES: COc1ccc2nc(-c3cccc(C(=O)N4CCN(C(c5ccccc5)c5nnc(C)o5)CC4)c3)sc2c1] | <4.3 |
| 72 | 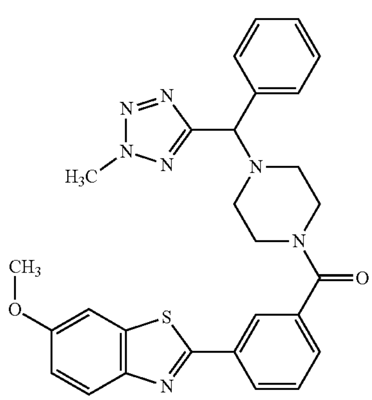 [SMILES: COc1ccc2nc(-c3cccc(C(=O)N4CCN(C(c5ccccc5)c5nnn(C)n5)CC4)c3)sc2c1] | 4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 73 | 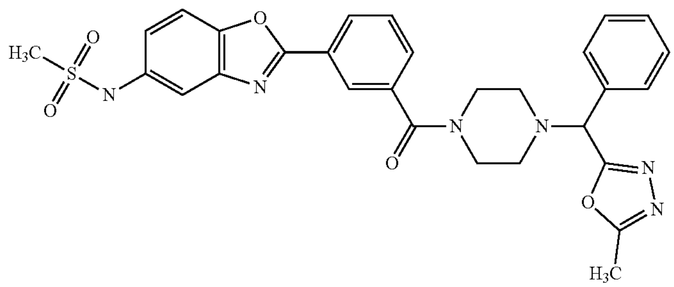 [SMILES: Cc1nnc(C(c2ccccc2)N2CCN(C(=O)c3cccc(-c4nc5cc(NS(C)(=O)=O)ccc5o4)c3)CC2)o1] | <4.3 |
| 74 | 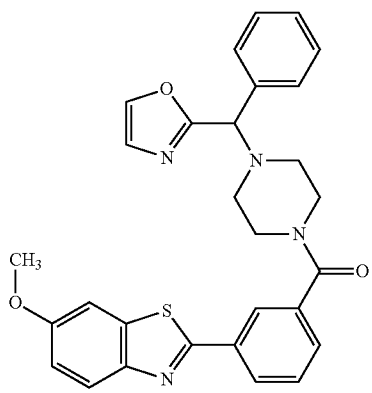 [SMILES: COc1ccc2nc(-c3cccc(C(=O)N4CCN(C(c5ccccc5)c5ncco5)CC4)c3)sc2c1] | <4.3 |
| 75 | 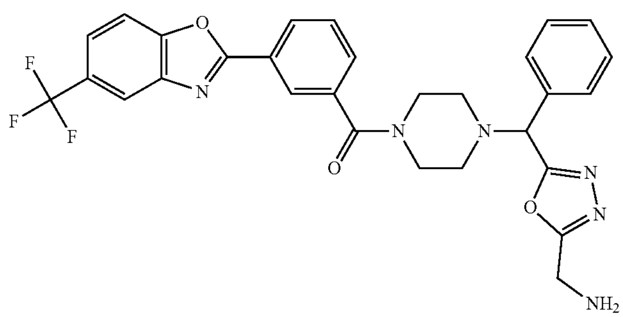 [SMILES: NCc1nnc(C(c2ccccc2)N2CCN(C(=O)c3cccc(-c4nc5cc(C(F)(F)F)ccc5o4)c3)CC2)o1] | 5.0 |
| 76 | 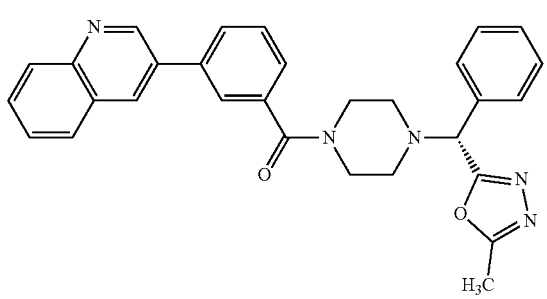 [SMILES: Cc1nnc([C@@H](c2ccccc2)N2CCN(C(=O)c3cccc(-c4cnc5ccccc5c4)c3)CC2)o1] | 4.8 |

TABLE 2-continued

Molecular structure of preferred compounds of formula (I) with cytotoxicity levels (pCC50).

| Example | Structure | Cytotoxicity (pCC50) MDCK |
|---------|-----------|---------------------------|
| 77 | 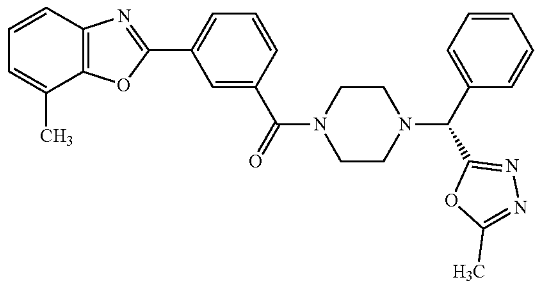 [SMILES: Cc1nnc([C@@H](c2ccccc2)N2CCN(C(=O)c3cccc(-c4nc5cccc(C)c5o4)c3)CC2)o1] | 5.4 |
| 78 | 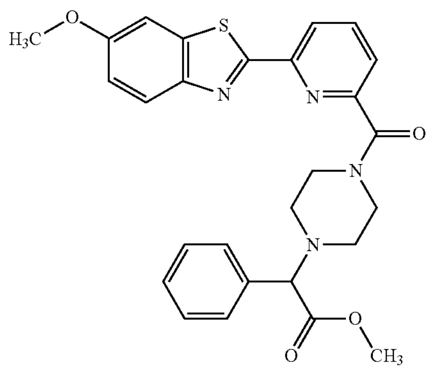 | <4.3 |
| 79 | 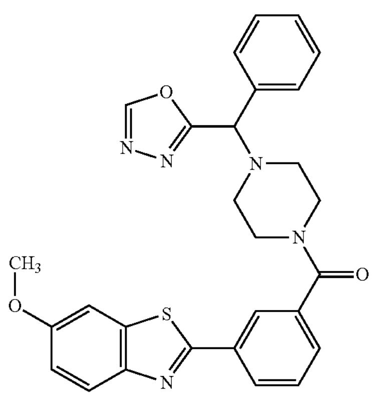 [SMILES: COc1ccc2nc(-c3cccc(C(=O)N4CCN(C(c5ccccc5)c5nnco5)CC4)c3)sc2c1] | <4.3 |
| 80 | 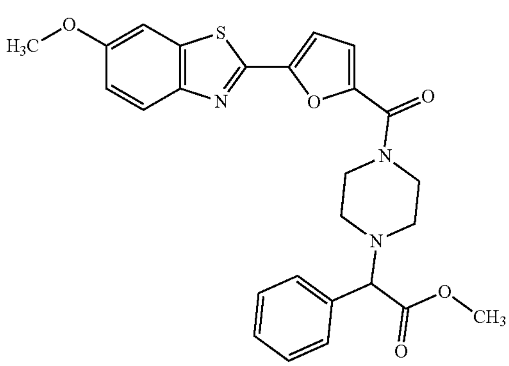 | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 81 | 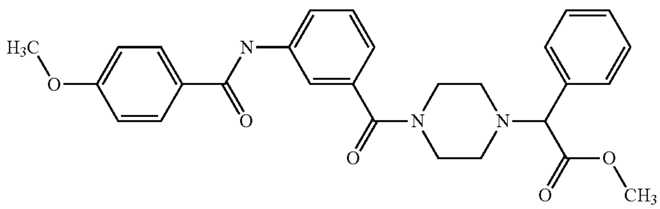 [SMILES: COC(=O)C(c1ccccc1)N1CCN(C(=O)c2cccc(NC(=O)c3ccc(OC)cc3)c2)CC1] | <4.3 |
| 82 | 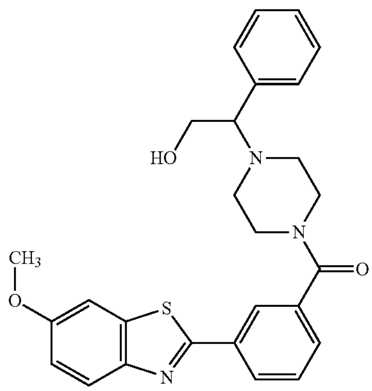 [SMILES: COc1ccc2nc(-c3cccc(C(=O)N4CCN(C(CO)c5ccccc5)CC4)c3)sc2c1] | 5.3 |
| 83 | 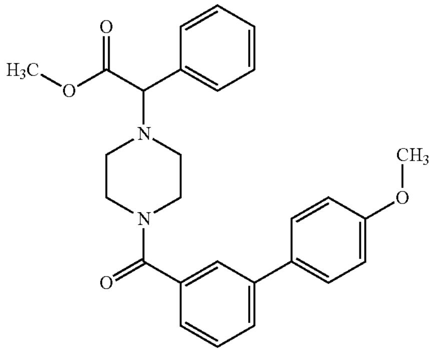 | 4.4 |
| 84 | 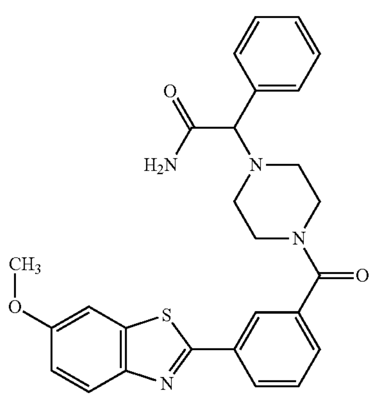 [SMILES: COc1ccc2nc(-c3cccc(C(=O)N4CCN(C(C(N)=O)c5ccccc5)CC4)c3)sc2c1] | <4.3 |

TABLE 2-continued

Molecular structure of preferred compounds of formula (I) with cytotoxicity levels (pCC50).

| Example | Structure | Cytotoxicity (pCC50) MDCK |
|---------|-----------|---------------------------|
| 85 [a] | 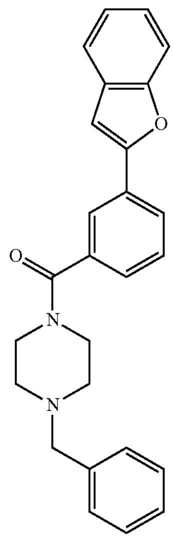 [SMILES: O=C(c1cccc(-c2cc3ccccc3o2)c1)N1CCN(Cc2ccccc2)CC1] | 5.0 |
| 86 | 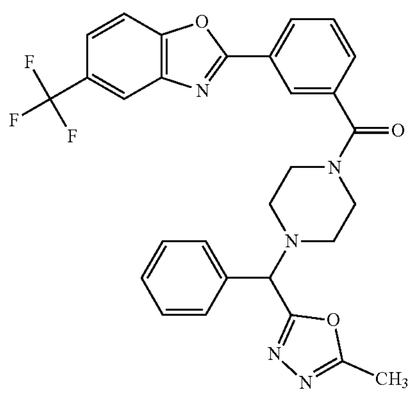 [SMILES: Cc1nnc(C(c2ccccc2)N2CCN(C(=O)c3cccc(-c4nc5cc(C(F)(F)F)ccc5o4)c3)CC2)o1] | 4.5 |
| 87 | 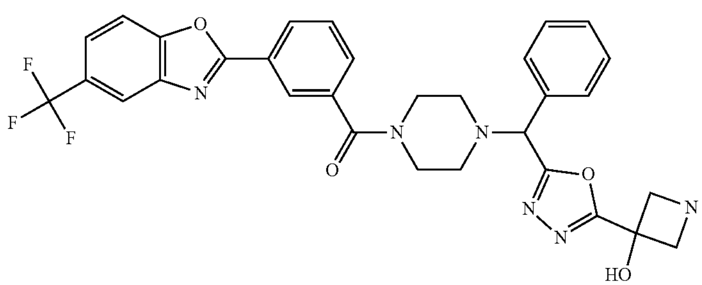 [SMILES: O=C(c1cccc(-c2nc3cc(C(F)(F)F)ccc3o2)c1)N1CCN(C(c2ccccc2)c2nnc(C3(O)CNC3)o2)CC1] | <4.3 |
| 88 | 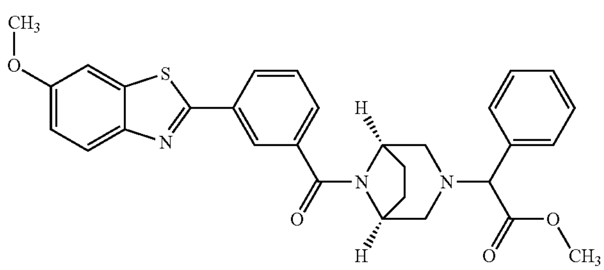 [SMILES: COC(=O)C(c1ccccc1)N1C[C@H]2CC[C@@H](C1)N2C(=O)c1cccc(-c2nc3ccc(OC)cc3s2)c1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 89 | 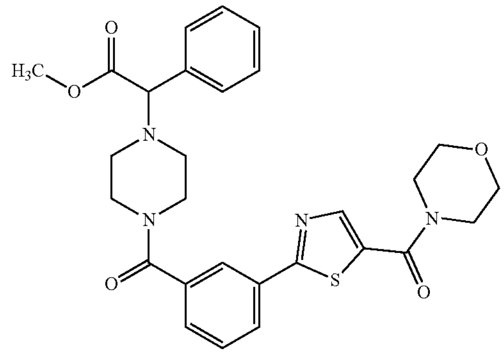 [SMILES: COC(=O)C(c1ccccc1)N1CCN(C(=O)c2cccc(-c3ncc(C(=O)N4CCOCC4)s3)c2)CC1] | <4.3 |
| 90 | 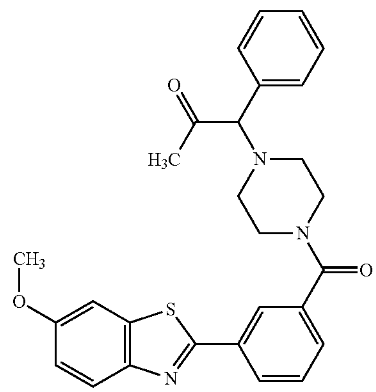 [SMILES: COc1ccc2nc(-c3cccc(C(=O)N4CCN(C(C(C)=O)c5ccccc5)CC4)c3)sc2c1] | 4.5 |
| 91 [a] | 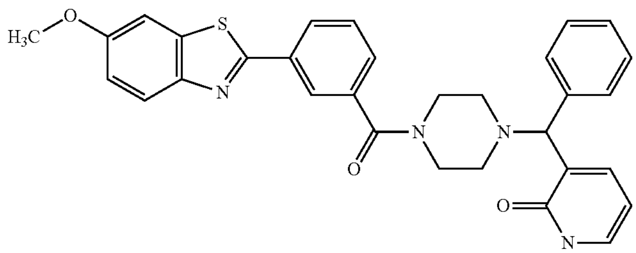 [SMILES: COc1ccc2nc(-c3cccc(C(=O)N4CCN(C(c5ccccc5)c5ccc[nH]c5=O)CC4)c3)sc2c1] | 4.4 |
| 92 | 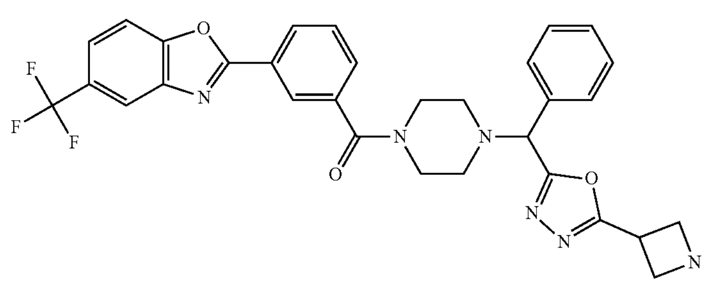 [SMILES: O=C(c1cccc(-c2nc3cc(C(F)(F)F)ccc3o2)c1)N1CCN(C(c2ccccc2)c2nnc(C3CNC3)o2)CC1] | 5.0 |

TABLE 2-continued

Molecular structure of preferred compounds of formula (I) with cytotoxicity levels (pCC50).

| Example | Structure | Cytotoxicity (pCC50) MDCK |
|---|---|---|
| 93 | 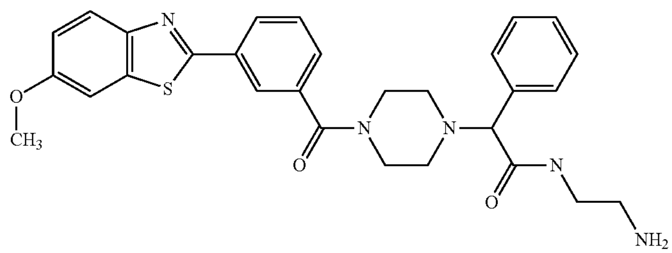 [SMILES: COc1ccc2nc(-c3cccc(C(=O)N4CCN(C(C(=O)NCCN)c5ccccc5)CC4)c3)sc2c1] | 4.8 |
| 94 | 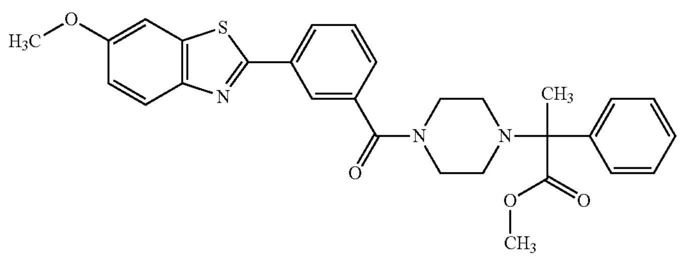 [SMILES: COC(=O)C(C)(c1ccccc1)N1CCN(C(=O)c2cccc(-c3nc4ccc(OC)cc4s3)c2)CC1] | 5.6 |
| 95 | 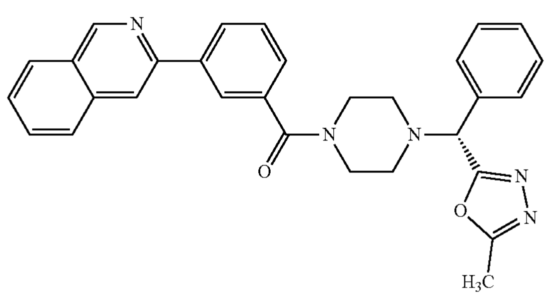 [SMILES: Cc1nnc([C@@H](c2ccccc2)N2CCN(C(=O)c3cccc(-c4cc5ccccc5cn4)c3)CC2)o1] | 4.4 |
| 96 | 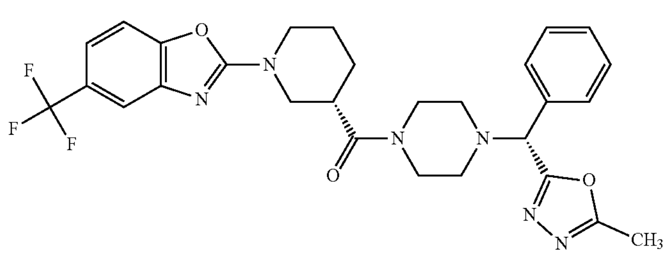 [SMILES: Cc1nnc([C@@H](c2ccccc2)N2CCN(C(=O)[C@H]3CCCN(c4nc5cc(C(F)(F)F)ccc5o4)C3)CC2)o1] | |

TABLE 2-continued

Molecular structure of preferred compounds of formula (I) with cytotoxicity levels (pCC50).

| Example | Structure | Cytotoxicity (pCC50) MDCK |
|---|---|---|
| 97 | 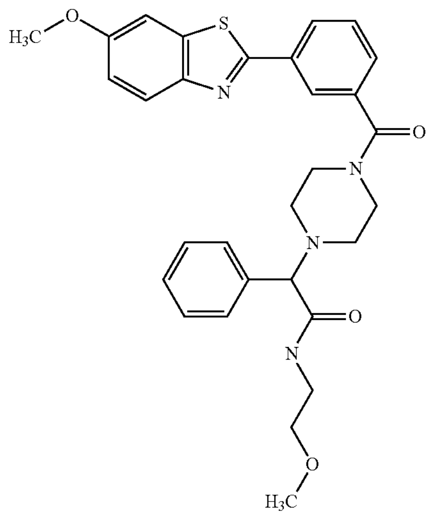 [SMILES: COCCNC(=O)C(c1ccccc1)N1CCN(C(=O)c2cccc(-c3nc4ccc(OC)cc4s3)c2)CC1] | 5.0 |
| 98 | 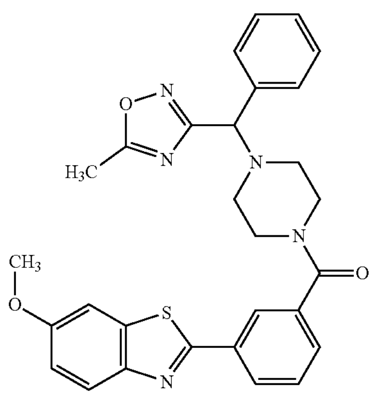 [SMILES: COc1ccc2nc(-c3cccc(C(=O)N4CCN(C(c5ccccc5)c5noc(C)n5)CC4)c3)sc2c1] | 4.9 |
| 99 | 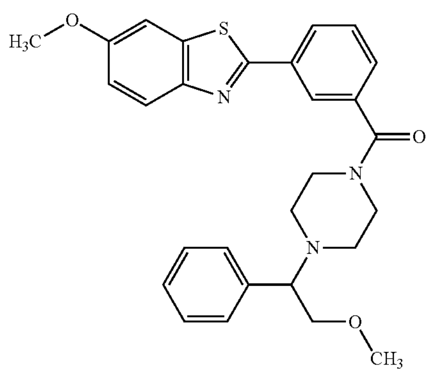 [SMILES: COCC(c1ccccc1)N1CCN(C(=O)c2cccc(-c3nc4ccc(OC)cc4s3)c2)CC1] | <4.3 |
| 100 | 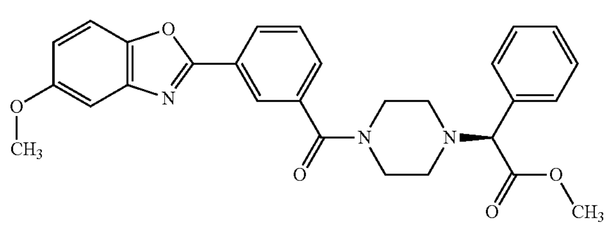 [SMILES: COC(=O)[C@H](c1ccccc1)N1CCN(C(=O)c2cccc(-c3nc4cc(OC)ccc4o3)c2)CC1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 101 | 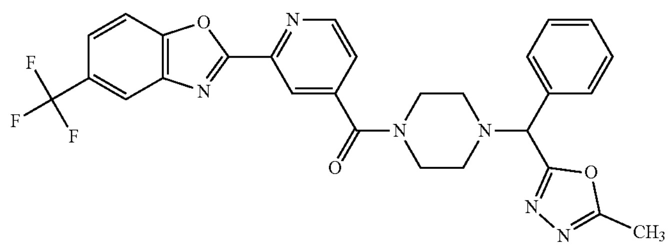 [SMILES: Cc1nnc(C(c2ccccc2)N2CCN(C(=O)c3ccnc(-c4nc5cc(C(F)(F)F)ccc5o4)c3)CC2)o1] | |
| 102 | 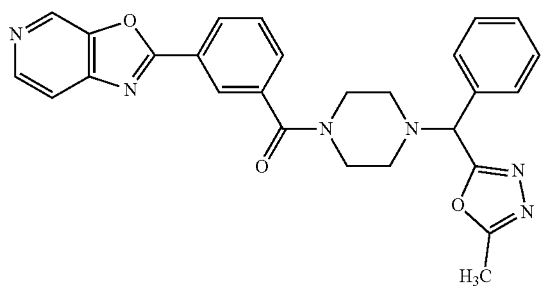 [SMILES: Cc1nnc(C(c2ccccc2)N2CCN(C(=O)c3cccc(-c4nc5ccncc5o4)c3)CC2)o1] | <4.3 |
| 103 | 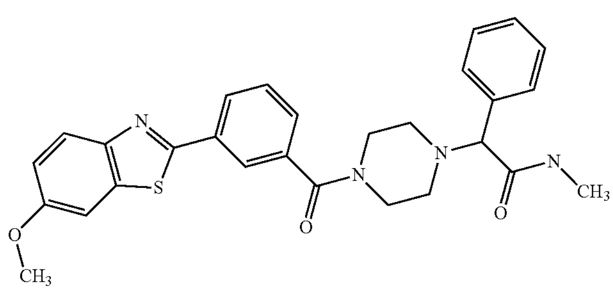 [SMILES: CNC(=O)C(c1ccccc1)N1CCN(C(=O)c2cccc(-c3nc4ccc(OC)cc4s3)c2)CC1] | 4.5 |
| 104 | 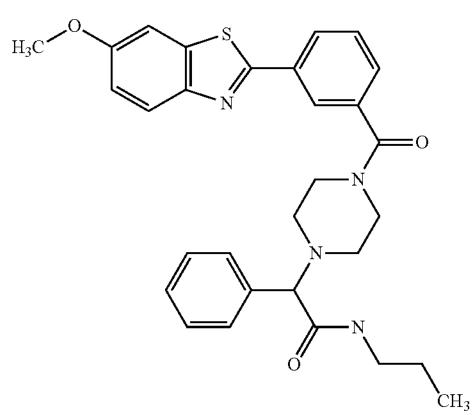 [SMILES: CCCNC(=O)C(c1ccccc1)N1CCN(C(=O)c2cccc(-c3nc4ccc(OC)cc4s3)c2)CC1] | 5.1 |

TABLE 2-continued

Molecular structure of preferred compounds of formula (I) with cytotoxicity levels (pCC50).

| Example | Structure | Cytotoxicity (pCC50) MDCK |
|---------|-----------|---------------------------|
| 105 | 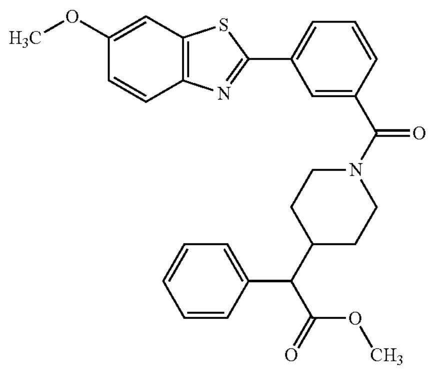 [SMILES: COC(=O)C(c1ccccc1)C1CCN(C(=O)c2cccc(-c3nc4ccc(OC)cc4s3)c2)CC1] | <4.3 |
| 106 | 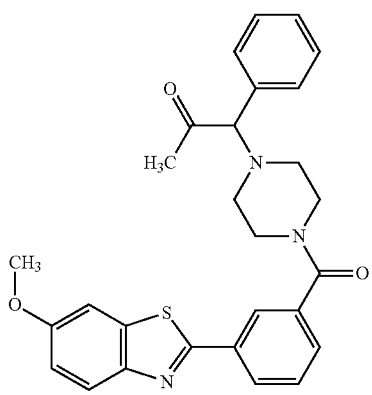 [SMILES: COc1ccc2nc(-c3cccc(C(=O)N4CCN(C(C(C)=O)c5ccccc5)CC4)c3)sc2c1] | 4.4 |
| 107 | 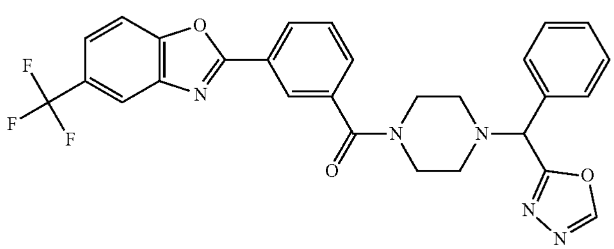 [SMILES: O=C(c1cccc(-c2nc3cc(C(F)(F)F)ccc3o2)c1)N1CCN(C(c2ccccc2)c2nnco2)CC1] | <4.3 |
| 108 | 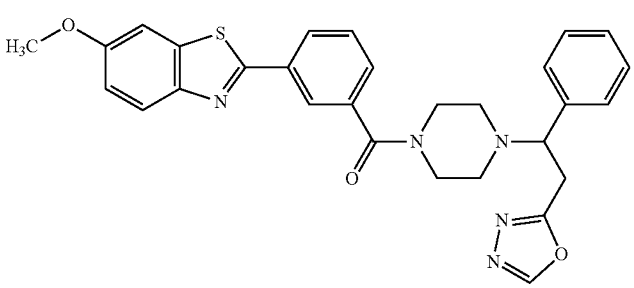 [SMILES: COc1ccc2nc(-c3cccc(C(=O)N4CCN(C(Cc5nnco5)c5ccccc5)CC4)c3)sc2c1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 109 [a] | 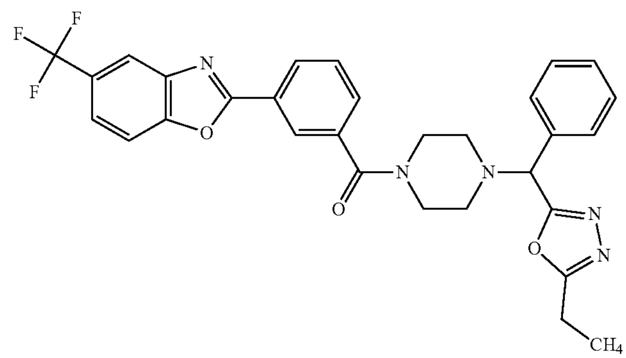 [SMILES: CCc1nnc(C(c2ccccc2)N2CCN(C(=O)c3cccc(-c4nc5cc(C(F)(F)F)ccc5o4)c3)CC2)o1] | 5.0 |
| 110 | 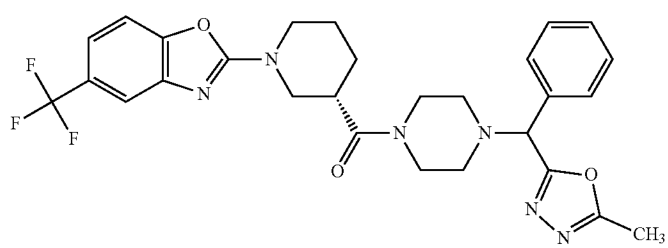 [SMILES: Cc1nnc(C(c2ccccc2)N2CCN(C(=O)[C@H]3CCCN(c4nc5cc(C(F)(F)F)ccc5o4)C3)CC2)o1] | |
| 111 | 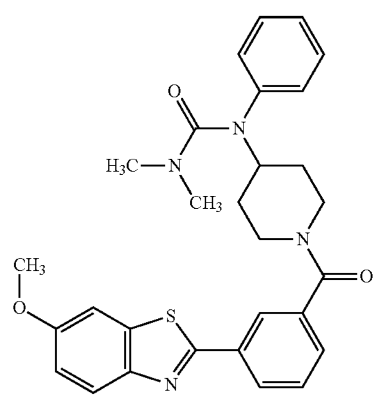 [SMILES: COc1ccc2nc(-c3cccc(C(=O)N4CCC(N(C(=O)N(C)C)c5ccccc5)CC4)c3)sc2c1] | 5.6 |
| 112 | 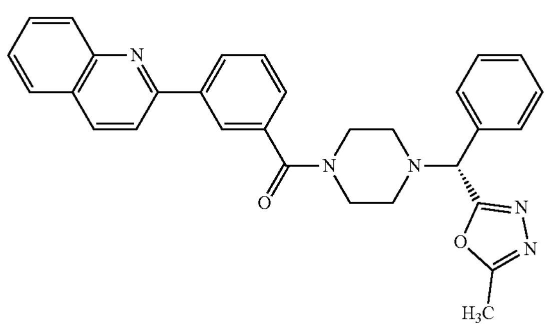 [SMILES: Cc1nnc([C@@H](c2ccccc2)N2CCN(C(=O)c3cccc(-c4ccc5ccccc5n4)c3)CC2)o1] | 5.1 |

TABLE 2-continued

Molecular structure of preferred compounds of formula (I) with cytotoxicity levels (pCC50).

| Example | Structure | Cytotoxicity (pCC50) MDCK |
|---------|-----------|---------------------------|
| 113 | 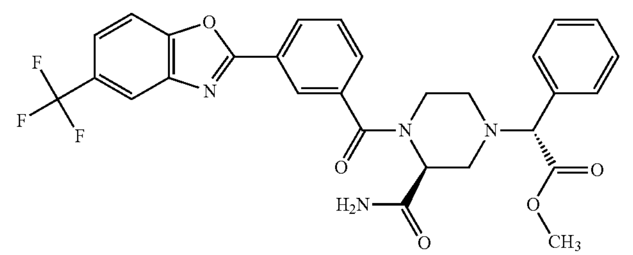 [SMILES: COC(=O)[C@@H](c1ccccc1)N1CCN(C(=O)c2cccc(-c3nc4cc(C(F)(F)F)ccc4o3)c2)[C@H](C(N)=O)C1] | <4.3 |
| 114 | 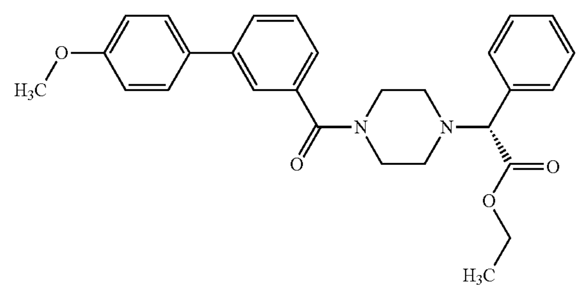 [SMILES: CCOC(=O)[C@@H](c1ccccc1)N1CCN(C(=O)c2cccc(-c3ccc(OC)cc3)c2)CC1] | 5.4 |
| 115 | 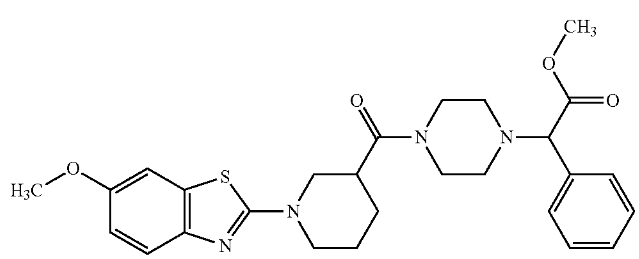 [SMILES: COC(=O)C(c1ccccc1)N1CCN(C(=O)C2CCCN(c3nc4ccc(OC)cc4s3)C2)CC1] | 5.4 |
| 116 | 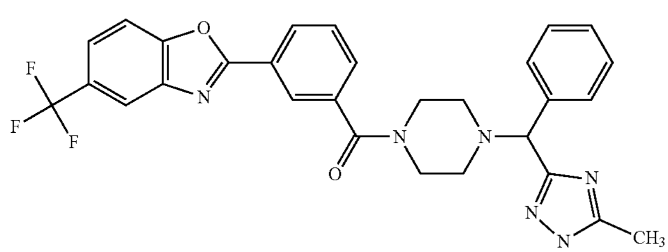 [SMILES: Cc1nc(C(c2ccccc2)N2CCN(C(=O)c3cccc(-c4nc5cc(C(F)(F)F)ccc5o4)c3)CC2)n[nH]1] | 4.3 |
| 117 | 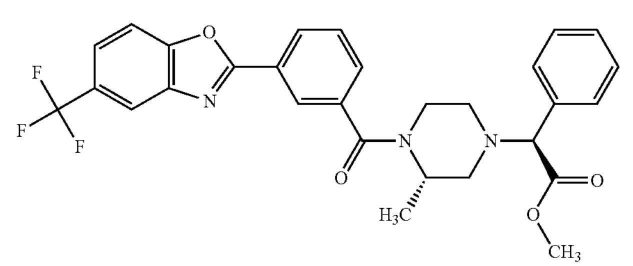 [SMILES: COC(=O)[C@H](c1ccccc1)N1CCN(C(=O)c2cccc(-c3nc4cc(C(F)(F)F)ccc4o3)c2)[C@@H](C)C1] | <4.3 |

TABLE 2-continued
Molecular structure of preferred compounds of formula (I) with cytotoxicity levels (pCC50).
| Example | Structure | Cytotoxicity (pCC50) MDCK |
|---------|-----------|---------------------------|
| 118 | 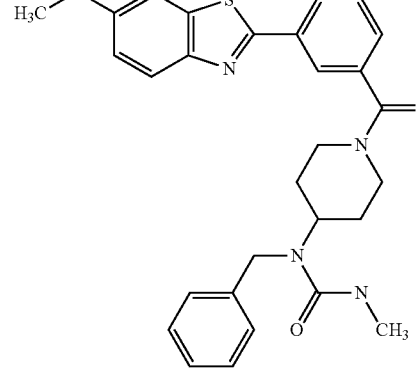 | 5.7 |
| 119 | 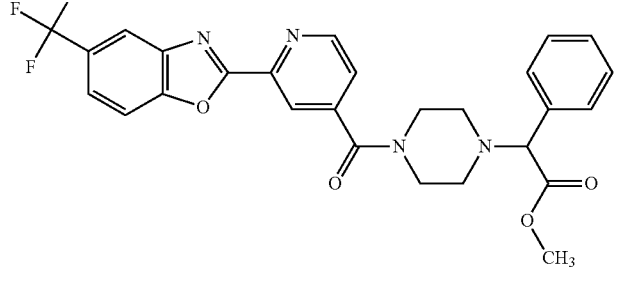 | 5.0 |
| 120 | 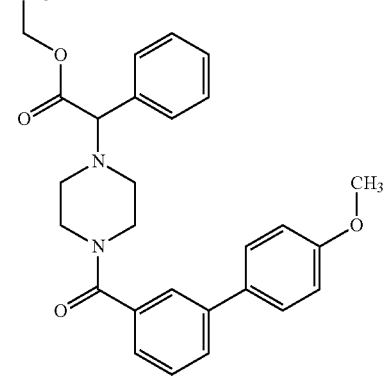 | <4.3 |
| 121 | 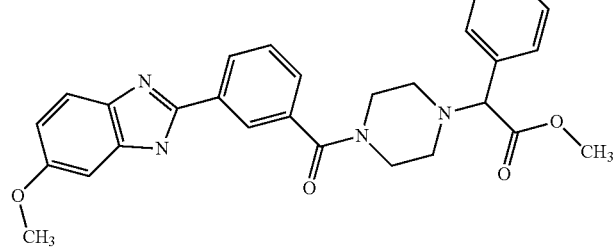 | 5.1 |

TABLE 2-continued

Molecular structure of preferred compounds of formula (I) with cytotoxicity levels (pCC50).

| Example | Structure | Cytotoxicity (pCC50) MDCK |
|---|---|---|
| 122 | 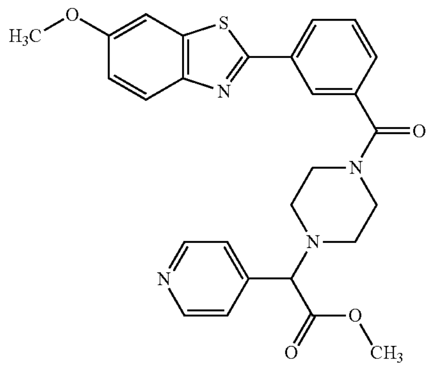 | 5.0 |
| 123 | 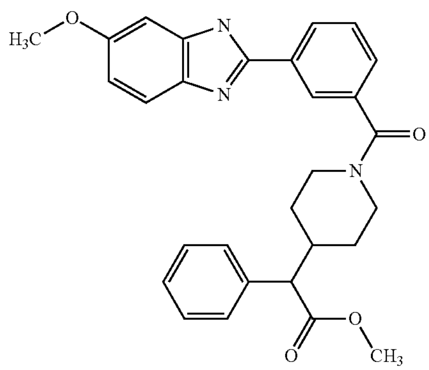 | <4.3 |
| 124 | 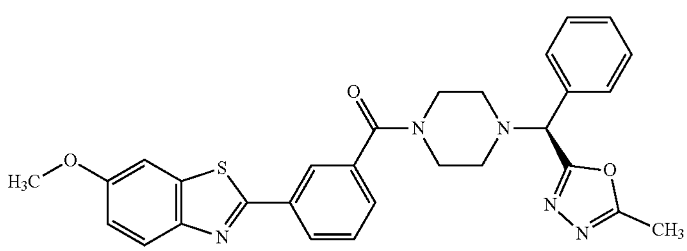 | 4.8 |
| 125 | 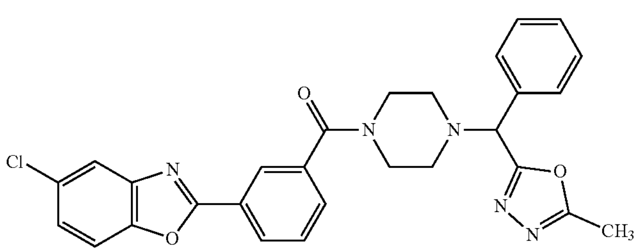 [SMILES: Cc1nnc(C(c2ccccc2)N2CCN(C(=O)c3cccc(-c4nc5cc(Cl)ccc5o4)c3)CC2)o1] | 4.6 |

TABLE 2-continued

Molecular structure of preferred compounds of formula (I) with cytotoxicity levels (pCC50).

| Example | Structure | Cytotoxicity (pCC50) MDCK |
|---|---|---|
| 126 | 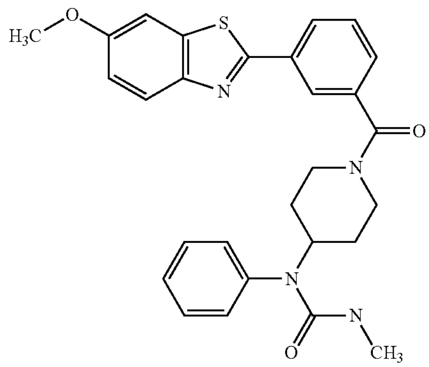 | 5.2 |
| 127 | 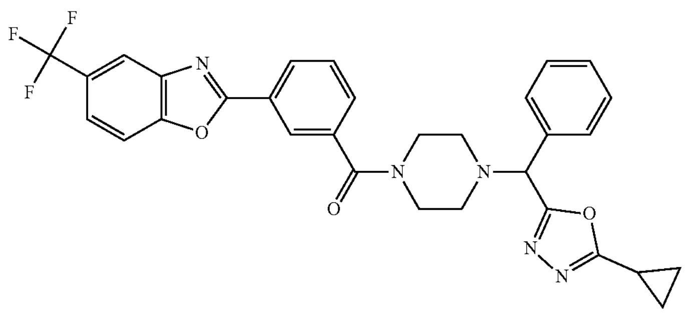 [SMILES: O=C(c1cccc(-c2nc3cc(C(F)(F)F)ccc3o2)c1)N1CCN(C(c2ccccc2)c2nnc(C3CC3)o2)CC1] | <4.3 |
| 128 | 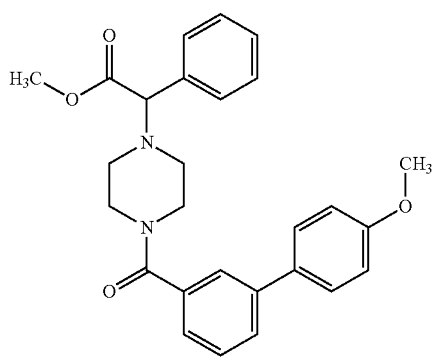 | <4.3 |
| 129 | 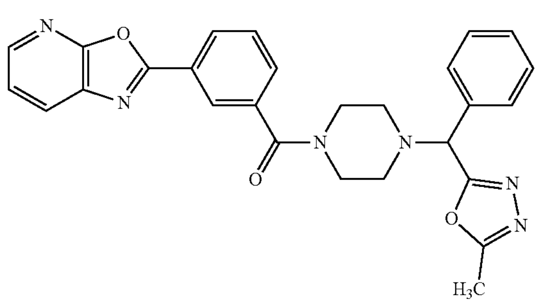 [SMILES: Cc1nnc(C(c2ccccc2)N2CCN(C(=O)c3cccc(-c4nc5cccnc5o4)c3)CC2)o1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 130 | 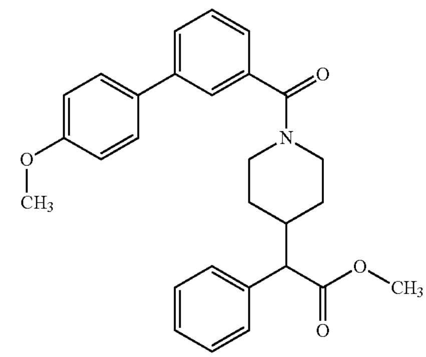 [SMILES: COC(=O)C(c1ccccc1)C1CCN(C(=O)c2cccc(-c3ccc(OC)cc3)c2)CC1] | 4.4 |
| 131 | 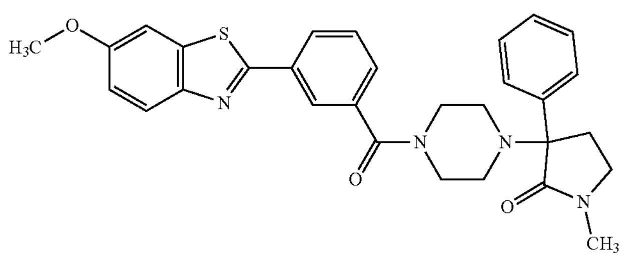 [SMILES: COc1ccc2nc(-c3cccc(C(=O)N4CCN(C5(c6ccccc6)CCN(C)C5=O)CC4)c3)sc2c1] | 4.7 |
| 132 | 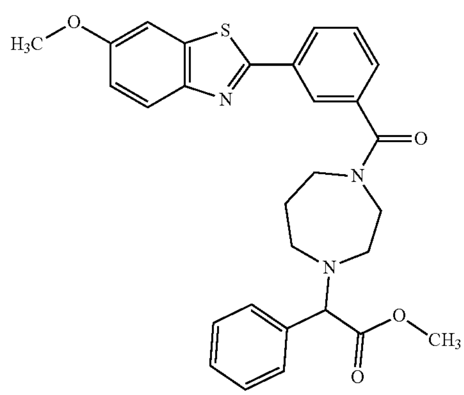 | <4.3 |
| 133 | 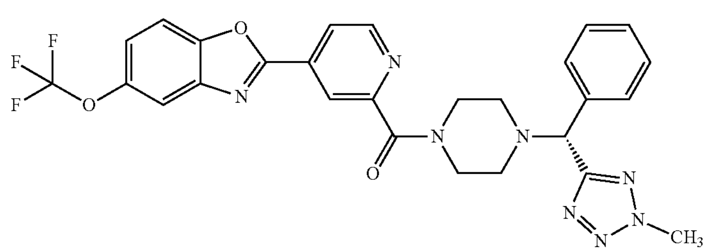 [SMILES: Cn1nnc([C@@H](c2ccccc2)N2CCN(C(=O)c3cc(-c4nc5cc(OC(F)(F)F)ccc5o4)ccn3)CC2)n1] | <4.3 |

TABLE 2-continued

Molecular structure of preferred compounds of formula (I) with cytotoxicity levels (pCC50).

| Example | Structure | Cytotoxicity (pCC50) MDCK |
|---|---|---|
| 134 | [structure] | <4.3 |

*a* hydrochloric acid salt; *b* trifluoromethanesulfonic acid salt.

The invention claimed is:

1. A compound having formula (I) or a stereoisomer, a pharmaceutically acceptable salt, a solvate, or a polymorph thereof, wherein:

(I)

B is —CH$_2$— or —CH$_2$CH$_2$—;
W is N;
either:
a) X is CR$_4$ or N, wherein R$_4$ is hydrogen, methyl, ethyl or propyl; and R$_1$ is hydrogen; —CH$_2$OH; —CH$_2$OCH$_3$; —C(O)CH$_3$; —C(O)OCH$_3$; —C(O)OCH$_2$CH$_3$; —C(O)NH$_2$; —C(O)NH(CH$_2$)$_2$OCH$_3$; —C(O)NH(CH$_3$); —C(O)NH(CH$_2$)$_n$CH$_3$, wherein n is 2 or 3; or —C(O)NH(CH$_2$)$_o$NH$_2$, wherein o is 2 or 3; or a carbocyclic or heterocyclic radical selected from the group consisting of cyclohexyl, pyridyl, pyrrolyl, oxazolyl, oxadiazolyl, pyrazolyl, triazolyl, tetrazolyl, thiadiazolyl, and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone; or
b) X is CR$_4$, and R$_1$ and CR$_4$ are taken together to form a carbocyclic or heterocyclic radical;
Y$_1$ is —(CH$_2$)$_p$—, wherein p is 0, 1, 2 or 3;
Y$_2$ is —(CH$_2$)$_q$—, wherein q is 0, 1, 2 or 3;
Z$_1$ and Z$_2$ are independently selected from the group consisting of CH or N, with the proviso that at least one of Z$_1$ and Z$_2$ is CH;
R$_2$ is hydrogen, methyl, —C(O)NH$_2$, or —CH$_2$C(O)NH$_2$ and R$_3$ is hydrogen; or R$_2$ and R$_3$ are taken together to form 1,2-ethanediyl or 1,3-propanediyl;
Ar is a 5-membered or 6-membered aromatic or heteroaromatic ring, optionally substituted with at least one halogen; and A is benzothiazolyl, benzoxazolyl, benzisoxazolyl, benzofuranyl, isoquinolinyl, quinazolyl, benzimidazolyl, pyridooxazolyl, or methoxyphenyl acetamide, optionally substituted with one or more substituents independently selected from the group consisting of halogen, —OH, —O—CH$_3$, —CH$_3$, —CF$_3$, —OCF$_3$, —NH$_2$, —NHCH$_3$, —N(CH$_3$)$_2$, —NHC(O)CH$_3$, —NHSO$_2$CH$_3$, cyclopropoxy or methylenesulfonyl nitrile.

2. The compound according to claim 1, wherein B is —CH$_2$— and R$_3$ is hydrogen.

3. The compound according to claim 1, wherein X is CH.

4. The compound according to claim 1, wherein W is N, B is —CH$_2$—, and X is CH.

5. The compound according to claim 1, wherein p and q are 0.

6. The compound according to claim 1, wherein A is benzoxazol-2-yl.

7. The compound according to claim 6, wherein said benzoxazol-2-yl comprises a substituent in the 5-position, said substituent in the 5-position being selected from the group consisting of —OCH$_3$, —CF$_3$, —OCF$_3$, —NH$_2$, —NHCH$_3$, —N(CH$_3$)$_2$, —NHC(O)CH$_3$, and cyclopropoxy.

8. The compound according to claim 7, wherein said substituent in the 5-position is selected from the group consisting of —OCF$_3$, —NC(O)CH$_3$, and cyclopropoxy.

9. The compound according to claim 1, wherein Ar is an optionally fluorinated phenylene, an optionally fluorinated furandiyl, or an optionally fluorinated pyridinediyl.

10. The compound according to claim 9, wherein Ar is 1,3-phenylene; 2-fluoro-1,5-phenylene; 3-fluoro-1,5-phenylene; furan-2,5-diyl; pyridine-2,4-diyl; or pyridine-2,6-diyl.

11. A compound having formula (I) or a stereoisomer, a pharmaceutically acceptable salt, a solvate, or a polymorph thereof, wherein:

(I)

B is —CH$_2$— or —CH$_2$CH$_2$—;
W is CH or N;
either:
c) X is CR$_4$ or N, wherein R$_4$ is hydrogen, methyl, ethyl or propyl; and R$_1$ is hydrogen; —CH$_2$OH; —CH$_2$OCH$_3$; —C(O)CH$_3$; —C(O)OCH$_3$; —C(O)OCH$_2$CH$_3$; —C(O)NH$_2$; —C(O)NH(CH$_2$)$_2$OCH$_3$; —C(O)NH(CH$_3$)$_m$, wherein m is 1 or 2; —C(O)NH(CH$_2$)$_n$CH$_3$, wherein n is 2 or 3; or —C(O)NH(CH$_2$)$_o$NH$_2$, wherein o is 2 or 3; or a carbocyclic or heterocyclic radical selected from the group consisting of cyclohexyl, pyridyl, pyrrolyl, oxazolyl, oxadiazolyl, pyrazolyl, triazolyl, tetrazolyl, thiadiazolyl, and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone; or
d) X is CR$_4$, and R$_1$, C, and R$_4$ are taken together to form a carbocyclic or heterocyclic radical;
Y$_1$ is —(CH$_2$)$_p$—, wherein p is 0, 1, 2 or 3;
Y$_2$ is —(CH$_2$)$_q$—, wherein q is 0, 1, 2 or 3;
Z$_1$ and Z$_2$ are independently selected from the group consisting of CH or N, with the proviso that at least one of Z$_1$ and Z$_2$ is CH;
R$_2$ is hydrogen, methyl, —C(O)NH$_2$, or —CH$_2$C(O)NH$_2$ and R$_3$ is hydrogen; or R$_2$ and R$_3$ are taken together to form 1,2-ethanediyl or 1,3-propanediyl;
Ar is an optionally fluorinated phenylene, an optionally fluorinated furandiyl, or an optionally fluorinated pyridinediyl; and
A is benzoxazol-2-yl, optionally substituted with one or more substituents independently selected from the group consisting of halogen, —OH, —O—CH$_3$, —CH$_3$, —CF$_3$, —OCF$_3$, —NH$_2$, —NHCH$_3$, —N(CH$_3$)$_2$, —NHC(O)CH$_3$, —NHSO$_2$CH$_3$, cyclopropoxy, and methylenesulfonyl nitrile.

12. The compound according to claim 11, wherein W is N.
13. A method of preparing a compound according to claim 1, comprising:

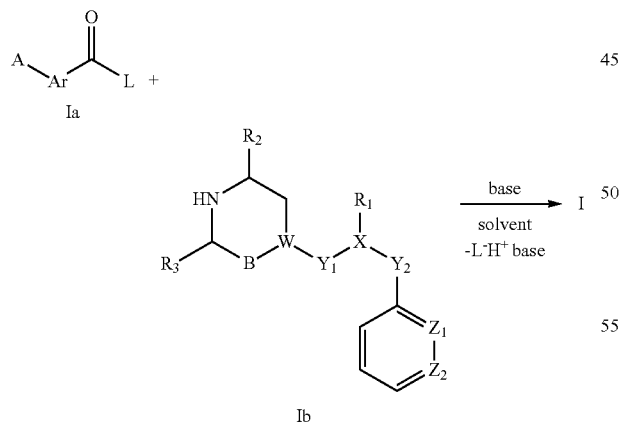

reacting an intermediate of the formula Ia, wherein L is a leaving group, with an intermediate of the formula Ib, in the presence of a base and a solvent.

14. The method of claim 13, wherein A is benzoxazol-2-yl, substituted with one or more substituents independently selected from the group consisting of halogen, —OH, —OCH$_3$, —CH$_3$, —CF$_3$, —OCF$_3$, —NH$_2$, —NHCH$_3$, —N(CH$_3$)$_2$, —NHC(O)CH$_3$, —NHSO$_2$CH$_3$, cyclopropoxy and methylenesulfonyl nitrile.

15. The method of claim 13, wherein Ar is an optionally fluorinated phenylene, an optionally fluorinated furandiyl, or an optionally fluorinated pyridinediyl.

16. A pharmaceutical composition, comprising:
an effective amount of a compound according to claim 1 as an active ingredient; and
a pharmaceutically acceptable carrier.

17. A pharmaceutical composition comprising:
an effective amount of a compound according to claim 11 as an active ingredient, and
a pharmaceutically acceptable carrier.

18. A method of preparing a pharmaceutical composition, comprising intimately mixing a pharmaceutically acceptable carrier with a therapeutically effective amount of a compound according to claim 1.

19. A method of treating influenza in a subject in need thereof, comprising administering to the subject an effective amount of a compound having formula (I) or a stereoisomer, a pharmaceutically acceptable salt, a solvate, or a polymorph thereof, wherein:

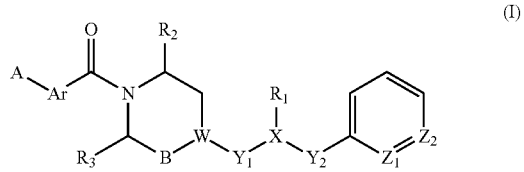

(I)

B is —CH$_2$— or —CH$_2$CH$_2$—;
W is CH or N;
either:
a) X is CR$_4$ or N, wherein R$_4$ is hydrogen, methyl, ethyl or propyl; and R$_1$ is hydrogen; —CH$_2$OH; —CH$_2$OCH$_3$; —C(O)CH$_3$; —C(O)OCH$_3$; —C(O)OCH$_2$CH$_3$; —C(O) NH$_2$; —C(O) NH(CH$_2$)$_2$OCH$_3$; —C(O) NH(CH$_3$); —C(O) NH(CH$_2$)CH$_3$, wherein n is 2 or 3; or —C(O)NH(CH$_2$)$_o$NH$_2$, wherein o is 2 or 3; or a carbocyclic or heterocyclic radical selected from the group consisting of cyclohexyl, pyridyl, pyrrolyl, oxazolyl, oxadiazolyl, pyrazolyl, triazolyl, tetrazolyl, thiadiazolyl, and imidazolidyl, optionally substituted with one or more substituents independently selected from oxo, methyl, ethyl, cyclopropyl, methoxy, methylacetamide, methanamine, azetidine, hydroxyazetidinyl, hydroxycyclobutyl and morpholinomethanone; or
b) X is CR$_4$, and R$_1$, C, and R$_4$ are taken together to form a carbocyclic or heterocyclic radical;
Y$_1$ is —(CH$_2$)$_p$—, wherein p is 0, 1, 2 or 3;
Y$_2$ is —(CH$_2$)$_q$—, wherein q is 0, 1, 2 or 3;
Z$_1$ and Z$_2$ are independently selected from the group consisting of CH or N, with the proviso that at least one of Z$_1$ and Z$_2$ is CH;
R$_2$ is hydrogen, methyl, —C(O)NH$_2$, or —CH$_2$C(O)NH$_2$ and R$_3$ is hydrogen; or R$_2$ and R$_3$ are taken together to form 1,2-ethanediyl or 1,3-propanediyl;
Ar is a 5-membered or 6-membered aromatic or heteroaromatic ring, optionally substituted with at least one halogen; and
A is benzyl, benzothiazolyl, benzoxazolyl, benzisoxazolyl, benzofuranyl, isoquinolinyl, quinazolyl, benzimidazolyl, pyridooxazolyl, or methoxyphenyl acetamide, optionally substituted with one or more substituents independently selected from the group consisting of halogen, —OH, —O—CH$_3$, —CH$_3$, —CF$_3$, —OCF$_3$, —NH$_2$, —NHCH$_3$, —N(CH$_3$)$_2$, —NHC(O)CH$_3$, —NHSO$_2$CH$_3$, cyclopropoxy or methylenesulfonyl nitrile.

20. A method of treating influenza in a subject in need thereof, comprising administering an effective amount of a composition according to claim 16 to the subject.

\* \* \* \* \*